(12) United States Patent
Muller-Spath et al.

(10) Patent No.: US 10,948,483 B2
(45) Date of Patent: Mar. 16, 2021

(54) METHOD FOR CONTROL, MONITORING AND/OR OPTIMIZATION OF A CHROMATOGRAPHIC PROCESS

(71) Applicant: ChromaCon AG, Zurich (CH)

(72) Inventors: Thomas Muller-Spath, Zurich (CH); Lars Aumann, Zurich (CH); Guido Strohlein, Zurich (CH); Michael Bavand, Lenzburg (CH); Nicole Ulmer, Schlieren (CH)

(73) Assignee: ChromaCon AG, Zurich (CH)

( * ) Notice: Subject to any disclaimer, the term of this patent is extended or adjusted under 35 U.S.C. 154(b) by 384 days.

(21) Appl. No.: 15/593,213

(22) Filed: May 11, 2017

(65) Prior Publication Data

US 2017/0241992 A1 Aug. 24, 2017

Related U.S. Application Data

(63) Continuation-in-part of application No. 14/169,320, filed on Jan. 31, 2014, now Pat. No. 10,099,156.

(30) Foreign Application Priority Data

Apr. 8, 2013 (EP) ..................................... 13162664

(51) Int. Cl.
| | | |
|---|---|---|
| *G01N 33/52* | (2006.01) | |
| *B01D 15/38* | (2006.01) | |
| *B01D 15/18* | (2006.01) | |
| *G01N 30/86* | (2006.01) | |
| *G01N 30/46* | (2006.01) | |

(52) U.S. Cl.
CPC ......... *G01N 33/52* (2013.01); *B01D 15/1807* (2013.01); *B01D 15/1864* (2013.01); *B01D 15/1871* (2013.01); *B01D 15/3804* (2013.01); *B01D 15/3809* (2013.01); *G01N 30/468* (2013.01); *G01N 30/8658* (2013.01)

(58) Field of Classification Search
CPC .. B01D 15/871; G01N 30/468; G01N 30/461; G01N 30/462
See application file for complete search history.

(56) References Cited

U.S. PATENT DOCUMENTS

| | | |
|---|---|---|
| 2,985,589 A | 5/1957 | Broughton et al. |
| 3,733,474 A | 5/1973 | Edwards et al. |
| 3,928,192 A | 12/1975 | Katzakian, Jr. et al. |
| 4,204,952 A | 5/1980 | Snyder |
| 4,215,563 A | 8/1980 | Clardy et al. |
| 4,274,967 A | 6/1981 | Snyder |
| 4,293,346 A | 10/1981 | Landis et al. |
| 4,434,051 A | 2/1984 | Golem |
| 4,447,329 A | 5/1984 | Broughton |
| 5,071,547 A | 12/1991 | Cazer et al. |
| 6,235,892 B1 | 5/2001 | Demmer et al. |
| 6,287,461 B1 | 9/2001 | Demmer et al. |
| 7,901,581 B2 | 3/2011 | Bryntesson et al. |
| 8,216,475 B2 | 7/2012 | valery et al. |
| 9,024,000 B2 * | 5/2015 | Jeon ......................... C07K 1/16 530/412 |
| 2010/0176058 A1 * | 7/2010 | Bryntesson ........ B01D 15/1828 210/659 |

FOREIGN PATENT DOCUMENTS

| | | |
|---|---|---|
| GB | 2 022 260 A | 12/1979 |
| WO | 2006/116886 A1 | 11/2006 |
| WO | 2008/127087 A1 | 10/2008 |
| WO | 2010/151214 A1 | 12/2010 |
| WO | 2013/083482 A1 | 6/2013 |

OTHER PUBLICATIONS

Search Report for EP 13 16 2664 dated Dec. 10, 2013.
Search Report for EP 13 16 2664 dated Sep. 3, 2013.
SZ. Nyiredy et al., "Stationary phase optimized selecivity liquid chromatography: Basic possibilities of serially connected columns using the "PRISMA" principle", Journal of Chromatography A, 2007, pp. 122-130, vol. 1157, No. 1-2.
Chapter 4 Chromatopgraphic Methods. NJIT. Accessed on Dec. 12, 2016 from https://web.mjit.edu/kebbekus/analysis/4CHROMAT.htm with a prior publication date of May 31, 2012 according to the Waybackmachine; archive.org.

* cited by examiner

*Primary Examiner* — Ryan B Huang
(74) *Attorney, Agent, or Firm* — Sughrue Mion, PLLC

(57) ABSTRACT

Provided is a method for control and/or monitoring and/or optimization of a chromatographic process, in which the method comprises at least 2 columns which are operated, alternatingly, wherein this operation can be carried out in that the at least 2 columns are operated in interconnected and disconnected states, wherein the columns switch positions after such a sequence of interconnected and disconnected state,
and wherein downstream of at least one, or of each column, a detector is located capable of detecting the desired product and/or impurities when passing the detector.

15 Claims, 13 Drawing Sheets
(9 of 13 Drawing Sheet(s) Filed in Color)

METHOD FOR CONTROL, MONITORING AND/OR OPTIMIZATION OF A CHROMATOGRAPHIC PROCESS

This application is a Continuation-in-Part of U.S. application Ser. No. 14/169,320, filed Jan. 31, 2014, which claims benefit of European Patent Application No. 13 162 664.0 filed Apr. 8, 2013; the entire contents of all of which are incorporated herein by reference in their entirety.

TECHNICAL FIELD

The present disclosure relates to a related method for control and/or monitoring and/or optimization of a chromatographic process. In addition, the present disclosure relates to methods of chromatographic purification, in particular using affinity chromatography, and in particular for capture chromatography, to methods for setting up such processes and to methods for the control of such processes.

PRIOR ART

Capture chromatography is used in the manufacturing of biopharmaceuticals, pharmaceuticals, nutraceuticals, chemicals and other products of interest as initial purification step following the upstream production. The main aim of capture chromatography is the concentration of the product with high throughput and high recovery/yield. In the ideal case a large impurity clearance is obtained simultaneously. For capture chromatography of biopharmaceuticals preferably columns packed with affinity chromatography stationary phases are used. Affinity materials offer a very high selectivity for the target molecules as they are based on immobilized ligands that bind specifically to the target molecules while letting impurities pass by unaffected. Due to the comparably high manufacturing costs of the affinity ligands, which are typically very elaborate, affinity materials are among the most expensive stationary phases available.

Traditionally, capture chromatography is run in single column, discontinuous mode which is characterized in that the column is consecutively (i) equilibrated, (ii) loaded with feed containing the target product, (iii) washed, (iv) eluted for recovering the desired target product, (vi) cleaned, and (i) re-equilibrated for the next run. The possible maximum load of the column with product is strongly dependent on the stationary phase capacity. A distinction has to be made between the static capacity, which corresponds to the occupancy of all ligands with target molecules obtained under equilibrium conditions (infinite contact time between ligands and target molecules), and the dynamic binding capacity under flow conditions (limited contact time between ligands and target molecules). The dynamic binding capacity depends among other factors on the linear flow rate and mass transfer properties.

Dynamic capacities are typically determined by measuring a so called breakthrough curve, i.e. the concentration curve over time or volume of the product of interest at the column outlet during continued load. In many cases the product concentration can be determined online at that outlet, typically by measuring UV light absorbance. In order to determine the completeness of the breakthrough (i.e. the load value where the outlet concentration reaches the feed concentration, also called saturation point) from the online detector signal it is useful to determine the feed signal as reference using the same detector in the absence of the column.

Depending on the abovementioned factors, the dynamic binding capacity is typically significantly lower than the static binding capacity. This entails that under flow conditions in single column chromatography, the stationary phase capacity is not fully and efficiently utilized since the loading has to be stopped far before the static capacity is reached in order to avoid product losses. On the one hand, the higher the linear loading flow rate is set, the higher the throughput becomes, but the lower the available dynamic binding capacity becomes, leading to early product breakthrough and lower effective stationary phase capacity utilization. On the other hand, the lower the linear flow rate is set, the higher the capacity utilization becomes but the lower the throughput.

Dual loading flow strategies for single column chromatography have been presented that represent a compromise between the two directions. These strategies comprise starting to load the column with a high flow rate in order to maintain high throughput, and then reducing the flow rate in order to obtain high capacity utilization and show advantages over the loading with a uniform flow rate.

Following the loading step, the column is washed, eluted and cleaned, even though the stationary phase has not been fully utilized. Since column cleaning is a major cause for stationary phase degradation the column packing has to be replaced after a certain number of cycles. Consequently, the stationary phase costs with respect to the amount of product produced are significantly larger under dynamic conditions than they would be if the full capacity of the stationary phase (i.e. the static binding capacity) was exploited.

In order to increase the stationary phase capacity utilization and increase the process productivity also the concept of continuous countercurrent chromatography has found application and a number of processes have been adapted from the chemical industry where the concept has been used for a longer time.

Most processes suggest the use of multiple identical columns that are loaded in sequence during the feed step. The motivation for this approach is that during the feeding step the parts of the column that are closer to the column inlet are in contact with higher product concentrations for a longer time and are therefore utilized better (i.e. they are closer to equilibrium corresponding to static conditions) than the parts of the column that are closer to the column outlet. Thus, when multiple short sequentially connected columns are loaded instead of a single long column the most upstream column which has the highest stationary phase utilization can be eluted and cleaned independently of the downstream columns that are loaded to a much lesser extent at the end of the loading step. Therefore only stationary phase with high capacity utilization is eluted and subsequently cleaned. While the fully loaded column is eluted and cleaned, the sequential loading progresses with the next column. Once the formerly upstream column has completed the elution and regeneration steps, it is coupled to the sequentially loaded columns at the most downstream position. Thus, by eluting only columns that have been loaded up to their static capacity, the product amount produced per stationary phase cycle is maximized.

Based on this principle, for the purification of therapeutic proteins from cell culture harvest, a number of multicolumn sequential loading processes have been described, among those processes with up to six columns. The application of simulated moving bed chromatography with eight columns for the capture of monoclonal antibodies from cell culture harvest using Protein A chromatography has even been described.

Sequential loading processes are not limited to continuous upstream manufacturing but may be likewise applied to batch-wise upstream manufacturing. In this case, process control is facilitated by the fact that most products are stable and that the product concentration in the feed is constant since the upstream process is completed before the start of the downstream purification process.

In continuous upstream manufacturing of biopharmaceuticals that is operated for a longer time period (days, weeks, months) a fluctuation of the feed concentration is typical, which demands appropriate process analytical tools and control strategies for the downstream sequential loading processes. Moreover the gradual decline of column capacity with the number of cycles requires the use of these tools and control strategies. Control strategies for controlling flow rates and durations of the chromatographic steps of other types of cyclically multicolumn continuous processes have been suggested based on peak retention times, inline analysis, and at-line analysis, respectively.

A control method for sequential loading processes based on continuously determining the binding capacity of each column in cyclic steady state has been described in WO2010/151214. The method comprises measuring a feed signal, representative of the composition of a feed material supplied to the inlet of the column, measuring an effluent signal representative of the composition of the effluent from the column, and using the feed signal and the effluent signal, to determine binding capacities from a so called "deltasignal". A major drawback of this method is that the feed signal is determined using a first detector and the effluent signal is determined using a second detector. Despite the detectors being of the same type, the detectors must be calibrated accurately and on a regular basis in order to derive useful information from the deltasignal such as breakthrough and saturation points that are ultimately used to derive control actions. The method requires the determination of a feed signal by a separate detector whose only purpose is the determination of the feed signal. The number of required detectors is therefore equal to the number of columns +1. The method cannot be used in cases the breakthrough curves cannot be accurately monitored, for instance due to a high impurity signal or due to a low product signal in the feed or both.

Continuous processes and their control align perfectly with the ongoing initiatives of health administrations, which strongly encourage the development and use of process analytical tools for understanding and controlling pharmaceuticals production.

SUMMARY OF THE INVENTION

The present disclosure relates to for control and/or monitoring and/or optimization of a chromatographic process.

In addition, the present invention relates to countercurrent chromatography processes as well as methods for design, setup, control and optimization of sequential countercurrent loading chromatography processes.

It was surprisingly found that by an innovative combination of the advantages of the sequential loading chromatography, reducing the number of columns to two, applying a dual loading flow strategy and, if needed, applying a process control strategy using the same detector to record the relevant signals for the control, a novel process including design and control methods could be developed exhibiting excellent productivity and capacity utilization performance. The twin-column sequential loading process requires significantly less hardware (valves, detectors, fluid connections, columns) than sequential loading processes with three or more columns.

The control method is not only applicable to methods involving only two columns, but is also and equivalently applicable to twin-, three- and multicolumn countercurrent capture processes where at least two columns are loaded sequentially (connected in series) in one phase of the cyclic process and at least one column is loaded in a second phase of the process. So the control method is to be seen in the context of the above two column process, but also, and quite independently, also in the context of other countercurrent processes with two or more columns. The described control methods require for each chromatographic column a detector to be mounted such that it is capable of recording a signal at the outlet of the column corresponding to the column effluent.

Chromatographic Capture Method:

As a first aspect of the invention, a method of chromatographic purification is proposed using a countercurrent sequential loading chromatography process as schematically illustrated in FIG. 1 with two chromatographic columns only. In FIG. 1, interconnected phases are denoted with IC, disconnected (batch) phases are denoted with B. Interconnected phase means a step where the columns are in a serial connection, i.e. the outlet of an upstream column is connected to the inlet of a downstream column. Disconnected (batch) phase means a step where the columns are not connected but individually loaded with feed or just with solvent via their inlets and their outlets are directed to waste or product collection. A cycle of the process comprises two switches, wherein each switch in turn comprises one B phase and one IC phase. During the B phase of the first switch, column 1 is loaded with feed while column 2 is eluted (product recovery) and regenerated, with regeneration including, if needed, preloading with feed as detailed below.

During the loading of column 1 the flow rate can be kept constant or, according to a preferred embodiment, it is possible to start with a high flow rate and according to a desired profile to reduce the flow rate towards the end of the loading of column 1 in this step (e.g. by using a hyperbolic profile). Or it is possible, in a first phase of this loading, to have a high flow rate, and in a second final phase, a lower flow rate (single or multiple step function). It is possible to use (loading) flow rates that are approximately at most 2-fold larger than the maximum loading flow rate of the interconnected phase since the columns are operated in disconnected mode, which reduces the chromatographic bed height and thereby the back-pressure by approximately a factor of 2 compared to the interconnected phase. This allows for either a fast loading (column 1), or a fast recovery and regeneration (column 2) or both. Also an efficient initial phase and a slow final phase of the loading process with improved chromatographic mass transfer, leading to an optimum product profile in the column in an optimum amount of time, can be obtained.

The product recovery and regeneration phase with column 2 implies the elution of the desired product (recovery) and preparation of the column for the next step (regeneration). Specifically, this recovery and regeneration phase includes normally the sequence of the following steps:

(i) washing with solvent and/or buffer under conditions that the product is not released from the stationary phase (this washing may include several steps with different conditions, e.g. with varying pH, ionic strength, solvent/buffer composition, etc; indicated in FIG. 1 with "wash"), (ii) elution with solvent and/or buffer under conditions that the product is released from the stationary phase (i.e. by a change of pH, a change of solvent or solvent composition, etc; also this step may include several steps with different conditions, indicated in FIG. 1 with "elu"), (iii) cleaning in place (CIP) using an appropriate solvent and/or buffer to release everything from the stationary phase, optionally followed by sanitisation (again these steps may include several phases with several different conditions, e.g. with varying pH, ionic strength, solvent/buffer composition, etc)

(iv) equilibration, typically by using the solvent and/or buffer under conditions similar or the same as in the subsequent process step, where again several steps with different conditions can be used to bring the column into equilibrium as efficiently as possible (indicated in FIG. 1 with "equi").

During this product recovery and regeneration phase of column 2, the flow rate can be increased as compared to the flow rate of the columns in the interconnected phase. This is possible up to a factor of approximately 2 since the columns are operated in a disconnected mode, which reduces the chromatographic bed height and thereby the back-pressure by approximately a factor of 2, as compared to the interconnected phase. The flow rate increase in the recovery and regeneration step is generally not critical to the quality of separation, while for an optimum distribution in column 1 the loading flow rate in that column needs to be maintained at a well-defined level or profile as described above.

What is also possible in view of the above is that the recovery and regeneration of column 2 includes a preloading with feed. In the context of this application therefore the regeneration phase of column 2 may also include, after at least one of the steps of cleaning, and/or equilibration, a final step of feeding with feed so as to preload column 2. This is possible since the steps of washing, elution, cleaning, and/or equilibration, as mentioned above, can be carried out at a high flow rate and rather quickly, and in order to avoid idle time of column 2 and in order to have an as high as possible throughput, preloading of column 2 may be included into this regeneration step. Therefore the term regeneration of the column, in the context of this invention, may also include a terminal step of preloading of the corresponding column with feed. This holds true for the first switch as well as for the second switch, so in the second switch column 1 can be preloaded in the batch step in the regeneration phase.

During the subsequent IC phase of the first switch, column 1 and column 2 are loaded and preferably also washed in series, with column 1 in the upstream position and column 2 in the downstream position.

During the subsequent B phase of the second switch, column 2 is loaded while column 1 is eluted (product recovery) and regenerated.

During the IC phase of the second switch, column 2 and column 1 are loaded and preferably also washed in series, with column 2 in the upstream position and column 1 in the downstream position.

The cycle is repeated multiple times, which is indicated by the visual encapsulation of the flow sheets of one cycle with dashed lines in FIG. 1. In the shutdown phase, following the last cycle, both columns are eluted as in the B phase for final product recovery. Detectors are located at the outlet of each column, one detector D1 at the outlet of column 1 and one detector D2 at the outlet of column 2. The detectors can e.g. be UV detectors.

A cycle of the chromatographic process is defined as the sequence of tasks that each of the columns needs to fulfill before reaching its starting task again. Thus, a complete cycle of the twin column process comprises two switches, each switch comprising a disconnected phase and an interconnected phase.

Cyclic steady state is defined as a state in which the average amount of material withdrawn through the product outlet is constant from cycle to cycle. Typically a cyclically continuous process needs to be operated over a number of cycles (2-10 cycles) before reaching cyclic steady state.

In addition to the cyclic phase the process may include additional phases that improve the process performance in terms of throughput and product output. The additional phases include:

A startup phase, which is only carried out once as the process is started wherein the columns are interconnected as in the interconnected phase but a larger amount of feed solution is loaded so that the process reaches cyclic steady state faster. The larger amount of feed compensates for the columns being not preloaded and devoid of product at process start. When using a startup phase, the twin column sequential loading process is in cyclic steady state in the 2nd cycle.

A shutdown phase wherein the two columns are disconnected, no new feed is loaded and the columns perform the remaining tasks of a chromatographic cycle (i.e. typically the above steps (i)-(iv)) including the elution in parallel or sequentially in order to recover the entire product that is present in the columns.

Washing phases wherein the columns are interconnected and washing solution is flushed through both columns in order to adsorb the product that is present in the interstitial liquid of the upstream column which is the next one to be eluted.

The process is preferably operated with a lower flow rate in the disconnected than in the interconnected state in order to improve the dynamic binding capacity and to obtain high capacity utilization. Generally the duration of the disconnected state is relatively large, preventing the use of the loading flow rate of the interconnected state also in the disconnected state, since breakthrough in the disconnected state would be likely to occur. When applied to continuous upstream production, the different feed flow rates of the interconnected and disconnected phases of the twin column sequential loading process require a connection of the process to a balancing container matched to the average feed flow rate.

Generally speaking, therefore, the first aspect of the present invention relates to a purification method for the isolation of a desired product fraction from a mixture using only 2 chromatographic columns. The method comprises, within one cycle to be carried out at least once, if needed several times, preferably essentially continuously, the following steps:

a first batch step B1, wherein during a batch timespan $t_B$ said columns are disconnected and a first column is loaded with feed via its inlet using a first flow rate $Q_{feed,B}$ and its outlet is directed to waste, and from a second column thereof desired product is recovered via its outlet and subsequently the second column is regenerated (this is the situation in the continuous process. If this step is carried out for the first time, the second column is either idle or preceding the first step B1 an interconnected start-up step is carried out in which the first and/or the second column are loaded with feed, as e.g. illustrated in FIG. 1 on top of the page).

As mentioned above, during this product recovery and regeneration phase with the second column, the flow rate can be increased compared to the parallel operating first column. This is possible up to a factor of 2, so the flow rate in the second column during this phase can be twice as high as the flow rate in the interconnected phase. What is also possible in view of the above is that the recovery of second column includes a preloading with feed. In the context of this application therefore the regeneration phase of the second column may also include, after at least one of the steps of cleaning and equilibration, a final step of loading with feed so as to preload the second column. As mentioned above, therefore, the term "regeneration" of the column, in the context of this invention, may also include a terminal step of preloading of the corresponding column with feed. This holds true for the first switch as well as for the second switch.

As concerns the loading of the column, as mentioned above, the flow rate can be kept constant or, according to a preferred embodiment, it is possible to start with a high flow rate and, according to a desired profile, reduce the flow rate towards the end of the loading of the first column in this step. Or it is possible, in a first phase of this loading of the first column, to have a high flow rate, and in a second final phase, a lower flow rate (step function).

The foregoing loading is followed by a first interconnected step IC1, wherein the outlet of the first column is connected to the inlet of the second column during an interconnected timespan $t_{IC}$, wherein the first column is loaded beyond its dynamic breakthrough capacity with feed via its inlet using a second flow rate $Q_{feed,IC}$ which is the same or larger than the first flow rate $Q_{feed,B}$, and the outlet of the second column is directed to waste.

In this interconnected step it is possible to have a subsequent washing step in order to make sure that in the upstream column solvent and/or buffer carrying non-adsorbed product is not washed out to waste in the initial phase of the subsequent batch step but is washed and adsorbed either in the remaining free capacity of the upstream column or of the downstream column. Correspondingly, during a subsequent washing timespan ($t_{wash,IC}$) which is larger or equal to 0 s in this interconnected step, it is possible to carry out washing such that the outlet of the first column is connected to the inlet of the second column, the first column is loaded with solvent and/or buffer which is free from feed material, and the outlet of the second column is directed to waste.

This first batch step B1 and interconnected step IC1 are followed by essentially analogous steps but with the positions of the columns exchanged, i.e. the first column of the above first batch step and first interconnected step switches position to become the second column, and the second column of the above first batch step and first interconnected step switches position to become the first column. In other words, the above first batch step and first interconnected step are followed by a second batch step B2 analogous to the first batch step B1 but with exchanged columns, such that the first column 1 of the first batch step B1 is the second column 1 of the second batch step B2 and the second column of the first batch step B1 is the first column of the second batch step B2 Then this is followed by a second interconnected step IC2 analogous to the first interconnected step IC1 but with exchanged columns, such that the upstream column of the first interconnected step IC1 is the downstream column of the second interconnected step IC2 and the downstream column of the first interconnected step IC1 is the upstream column of the second interconnected step IC2.

The batch timespan $t_B$ is, according to a preferred embodiment, chosen to be the accumulated time required for the recovery and regeneration of the respective column. Preferentially, this accumulated time is given by the accumulated time required for the steps of: (i) washing with solvent and/or buffer under conditions that the product is not released from the stationary phase; (ii) elution with solvent under conditions that the product is released from the stationary phase (e.g. by running a gradient, this step may include outlet fractionation); (iii) cleaning in place using a solvent and/or buffer to release everything from the stationary phase; and (iv) equilibration, preferably by using the solvent and/or buffer under conditions similar or the same as in the subsequent process steps. It was found that normally the rate limiting element of the batch step is actually the recovery and regeneration of the product from the respective column. This is what takes a rather long time. It was further unexpectedly found out that an enormous increase in throughput can be obtained if, during the batch step, the flow rate of the other column which is not subject to recovery and regeneration, i.e. of the column which is being loaded with feed, is adapted to be as low as possible but just high enough to preload the column as much as possible within the timeframe available. According to a first preferred embodiment, therefore, in the interconnected step IC (i.e. in the first and/or the second interconnected step) the second flow rate $Q_{feed,IC}$ is adapted to be larger than the first flow rate $Q_{feed,B}$. Preferably the second flow rate $Q_{feed,IC}$ is at least 10% larger, more preferably at least 25% larger, most preferably 1-10 times larger (optimally 1.5-2.5 times larger) than the first flow rate $Q_{feed,B}$. As will be detailed further below, the values are adapted by setting the second flow rate to an as high as possible value for the interconnected situation, and by choosing an appropriately optimised low value for the first flow rate, which is typically in the range of 10-90% (optimally 50-90%) of the second flow rate.

As pointed out above, one key element of the proposed process is the fact that the capacity utilization of the upstream column in the interconnected phase is maximized by loading the upstream column beyond its breakthrough point (the breakthrough point corresponds to the point where product starts to elute from the upstream column during loading) so that the downstream column takes up already a certain fraction of product and is preloaded. To be more specifically in this respect, and to achieve this running of the interconnected phase beyond the breakthrough point, the parameters can, according to a preferred embodiment, be adapted as follows: in the interconnected step IC the second flow rate $Q_{feed,IC}$ and/or the interconnected timespan $t_{IC}$ can be chosen such that at the end of interconnected timespan $t_{IC}$ the feed concentration at the outlet of the upstream column is in the range of 30-90% (breakthrough value X) of the feed concentration at the inlet of the upstream column. Depending on the profile this condition can however be a problem in a situation where by taking this criterion product already elutes at the outlet of the downstream column. Therefore the above should preferably be taken with the proviso that the values of the second flow rate $Q_{feed,IC}$ and/or the interconnected timespan $t_{IC}$ are adapted such that at the end of the interconnected timespan $t_{IC}$ at the outlet of the downstream column the product concentration is below a breakthrough value of 0.25-5%, preferably of 1-2.5%, and that the elution volume value corresponding to this breakthrough value is preferably multiplied by a safety factor in the range of 60-90%. The target is to have an as high as possible value of $Q_{feed,IC}$, which is possible by taking the smaller of $EV_{1H,X}$ and $EV_Y$, where X is the desired breakthrough value of the upstream column, see further details given below.

According to yet another preferred embodiment, the disconnected phase may comprise a simple cleaning of one of the columns and a more thorough cleaning of the columns may be carried out in prolonged disconnected phases regularly every m cycles, wherein m is larger or equal to two.

According to yet another preferred embodiment, the columns are affinity chromatography material loaded columns, wherein the chromatographic stationary phase can be in the form of particles, such as beads, and/or membranes and/or monoliths.

For the control and monitoring of the corresponding process, but also for setting it up as will all be further detailed below, at the outlet of each column a detector for the analysis of the components at the outlet can be located, wherein preferably both detectors are of the same type. This can be any kind of detector suitable to detect the desired product, and it should be adapted such that at least for the desired product under the chosen operating conditions it is not reaching detection saturation, such that quantitative detection is possible. These detectors can e.g. be detectors selected from one or a combination of the following detectors: UV detector, visible light detector, IR detector, fluorescence detector, light scattering detector, refractive index detector, pH detector, Raman detector, or conductivity detector.

As pointed out above, these cycles, in case of continuous feed, can be carried out continuously and repeatedly until e.g. exchange of column material is necessary or until the feed flow is interrupted necessitating a stop.

However for setting up the process, it is, according to a preferred embodiment, advisable to start with a startup step preceding the first cycle, in which the columns are interconnected and wherein a larger amount of feed solution is loaded onto the upstream column in comparison with an interconnected step IC of a cycle of the method. Indeed in such a start-up step the upstream column is not, as in continuous operation, already preloaded due to a preceding batch step, so in this start-up step the upstream column has a higher effective capacity which can then be filled up to enter the first cycle. The corresponding time is adapted and set up is detailed further below.

If the process has to be stopped, according to yet another preferred embodiment the last cycle can be followed by a shutdown step, in which the two columns are disconnected, and both columns are subjected to product recovery and column regeneration.

Preferentially, the desired product is one or a group of antibodies, antibody fragments, fusion proteins, recombinant glycoproteins, and/or plasma proteins or combination thereof. The process generally speaking thus operates in a cyclic manner wherein one cycle comprises the following alternating phases:

a first batch phase B1 wherein the columns are disconnected and the column that has been the downstream column in the preceding interconnected phase is continued to be loaded using a first feed flow rate, which is the same or lower than a second feed flow rate in an interconnected step, and wherein the column that has been the upstream column in the preceding interconnected phase performs the tasks of a typical chromatographic cycle that follow the feeding step (such as washing, elution, cleaning, re-equilibration); and a first interconnected phase IC1 wherein first feed solution and normally thereafter wash solution is loaded onto the preloaded column and the columns are interconnected so that the stream exiting the preloaded upstream column enters the downstream column;

a second batch phase B2 wherein the columns are disconnected and the column that has been the downstream column in the preceding interconnected phase IC1 is continued to be loaded, at a lower flow rate than in the interconnected step, and wherein the column that has been the upstream column in the preceding interconnected phase IC1 performs the tasks of a typical chromatographic cycle that follow the feeding step (such as washing, elution, cleaning, re-equilibration), and wherein the column that is continued to be loaded is positioned upstream in the subsequent interconnected phase IC2; and a second interconnected phase IC2 wherein the columns are interconnected in the opposite order as in the preceding interconnected step IC1 and first feed solution and optionally thereafter wash solution is loaded onto one of the columns and the columns are interconnected so that the stream exiting the upstream column enters the downstream column.

Setup Method:

For the setting up of the process as outlined above the duration t and the flow rate Q have to be determined for each of the batch B and the interconnected IC step.

As pointed out above, the rate determining steps within the batch step are generally the recovery and regeneration steps of the column which is not loaded with feed. The time required for these steps will determine the duration $t_B$ of the disconnected state. As also pointed out above, during the time available in the batch step the column which is loaded with feed should be supplied with an as low as possible feed rate for optimum capacity utilization taking however also into account that at the end of the disconnected step the corresponding column should be filled up with product optimally, so just to the extent that there is no or essentially no breakthrough of the product. To determine the corresponding feed flow rate $Q_{feed,B}$ it is however not sufficient to just determine the breakthrough curve of the single column since this would not take into account the fact that this column has already been preloaded in the preceding interconnected step when it was the downstream column. Therefore the batch step feed rate needs to take into account to which extent the column has already been filled up with feed in the preceding interconnected step.

On the other hand in the interconnected step, for efficiency reasons, the feed rate $Q_{feed,IC}$ should be as high as possible, and is typically chosen to be at the upper end of the feed rates specified for the corresponding columns in interconnected state. The challenging task in the determination of the parameters for the interconnected state is therefore not the flow rate but the duration $t_{IC}$ of this step. The duration should be chosen such that the capacity of the upstream column is filled up beyond its breakthrough point to the desired extent (typically expressed as a concentration of desired product at the outlet of the upstream column relative to the feed concentration at the inlet, this ratio is normally chosen in the range of 30-90%), but at the same time it must be made sure, in particular in case of a shallow breakthrough profile, that at the moment when reaching this breakthrough of the upstream column no product is already eluting at the outlet of the downstream column.

Therefore the setting up of an optimum parameterization of the process is far from trivial and in the following a protocol shall be given for finding such parameterization in a systematic manner.

More specifically therefore, the invention also relates to a method for setting up a chromatographic method as outlined above, wherein the batch step duration $t_B$ of the batch step B is set to be the accumulated time required for recovery and regeneration of the respective column, and the batch step feed flow rate $Q_{feed,B}$ applied to the respective column in the batch step B is set such that at the end of the batch step duration $t_B$ at the outlet of the column there is essentially no desired product elution, taking into account that in the preceding step this column has already been preloaded. The interconnected step feed flow rate $Q_{feed,IC}$ on the other hand is set to a desired value and the interconnected step duration $t_{IC}$ is set such that at the end of the interconnected step duration $t_{IC}$ at the outlet of the upstream column the desired product concentration is in desired range, preferably in the range of 30-90%, of the concentration at its inlet, with the proviso that there is essentially no desired product elution at the outlet of the downstream column.

For the determination of the batch step feed flow rate $Q_{feed,B}$ and the interconnected step duration $t_{IC}$ preferably at least one breakthrough curve (or a series of breakthrough curves) of a single column using the interconnected step feed flow rate $Q_{feed,IC}$ is recorded (e.g. using fractionation and analysis) and used. If needed, in particular in case of very shallow breakthrough profiles with the risk of product elution at the outlet of the downstream column in the interconnected step, further at least one breakthrough curve of interconnected columns using the interconnected step feed flow rate $Q_{feed,IC}$ can be recorded and used. Furthermore at least one breakthrough curve (or a series of breakthrough curves) of a single column using a lower batch step feed flow rate $Q_{feed,B}$ than the interconnected step feed flow rate $Q_{feed,IC}$ is recorded and used for the determination of the parameters, wherein preferably the lower batch step feed flow rate $Q_{feed,B}$ for the determination of this breakthrough curve is chosen to be 50-90% of the interconnected step feed flow rate $Q_{feed,IC}$.

For the twin column process, generally speaking, the following operating parameters have to be determined prior to running the process:

$t_{IC}$ (interconnected state duration), $t_{IC,wash}$ (interconnected state wash duration, optional), $t_B$ (disconnected state duration), $t_{startup}$ (startup step duration, optional), $Q_{feed,IC}$ (interconnected phase feed flow rate), $Q_{feed,B}$ (disconnected phase feed flow rate), $Q_{feed,startup}$ (startup state feed flow rate, optional), disconnected state elution parameters, and final elution parameters.

The disconnected state elution parameters relate to single column chromatography and include the number, duration and flow rates of the washing, elution, stripping, cleaning, sanitization, and re-equilibration steps that are applied to the loaded column in order to recover the product and to prepare the column for the uptake of new product. The disconnected state elution parameters are determined usually by a screening approach based on the purity requirements and/or on individual standard guidelines in the chromatographers institution and are therefore not a part of the parameter determination procedure described in the following. The total duration of the disconnected state procedure is referred to as $t_B$ in the following.

The same holds true for the final elution parameters of the sequential loading column process where product is recovered from the two columns individually (see FIG. 1).

The startup step is optional, but it is advantageous since it shortens the time the process requires to reach steady state.

For the determination of the operating parameters $t_{IC}$ and $t_{startup}$ the recording of breakthrough curves is required which preferably are fractionated and analyzed by offline analysis. However, if the evaluation of the breakthrough curves is carried out based on the chromatograms only and not on the offline fraction analyses, in addition a calibration of the breakthrough signals with the feed signal recorded by the respective detector has to be carried out, preferably determined in the absence of the columns.

In summary, the design method comprises the following elements:

experimentally determining an elution volume $EV_2$, corresponding to a breakthrough value multiplied with a safety factor for two sequentially interconnected columns at the desired maximum loading flow rate, running a breakthrough curve for a single column at the desired maximum flow rate and determining the elution volume $EV_{1H,1}$, corresponding to a low breakthrough value, determining the elution volume $EV_{1H,X}$, from the single column breakthrough curve at high flow, corresponding to a high breakthrough value X for a single column at the desired maximum flow rate (X is preferably 30-90%), running a second breakthrough curve for a single column at the flow rate significantly lower than the desired maximum flow rate and determining the elution volume $EV_{1L,1}$, corresponding to a low breakthrough value, determining the value $EV_Y$, which is equivalent to the smaller one of the two values $EV_{1H,X}$ and $EV_2$, determining a preload value PL that corresponds to the amount of product present in the downstream column when the feed volume of $EV_Y$ has been loaded onto the two columns in series. This value is computed from the breakthrough curve of a single column by means of integration with $EV_Y$ as upper boundary, determining a target load value TL that corresponds to the amount of product that can be loaded additionally onto the preloaded column in the disconnected phase B. This value is computed from $EV_{1L,1}$ and PL, determining the interconnected state switch time $t_{IC}$ using $EV_{1L,1}$ and $EV_Y$. The calculation takes into account that the upstream column is preloaded when entering the interconnected state and that the downstream column needs to be continued to be loaded with feed in the subsequent disconnected state, optionally determining the startup time $t_{startup}$ from $t_{IC}$ and $EV_{1L,1}$, selecting $Q_{feed,IC}$ and $Q_{feed,startup}$ the same as the flow rate used to record the breakthrough curve of the two interconnected columns, determining the duration of the disconnected phase B, $t_B$, by summing up the durations of the times required for the different steps of washing, elution, cleaning, equilibration, calculating the feed flow rate of the disconnected state using the values of TL and $t_B$, comparing it to the low flow rate used to determine the second breakthrough curve, and selecting the smaller value as $Q_{feed,B}$, and determining the duration and flow rate of the wash step $t_{wash,IC}$ that follows the loading step in the interconnected state using the values $Q_{feed,IC}$ and $V_{dead}$.

More details on the calculations are laid down in the preferred embodiments further below. A software can be used to automatically carry out the setup steps described above and in the following.

The measurement range of the detector should be adapted once before starting the method in order to enable the detector to measure at least the elution peak area and preferably the breakthrough area in the linear range of the detector (this not only applies to the setup but also to the control as further outlined below). For instance for a UV detector used in protein chromatography, if the determination of absorption at 280 nm wavelength is in the non-linear range of the detector, the wavelength may be changed to e.g. 300 nm wavelength which is most likely in the linear range of the detector for the typical protein concentrations encountered in protein chromatography.

The design method is also applicable in case of a large impurity signal where the detectors are in the non-linear range. In this case offline analyses must be used to evaluate the breakthrough curves.

The initial operating parameters of the twin-column sequential countercurrent loading chromatography process, $t_{IC}$, $t_B$, $t_{startup}$, $t_{wash,IC}$, $Q_{feed,IC}$, $Q_{wash,IC}$, $Q_{feed,B}$, $Q_{feed,startup}$ that may serve also as starting point for control and optimization methods are, now in more detail, determined by the following procedure:

(a) calculation of the duration of the disconnected state $t_B$ by summing up of the durations of the single steps carried out with the column which is not fed with feed following the protocol of the chromatographic cycle including typically washing, elution, cleaning, optionally sanitization, and re-equilibration steps (see also above).

(b) determination of the elution volume breakthrough value $EV_2$ of two interconnected columns using the desired maximum feed flow rate $Q_{feed,IC}$ of the interconnected state. The flow rates $Q_{feed,IC}$ and $Q_{feed,startup}$, respectively, correspond to this maximum flow rate, and this is usually determined using a high-end value and provided for by the specification of the producer of the column material or equipment. More precisely this step (b) comprises the determination of the elution volume EV corresponding to a certain breakthrough value for instance 1% breakthrough up to 5% breakthrough with respect to the feed concentration, and multiplying this elution volume EV with a safety factor Z between 60% and 90% (both dependent on the specific conditions and targets, e.g. using values that are also used for single column chromatography). The breakthrough elution volume value, multiplied by Z, is designated $EV_2$. $EV_2$ (index 2 for two interconnected columns) is determined by evaluation of the dynamic breakthrough curve of two sequential columns ($DBC_2$), i.e. by using the chromatogram or by fractionation of the flow-through during load and by offline fraction analysis. Basically this measurement is carried out to find out at which elution volume in the interconnected state product starts to elute at the outlet of the downstream column. This is to make sure that the interconnected step duration is not chosen longer than what is possible in view of this breakthrough elution profile.

(c) determination of the elution volume breakthrough value $EV_{1H,1}$ (first index 1 stands for single column, H stands for high flow rate, and second index 1 for 1% breakthrough threshold) of a single column using the previously chosen feed flow rate $Q_{feed,IC}$, and recording the full breakthrough curve $DBC_1$ (dynamic breakthrough curve with one single column). The elution volume corresponding to a certain low breakthrough value of the single column, preferably 1% breakthrough with respect to the feed concentration is determined from the full breakthrough curve. This low breakthrough value elution volume of the single column is designated $EV_{1H,1}$. The breakthrough value is determined by evaluation of the chromatogram or by fractionation of the flow through during load and by offline fraction analysis. The determination of $EV_{1H,1}$ is not mandatory, however for the purpose of limited integration in step (f) it is advantageous to have this value available.

(d) determination, from the breakthrough curve determined in step (c), of the X % breakthrough elution volume $EV_{1H,1}$ corresponding to a high load of the single column. X is typically a number between 30 and 90%. This elution volume value is designated $EV_{1H,1}$. The aim of this is to determine the moment at which the interconnected phase needs to be terminated. However the value determined here as it stands does not take into account that the upstream column has already been preloaded in the preceding step, and it also does not take into account that it has to be prevented that product elutes at the outlet of the downstream column during the interconnected phase. For preventing the latter the condition in step (e) is applied.

(e) Determination of the smaller one of the two value $EV_2$ and $EV_{1H,X}$. This value is designated $EV_Y$. The purpose of this condition is to make sure that no product elutes at the outlet of the downstream column during the interconnected phase.

(f) determination of the preload value PL, calculated by integrating the difference of the calibrated breakthrough curve $DBC_1$ of the single column (as determined in above (c)) and the calibrated breakthrough curve $DBC_2$ of the interconnected columns (as determined in above (b)) with the upper boundary of $EV_Y$, divided by the column volume of the single column according to equation 1:

$$PL = \frac{1}{V_{col}} \cdot \int_{EV_{1H,1}}^{EV_Y} DBC_{1H}(EV) - DBC_2(EV) dEV, \quad \text{(equation 1)}$$

$$EV_Y = \min\{EV_{1H,X}; EV_2\}$$

It is also possible to use zero as lower starting point for the integration.

In this step in other words the product mass per column volume is calculated by which the downstream column is already preloaded due to what happens in the interconnected step, which in turn is necessary for determining how much capacity is left for loading in the batch step.

(g) determination of a second breakthrough value $EV_{1L,1}$ of a single column using a lower flow rate $Q_{feed,BT1L}$ than for the previous single column breakthrough determination. Typically $Q_{feed,BT1L} = W\% \cdot Q_{feed,IC}$, with W=50-90%: Recording the full breakthrough curve $DBC_{1L}$ at least until $EV_Y$ and determination of the elution volume corresponding to a certain low breakthrough value, preferably 1% breakthrough with respect to the feed concentration (the same % value as in the determination of the single column breakthrough value at the higher flow rate can be chosen). This elution volume is designated $EV_{1L,1}$, wherein the breakthrough value is determined from $DBC_{1L}$ by evaluation of the chromatogram or by fractionation of the flow through during load and by offline fraction analysis. This value, indicating by how much the column is already charged with desired product at the end of the batch step, now allows the determination of the possible duration of the interconnected step in (h).

(h) determination of the interconnected state switch time $t_{IC}$ by subtracting Z %·$EV_{1L,1}$, from $EV_Y$ and dividing the complete term by the feed flow rate $Q_{feed,IC}$ in the interconnected state (i.e. the feed flow rate that was used to record the breakthrough curves $DBC_2$ of the two sequential columns in step (b)), according to equation 2:

$$t_{IC} = (EV_Y - Z\% \cdot EV_{1L,1})/Q_{feed,IC} \quad \text{(equation 2)}$$

(i) determination of the target load value TL, from the preload value PL and the breakthrough curve $DBC_{1L}$ of the single columns by subtracting the dead volume from the elution volume corresponding to 1% breakthrough of the value $EV_{1L,1}$, multiplied with the safety factor Z, and multiplying the difference with the feed concentration value, dividing said product by the column volume and subtracting PL from this value, according to equation 3:

$$TL = ((Z\% \cdot EV_{1L,1} - V_{dead}) \cdot c_{feed})/V_{col} - PL \quad \text{(equation 3)}$$

This value thus represents the actually available capacity of the column during the batch step feed loading, i.e. the available capacity taking the preload during the interconnected step into account. This value now allows the determination of the feed flow rate in the batch state in the following step (j).

(j) determination of the feed flow rate of the disconnected state, $Q_{feed,B}$, according to equation 4 by multiplying TL with the column volume, dividing by the feed concentration, and dividing by the duration of the disconnected state, $t_B$, which is determined by the protocol for the chromatographic cycle which comprises washing, elution, cleaning and re-equilibration steps, and optionally further steps of sanitization.

$$Q_{feed,B} = (TL \cdot V_{col})/(c_{feed} \cdot t_B) \quad \text{(equation 4)}$$

If the flow rate $Q_{feed,B}$ determined by this calculation is larger than the flow rate that was used to record the single column breakthrough curve at the lower flow rate, the latter flow rate should be used as $Q_{feed,B}$, i.e $Q_{feed,B} = Q_{feed,BT1L}$.

(k) optional determination of the startup time t by dividing the difference of $Z\% \cdot EV_{1L,1}$ and $V_{dead}$ by the feed flow rate $Q_{feed,IC}$ and adding this value to $t_{IC}$, according to equation 5. The flow rate during startup is the same as the feed flow rate in the interconnected phase.

An interconnected state startup step is optional but it can be used to reach the cyclic steady state faster.

$$t_{startup} = t_{IC} + (Z\% \cdot EV_{1L,1} - V_{dead})/Q_{feed,IC} = (EV_Y - V_{dead})/Q_{feed,IC} \quad \text{(equation 5)}$$

(l) determination of the duration of the interconnected state washing step $t_{wash,IC}$ that follows the interconnected phase loading step by dividing the dead volume by the flow rate $Q_{wash,IC}$, which is of the same value as $Q_{feed,IC}$ but uses washing buffer instead of feed (equation 6):

$$t_{wash,IC} = k \cdot V_{dead}/Q_{wash,IC} \quad \text{(equation 6)}$$

with k as rational number $\geq 1$.

In the above equations, the dead volume $V_{dead}$ corresponds to the elution volume of a non-absorbing component from the point of feed to the point of detection (including one column). It can be determined either by tracer experiments, or by evaluating the impurity signals recorded by the two UV detectors in the sequential loading of two columns.

The above method can be used also to determine the operating parameters for a k-column sequential loading process with k>2 with the difference that the disconnected state tasks that typically include washing, elution, cleaning, sanitization, and re-equilibration steps are distributed among more than one phase (as in the case of the twin column process).

Control, Monitoring and Optimization Method:

The invention further, and also independently of the above two column process and of the corresponding setup procedure, relates to a method to be used for chromatographic sequential loading process monitoring optionally with detector comparison. The control and monitoring method requires there to be at least 2 columns which are operated, alternatingly, preferably in interconnected and disconnected state, and switch positions after such a sequence of interconnected and disconnected state. Furthermore the control and monitoring method requires that a detector is located downstream preferably of each column capable of detecting the desired product when it passes the detector. Preferably the detector should be adapted to be operating in a quantitative regime during all phases of the process, i.e. when faced with undesired impurities but also when faced with desired product.

The gist of the control and monitoring method is to compensate for differences in the detectors present by using the repetitious cycle of interconnected and disconnected state and to exploit the fact that the two columns and therefore also the detectors alternatingly take over the same function. By comparing the results of the detectors associated with the columns at situations where they should actually show identical results due to the identical function of the associated column, control is possible in particular by calculation of the corresponding ratio between the two detector results in this situation and checking whether the same ratio is true for different positions in the process where also the same ratio should result. Control is also possible by monitoring and evaluation the signal recorded by a single detector utilizing the knowledge that each detector provides certain signals that should be the same from cycle to cycle, therefore providing control set points.

It should be noted in this respect that so far control and monitoring of these processes has only taken place in the past by checking either whether there is any product at the outlet during product elution (simple yes/no detection but not quantitative) or by comparing the inlet with the outlet of single columns using two detectors at these positions, which however inherently poses the problem of calibration of these two detectors. All this is avoided by the proposed simple and straightforward process.

The monitoring and control method for a chromatographic multicolumn sequential loading process with at least two columns preferably comprises at least the steps of determining online at least the area below the breakthrough curve of a product of interest, '$A_{CiU}$' (measured by detector i). It may also or alternatively include evaluating the elution peak signal '$A_{peaki}$' (measured by detector i) of a single cycle, corresponding to the product of interest, recorded by detectors located at the outlet of each column, evaluating the signal by means of suitable algorithms and deriving control actions therefrom, or a combination of evaluation of the area below the breakthrough curve '$A_{CiU}$' and evaluation of the elution peak signal '$A_{peaki}$'.

The detector signals should be quantitatively representative of product mass and/or concentration.

The nomenclature used in the following method descriptions and preferred embodiments, relates, without loss of generality to the areas measured by UV detectors, and is explained in the following:

The peak area $A_{peaki}$ is defined as the area confined by the elution peak curve and a horizontal baseline corresponding to the value of the equilibrated empty column (see FIG. 2 and FIG. 5) or a baseline defined by other criteria such as points of operating parameter changes (e.g. end of the washing step, start of the cleaning step).

In FIG. 2, the impurity signal plateau value is indicated by dotted horizontal lines. The signal plateau corresponds to the non-adsorbing impurities. The breakthrough areas $A_{ICiU}$, $A_{ICiD}$, and $A_{Bi}$, are confined by the breakthrough curve and the horizontal baseline and are indicated by two arrows each. "B" and "IC" indicate disconnected and interconnected phases, respectively. The quality of the baseline value depends on the point at which the value is recorded. To obtain the most stable value, preferably the baseline value for the horizontal baseline of $A_{ICiU}$ is determined such that the value for the second column is determined from the detector signal of the second column during the breakthrough of product from the first column and the value for the first column is determined from the detector signal of the first column during the breakthrough from the second column. As an example, in FIG. 5, during the recording of $A_{IC1U,2}$ from UV-1 (full line), the baseline value of UV-2 (dashed signal) for the determination of the upcoming $A_{IC2U,2}$ in the next IC phase is recorded. During the recording of $A_{IC2U,2}$ from UV-2, the baseline value for the determination of the upcoming $A_{IC1U,3}$ from UV-1 in the next IC phase is recorded.

All areas $A_{ICiU}$, $A_{peaki}$, $A_{ICiD}$, and $A_{Bi}$ are obtained by integration of peak/breakthrough curve signal using a suitable integration algorithm such as a trapezoidal method. The integration is not confined to a one-time calculation but can be done on an ongoing basis assuming a horizontal baseline and with time progressing.

In FIG. 2, the area above the plateau level in the 1st B phase B1 is designated "$A_{B1}$". "$A_{B1}$" corresponds to a product loss from column 1 during the loading step in the disconnected phase. The area above the plateau level in the 1st IC phase IC1 is designated $A_{IC1U}$ ("IC" stands for "interconnected phase", "1" stands for the number of the column/detector, "U" stands for upstream). The area $A_{IC1U}$ corresponds to product leaving the upstream column during the interconnected phase, however it does not correspond to product leaving the system since the product enters the second column. The product elution peak in the 2nd B phase is designated "$A_{peak1}$" and the area above the plateau level in the 2nd IC phase is referred to as $A_{IC1D}$) ("D" stands for downstream). In the 2nd IC phase, column 1 is downstream and receives the product eluting or rather breaking through from the upstream column 2. The area $A_{IC1D}$) is zero in the presented case corresponding to zero loss from the column 1 when column 1 is in the downstream position in the IC2 phase, indicating that the entire product eluting or rather breaking through from the upstream column 2 is adsorbed in column 1;

The method distinguishes between the breakthrough areas of the downstream columns in the interconnected loading phase of the columns, $A_{ICiD}$ (measured by detector i for column i), which reflect a loss of product; the breakthrough areas of the columns that are loaded in the disconnected state, $A_{Bi}$, which also reflect a loss of product, and the breakthrough areas of the upstream columns in the interconnected loading phase of the columns, $A_{ICiU}$. As said, the latter area represents the material that is transferred from the upstream to the downstream column and does not reflect a product loss.

When comparing $A_{ICiD}$, $A_{ICiU}$ and $A_{Bi}$ and $A_{peaki}$, the potentially different flow rates during the recording of the areas need to be taken into account. Areas can be normalized for different flows by multiplication with the flow rates.

The monitoring and control method is based on the comparison of at least the area below the breakthrough curve of a product of interest, '$A_{CiU}$' (measured by detector i). It may also include evaluating the elution peak signal '$A_{peaki}$' (measured by detector i) of a single cycle, corresponding to the product of interest, recorded by detectors located at the outlet of each column, evaluating the signal by means of suitable algorithms and deriving control actions therefrom, or a combination of evaluation of the area below the breakthrough curve '$A_{CiU}$' and evaluation of the elution peak signal '$A_{peaki}$'.

The monitoring and control method can be based on the comparison of at least the peak areas $A_{peaki}$, among different cycles and/or among different detectors as described further below and in the preferred embodiments. A method evaluating the elution peak signal '$A_{peaki}$' only can be also used in the case of high impurity signals where $A_{ICiD}$, $A_{ICiU}$ and $A_{Bi}$ cannot be measured. The method is capable of monitoring column capacity and feed concentration changes in a cycle-to-cycle manner, and to derive control actions from the measured areas.

In long term process operation, different causes such as decreasing feed concentration and simultaneous column degradation may lead to the same effects on breakthrough and peak areas causing the same control actions with the load L as only parameter (load L understood as the total amount, i.e. mass, of new product compound introduced into the system during one cycle via the feed stream(s), divided by the total bed volume of the chromatographic columns). It is an advantage of the presented method that it does not require detailed knowledge on the cause of the effects for successful process control. The aim of the control actions is generally to maintain a constant yield, a constant load L, or, preferably, a constant Preload PL, i.e. a constant amount of product entering the downstream column in the interconnected state loading step, in order to ensure a constant product concentration. Possible control actions for adapting the load in the subsequent chromatography cycles or cycle phases include, but are not limited to, changes of the feed flow rate in the B and/or IC phases, load durations, durations of the phases B and/or IC or changes of feed concentrations. The yield is adapted by changing the load, too. For instance, in case of low yield, in order to obtain a higher yield, the load L must be lowered. Another embodiment of the invention relates to an optimization method to maximize load and throughput of the process. This approach is relevant in process development in order to maximize the productivity of the process and to appropriately size the equipment when scaling up the process.

The optimization method includes the comparison of at least the eluate peak signal and/or breakthrough signals from different cycles of the process, the cycles to be evaluated can be consecutive but can also be spaced apart, to derive control actions there from. With regard to FIG. 2, the optimization would aim at maximizing $A_{peaki}$ while keeping $A_{Bi}$ to a minimum in the following cycles. $A_{ICiD}$ is automatically minimized if $A_{Bi}$ is minimized. As in the case of process monitoring and control, possible control or optimization actions for adapting the load in the subsequent chromatography cycles or cycle phases include, but are not limited to, changes of the feed flow rate in the B and/or IC phases, load durations, durations of the phases B and/or IC or changes of feed concentrations.

In order to maximize the process performance the load L is increased step-wise in a cycle-to-cycle fashion. The newly recorded areas, following the step change are compared to the areas of previous cycle and the process performance is re-calculated using the new values. In the case that measurements of breakthrough areas and peak elution area are possible due to a favorable detector signal, the process performance can be improved based on the areas determinations of a single cycle. In case only the peak elution areas can be determined (due to a large impurity signal), additional data from earlier or later cycles of the same run are required to determine the optimization potential of the process and to carry out the optimization. Further optimization method details are laid down in the preferred embodiments.

The method can be advantageously used to determine suitable operating parameters by calculation, avoiding a time-consuming experimental determination procedure.

By determining elution peak areas and breakthrough areas from the downstream column in the interconnected state and the loading column in the disconnected state, product loss and yield can be quantified online. A feed signal is not required.

The tedious task of detector calibration is also not required since the control actions are determined either from signals recorded with the same detector or from signals recorded from different detectors that have been normalized through calculation of ratios between signals recorded by each of the detectors. Another major advantage over prior art descriptions is that by using the peak areas as basis for one method of process control and optimization, the method can be applied for the control of processes for the purification of products from feedstocks that cause a very large impurity signal that is in the non-linear range of the detector and therefore do not allow measurement of breakthrough signals.

The described control and optimization methods can be used also for all other sequential loading chromatography processes with more than two columns since the concept of sequential loading always entails the presence of an area $A_{ICiD}$, corresponding to a product loss from the most downstream column. The number of areas $A_{ICiU}$, measured by inline detectors, and corresponding to product that is transferred from an upstream into a downstream column, may vary as more columns are interconnected, but these areas do not reflect product losses (see FIG. 2). The areas $A_{peaki}$ correspond to product recovery from a single column in all common multicolumn sequential loading processes. Areas $A_{Bi}$ are present if the multicolumn process comprises steps where one or more of the columns are loaded while being disconnected from the other columns. Some multicolumn processes comprise such steps while others do not.

For all processes, the common aim of control is to keep $A_{peaki}$, $A_{ICiD}$, and $A_{Bi}$, possibly also $A_{ICiu}$, within certain specification limits. The common aim of optimization is the maximization of $A_{peaki}$ while keeping $A_{ICiD}$, and, if present, also the areas $A_{Bi}$, to a minimum.

More specifically, in the case that $A_{ICiU}$, and $A_{Bi}$, are accessible to quantitative measurement by the detectors due to a low impurity signal, a method of monitoring and/or control and/or optimization of the process comprises the following elements:

(a) measuring the disconnected phase signals $A_{peaki}$ corresponding to the effluents of all columns (i) in a product elution position in a disconnected state in at least one cycle or parts of one cycle using the detectors at the columns outlets;

(b) measuring the interconnected phase signals $A_{ICiU}$ corresponding to the effluents of all columns (i) in an interconnected state upstream and/or downstream positions in at least one cycle or parts of one cycle using the detectors at the columns outlets (in the case of high impurity signals, where on $A_{peaki}$ can be evaluated (see e.g. examples 10, 11 below) it is possible to rely on only one detector for process control by using this detector for alternatingly recording $A_{peaki}$ from each column, as also outlined in the more general optimization process as given below, while for low impurity signals the use of two detectors is preferred);

(c) comparing the disconnected phase signals $A_{peaki}$ among the detectors, preferably by calculating the ratios between disconnected phase signals $A_{peaki}$ of the different detectors;

(d) comparing the interconnected phase signals $A_{ICiU}$ among the detectors, preferably by calculating the ratios between interconnected phase signals $A_{ICiU}$ of the different detectors;

(e) comparing the values of the disconnected phase signals $A_{peaki}$ comparison in step (c) and the interconnected phase signals $A_{ICiU}$ comparison (d) among the detectors in order to quantify the degree of the signal magnitude difference, and using this ratio and/or the ratios of (c) and/or (d) for control and/or monitoring. Specifically, a control action can be initiated based on this difference, e.g. actions to be implemented for at least one future cycle of the chromatographic process can be based on this difference, the chromatographic process can be halted due to e.g. deterioration of the columns and/or insufficient feed or the like, and/or it can be used to optimize the parameters of the process such as step timing, flow rates, load, yield (recovery), throughput, buffer consumption of the process.

In particular in the case that $A_{ICiU}$, and $A_{Bi}$ are accessible to quantitative measurement by the detectors due to a low impurity signal and the product concentration in the feed is constant, which is the case in a large number of applications, it is, according to another process of monitoring and/or control and/or optimization, possible to use a reduced process which comprises the following elements:

(a) measuring the interconnected phase signals $A_{ICiU}$ corresponding to the effluents of at least two, preferably all columns (i) in an interconnected state upstream and/or downstream positions in at least one cycle or parts of one cycle using the detectors at the columns outlets;

(b) comparing the interconnected phase signals $A_{ICiU}$ among the at least two, preferably all detectors, preferably by calculating the ratios between interconnected phase signals $A_{ICiU}$ of the different detectors and using this ratio for control and/or monitoring. Specifically, a control action can be initiated based on this difference/ratio, e.g. actions to be implemented for at least one future cycle of the chromatographic process can be based on this difference, the chromatographic process can be halted due to e.g. deterioration of the columns and/or insufficient feed or the like, it can be used to optimize the parameters such as timing, flow rates, load, yield (recovery), throughput, buffer consumption of the process.

In the case that $A_{ICiU}$, and $A_{Bi}$ are accessible to quantitative measurement by the detectors due to a low impurity signal and the product concentration in the feed is constant, it is, according to another preferred process of monitoring and/or control, possible to use a further reduced process which comprises the following elements:

(a) measuring the interconnected phase signals $A_{ICiU}$ corresponding to the effluents of at least two, preferably all columns (i) in an interconnected state upstream and/or downstream positions in at least one cycle or parts of one cycle using the detectors at the columns outlets;

(b) initiating a control action based on $A_{ICiU}$ reaching a specific set point value. The control action can be related to timing, flow rates, load, yield (recovery), throughput, buffer consumption of the process. In particular, the control action can comprise stopping the interconnected loading phase upon $A_{ICiU}$ reaching a pre-defined or automatically calculated set point value and initiating the interconnected washing or the subsequent loading step.

In particular in the case that $A_{ICiU}$ and $A_{Bi}$ are not accessible to quantitative measurement by the detectors due to a high impurity signal, and the feed concentration is constant, which is the case in a large number of applications, the proposed process of monitoring and/or control and/or optimization to maximize load and throughput of the process comprises the following elements:

(a) measuring the disconnected phase signals $A_{peaki}$ corresponding to the effluents of all columns in a product elution position in a disconnected state in at least one cycle or parts of one cycle using the detectors at the columns outlets;

(b) comparing the disconnected phase signals $A_{peaki}$ among the two detectors, preferably by calculating the ratios between disconnected phase signals $A_{peaki}$ of the different detectors;

(c) comparing the values of the disconnected phase signals $A_{peaki}$ or ratios thereof of at least one cycle among two detectors in order to quantify the degree of the signal magnitude difference, and using this difference for control and/or monitoring. Specifically, a control action can be initiated based on this difference, e.g. actions to be implemented for at least one future cycle of the chromatographic process can be based on this difference, the chromatographic process can be halted due to e.g. deterioration of the columns and/or insufficient feed or the like, it can used to optimize the parameters such as timing, flow rates, load, yield (recovery), throughput, buffer consumption of the process.

In the abovementioned control methods, preferably the control action is the change of the column load by reduction or increase of the feed flow rate in one or multiple phases of the cyclic process. In another preferred embodiment, the control action is the change of the duration of the interconnected or the disconnected phase, respectively.

In other embodiments the control actions include the reduction or increase of the feed interval duration, changes of the feed composition (for instance by dilution).

More Generalized Control, Monitoring and Optimization Method:

The above-mentioned control, monitoring and optimization method is preferably applied to the above-mentioned chromatographic capture method i.e. using a process involving recovery of product with an interconnected step of the at least 2 columns. However the control, monitoring and optimization method can also be applied more generally, so it can also be applied in case of processes which do not involve an interconnected step but where 2 columns are operated alternatingly, in a so called tandem operation which is schematically illustrated in a preferred embodiment in FIG. 10.

Specifically, such a more generalized control, monitoring and optimization process for a chromatographic separation process comprising at least 2 columns which are operated alternatingly, and wherein downstream of at least one, preferably of each column, a detector is located capable of detecting the desired product and/or impurities when passing the detector, is carried out as follows:

(a) measuring the disconnected areas ($A_{peaki}$) corresponding to the effluents of at least one, preferably of at least two, more preferably of all columns in a product elution position in a disconnected state in at least one cycle or parts of one cycle using the detector(s) at the column(s) outlet(s);
and/or (b) measuring the area confined by the breakthrough curve and a horizontal baseline ($A_{Bi}$) in a product load position in a disconnected state in at least one cycle or parts of one cycle using the detector(s) at the column(s) outlet(s) (under optimum process conditions this area should be zero which means that the product loss is zero; if this area is larger than zero it means that there is product loss, and normally means that the load should be reduced), or measuring, in case of alternating operation in interconnected and disconnected state, the interconnected areas ($A_{ICiU}$) corresponding to the effluents of at least one, preferably of all columns in an interconnected state upstream and/or downstream positions in at least one cycle or parts of one cycle using the detectors at the columns outlets;
and (c) using the measured values of the disconnected areas ($A_{Bi,n}$, $A_{peaki}$) in step (a) and/or, in case of alternating operation in interconnected and disconnected state, the interconnected areas ($A_{ICiU}$) in step (b) of the at least one, preferably at least two detectors for control and/or monitoring and/or optimization of at least one process parameter.
and/or (d) optionally comparing the disconnected areas ($A_{Bi,n}$ and/or $A_{peaki}$) of the at least one, preferably at least two detectors of the current cycle n with the disconnected area of at least one previous cycle ($A_{Bi,n-1}$ and/or $A_{peaki,n-1}$), e.g. by calculating the ratios between disconnected areas ($A_{Bi,n}/A_{Bi,n-1}$ and/or $A_{peaki}/A_{peaki,n-1}$) of the at least one detector;
and/or (e) optionally comparing, in case of alternating operation in interconnected and disconnected state, the interconnected areas ($A_{ICiU}$) of the current cycle n with the interconnected area of at least one previous cycle ($A_{ICiU,n-1}$) of the at least one detector, preferably at least two detectors, preferably by calculating the ratios between interconnected areas ($A_{ICiU}$ and $A_{ICiU,n-1}$);
and (f) using the comparison of the values of the disconnected areas ($A_{Bi,n}$, $A_{peaki}$) in step (d) and/or, in case of alternating operation in interconnected and disconnected state, the interconnected areas ($A_{ICiU}$) comparison in step (e) of the at least one, preferably at least two detectors in order to quantify the degree of the signal magnitude difference and using this difference for control and/or monitoring and/or optimization of at least one process parameter.

According to a preferred embodiment, in case of a tandem process, the proposed control and/or monitoring process comprises the following elements:

(a) Measuring the disconnected areas ($A_{Bi}$, and/or $A_{peaki}$) corresponding to the effluents of at least one, preferably at least two, more preferably of all columns in a product elution position in a disconnected state in at least one cycle or parts of one cycle using the detectors at the columns outlets;
and (c) Using the measured values of the disconnected areas ($A_{Bi,n}$, $A_{peaki}$) in step (a) of the at least one, preferably at least two detectors for control and/or monitoring and/or optimization of at least one process parameter.

According to another preferred embodiment, in case of a tandem process, the proposed control and/or monitoring and/or optimization process comprises the following elements:

(a) measuring the disconnected areas ($A_{Bi}$, and/or $A_{peaki}$) corresponding to the effluents of at least one, preferably at least two, more preferably of all columns in a product elution position in a disconnected state in at least one cycle or parts of one cycle using the detectors at the columns outlets;
and (d) comparing the disconnected areas ($A_{Bi,n}$ and/or $A_{peaki,n}$) of the at least one preferably at least two detectors of the current cycle n with the disconnected area of at least one previous cycle ($A_{Bi,n-1}$ and/or $A_{peaki,n-1}$), preferably by calculating the ratios between disconnected areas ($A_{Bi,n}/A_{Bi,n-1}$ and/or $A_{peaki}/A_{peaki,n-1}$) of the at least one detector and (f) using the comparison of the values of the disconnected areas ($A_{Bi,n}, A_{peaki}$) in step (d) in order to quantify the degree of the signal magnitude difference and using this difference for control and/or monitoring and/or optimization of at least one process parameter.

According to a preferred embodiment, in case of a chromatographic capture method i.e. using a process involving recovery of feed with an interconnected step of the at least 2 columns, said method for control and/or monitoring comprises the following elements:

(b) measuring, in case of alternating operation in interconnected and disconnected state, the interconnected areas ($A_{ICiU}$) corresponding to the effluents of at least one, preferably of two or all columns in an interconnected state upstream and/or downstream positions in at least one cycle or parts of one cycle using the detector(s) at the columns outlets;
and (c) using the measured values of the interconnected areas ($A_{ICiU}$) in step (b) of the at least one, preferably at least two detectors for control and/or monitoring of at least one process parameter.

According to a preferred embodiment, in case of a chromatographic capture method i.e. using a process involving recovery of feed with an interconnected step of the at least 2 columns, said method for control and/or monitoring and/or optimization comprises the following elements:

(b) measuring, in case of alternating operation in interconnected and disconnected state, the interconnected areas ($A_{ICiU}$) corresponding to the effluents of at least one, preferably of two or all columns in an interconnected state upstream and/or downstream positions in at least one cycle or parts of one cycle using the detector(s) at the columns outlets;
and (e) comparing the interconnected areas ($A_{ICiU}$) among the at least one, preferably at least two detectors, preferably by calculating the ratio(s) between interconnected areas ($A_{ICiU}$) of the detector(s);
and (f) comparing the values of the interconnected areas ($A_{ICiU}$) comparison in step (e) among at least one, preferably at least two detectors in order to quantify the degree of the signal magnitude difference and using this difference for control and/or monitoring and/or optimization of at least one process parameter.

The proposed optimization of a chromatographic process may further comprise the following elements:

(a) in case of alternating operation in interconnected and disconnected state, loading the columns such that the disconnected area ($A_{peaki}$) is smaller than 80% of the maximum disconnected area ($A_{peaki,max}$) that is expected or known from previous chromatographic runs or cycles or parts thereof of the same chromatographic run, (b) changing operating parameters, from cycle to cycle or multiples or parts thereof, such that the column load (L) is maximized while the ratio of the corresponding disconnected area ($A_{peaki,n}$) and the load remains constant at the level defined by the column load and the disconnected area ($A_{peaki}$) in step (a).

Furthermore the present invention relates to a computer program product, preferably on a storage medium, adapted to automatically design and/or control and/or monitor and/or optimize a process as defined above based on a numerical evaluation, preferably an integral, differential and/or ratio-based numerical evaluation, of signals from the detector(s) or from offline analyses, in particular based on a numerical evaluation, preferably an integral, differential and/or ratio-based numerical evaluation, of signals from the detectors or from offline analyses of at least two cycles.

Schematically the basis for such a computer program in a preferred embodiment is illustrated in the flow diagrams of FIG. 11a and FIG. 11b which will be detailed further below.

The present disclosure provides:

Embodiment 1. Chromatographic purification method for the isolation of a desired product fraction from a mixture using 2 chromatographic columns (1,2), wherein the method comprises, within one cycle to be carried out at least once, the following steps:
a first batch step (B1), wherein during a batch timespan ($t_B$) said columns are disconnected and
a first column (1) is loaded with feed via its inlet using a first flow rate ($Q_{feed,B}$) and its outlet is directed to waste, and
from a second column (2) thereof desired product is recovered via its outlet and subsequently the second column (2) is regenerated;
a first interconnected step (IC1), wherein the outlet of the first column (1) is connected to the inlet of the second column (2) during an interconnected timespan ($t_{IC}$),
the first column (1) is loaded beyond its dynamic breakthrough capacity with feed via its inlet using a second flow rate ($Q_{feed,IC}$) which is the same or larger than the first flow rate ($Q_{feed,B}$), and
the outlet of the second column (2) is directed to waste, and wherein during a subsequent washing timespan ($t_{wash,IC}$ which is larger or equal to 0 s
the outlet of the first column (1) is connected to the inlet of the second column (2),
the first column (1) is loaded with solvent and/or buffer which is free from feed material, and
the outlet of the second column (2) is directed to waste,
a second batch step (B2) analogous to the first batch step (B1) but with exchanged column positions, such that the first column (1) of the first batch step (B1) performs the tasks of the second column (2) of the first batch step (B1), and the second column (2) of the first batch step (B1) performs the tasks of the first column (1) of the first batch step (B1);
a second interconnected step (IC2), analogous to the first interconnected step (IC1) but with exchanged column positions, such that the upstream column (1) of the first interconnected step (IC1) is the downstream column of the second interconnected step (IC2), and the downstream column (2) of the first interconnected step (B1) is the upstream column of the second interconnected step (IC2).

Embodiment 2. Chromatographic method according to embodiment 1, wherein in the interconnected step (IC) the second flow rate ($Q_{feed,IC}$) is adapted to be larger than the first flow rate ($Q_{feed,B}$), preferably at least 10% larger, more preferably at least 25% larger, most preferably 1.5-2.0 times or 1.5-4.0 times larger than the first flow rate ($Q_{feed,B}$).

Embodiment 3. Chromatographic method according to any of the preceding embodiments, wherein in the interconnected step (IC) the second flow rate ($Q_{feed,IC}$) and/or the interconnected timespan ($t_{IC}$) are adapted such that at the end of interconnected timespan ($t_{IC}$) the feed concentration at the outlet of the upstream column is in the range of 30-90% of the feed concentration at the inlet of the upstream column, with the proviso that the values of the second flow rate ($Q_{feed,IC}$) and/or the interconnected timespan ($t_{IC}$) are adapted such that at the end of the interconnected timespan ($t_{IC}$) at the outlet of the downstream column the feed concentration is below a breakthrough value of 0.25-5%, preferably of 1-2.5%, and that the elution volume corresponding to this breakthrough value is preferably multiplied with a safety factor in the range of 60-90%.

Embodiment 4. Chromatographic method according to any of the preceding embodiments, wherein the batch timespan ($t_B$) is chosen to be the accumulated time required for the recovery and regeneration of the respective column, wherein preferably this accumulated time is given by the accumulated time required for the steps of: (i) washing with solvent and/or buffer under conditions that the product is not released from the stationary phase; (ii) elution with solvent and/or buffer under conditions that the product is released from the stationary phase; (iii) cleaning in place using a solvent and/or buffer to release everything from the stationary phase; (iv) equilibration, preferably by using the solvent and/or buffer under conditions similar or the same as in the subsequent process steps.

Embodiment 5 Chromatographic method according to any of the preceding embodiments, wherein the columns are affinity chromatography material loaded columns, wherein further preferably the chromatographic stationary phase is in the form of particles, preferably in the form of beads and/or membranes and/or monoliths.

Embodiment 6. Chromatographic method according to any of the preceding embodiments, wherein at the outlet of each column a detector for the analysis of the components at the outlet is located, preferably both detectors being of the same type, wherein preferably this is a detector selected from one or a combination of the following detectors: UV detector, visible light detector, IR detector, fluorescence detector, light scattering detector, refractive index detector, pH detector, conductivity detector, at-line HPLC analysis, Raman detector or mass spectrometry detector.

Embodiment 7. Chromatographic method according to any of the preceding embodiments, wherein the first cycle is preceded by a startup step, in which the columns are interconnected and wherein a larger amount of feed solution is loaded into the upstream column in comparison with an interconnected step (IC) of a cycle of the method,
and/or the last cycle is followed by a shutdown step, in which the two columns are disconnected, and both columns are subjected to product recovery and column regeneration.

Embodiment 8. Chromatographic method according to any of the preceding embodiments, wherein the desired product is one or a group of chemical reaction products, chemical separation products, biochemical reaction products, biological products, wherein preferably the reaction products are natural products, metals, antibodies, antibody fragments, fusion proteins, recombinant glycoproteins, and/or plasma proteins, or derivatives and/or combinations and/or mixtures thereof.

Embodiment 9. Method for setting up a chromatographic process according to any of the preceding embodiments, wherein
the batch step duration ($t_B$) of the batch step (B) is set to be the accumulated time required for recovery and regeneration of the respective column, and the batch step feed flow rate ($Q_{feed,B}$) applied to the respective column in the batch step (B) is set such that at the end of the batch step duration ($t_B$) at the outlet of the column there is essentially no desired product elution, taking into account that in the preceding step this column has already been preloaded,
and wherein the interconnected step feed flow rate ($Q_{feed,IC}$) is set to a desired value and the interconnected step duration ($t_{IC}$) is set such that at the end of the interconnected step duration ($t_{IC}$) at the outlet of the upstream column the desired product concentration is in desired range, preferably in the range of 30-90%, of the concentration at its inlet, with the proviso that there is essentially no desired product elution at the outlet of the downstream column,
and wherein for the determination of the batch step feed flow rate ($Q_{feed,B}$) and the interconnected step duration ($t_{IC}$) at least one breakthrough curve of a single column using the interconnected step feed flow rate ($Q_{feed,IC}$) is recorded and used, if needed at least one breakthrough curve of interconnected columns using the interconnected step feed flow rate ($Q_{feed,IC}$) is recorded and used, and wherein at least one breakthrough curve of a single column using a lower batch step feed flow rate ($Q_{feed,B}$) than the interconnected step feed flow rate ($Q_{feed,IC}$) is recorded and used, wherein preferably the lower batch step feed flow rate ($Q_{feed,B}$) for the determination of this breakthrough curve is chosen to be 50-90% of the interconnected step feed flow rate ($Q_{feed,IC}$).

Embodiment 10. Method for setting up a chromatographic process according to embodiment 9, wherein the following steps are carried out, preferably in the given order:
(a) calculation of the duration of the disconnected state ($t_B$) by summing up of the durations of recovery and regeneration steps carried out with the column which is not fed with feed;
(b) determination of the elution volume breakthrough value ($EV_2$) of two interconnected columns using the desired maximum feed flow rate ($Q_{feed,IC}$) of the interconnected state by measuring a dynamic breakthrough curve of two sequential columns ($DBC_2$) and determining of the elution volume (EV) corresponding to a desired breakthrough value, preferably 1% breakthrough up to 5% breakthrough, with respect to the feed concentration, optionally multiplied with a safety factor, preferably in the range between 0.5 and 1.0;
(c) determination of the elution volume breakthrough value of a single column using the feed flow rate $Q_{feed,IC}$, wherein a full breakthrough curve ($DBC_{1H}$) is recorded, and wherein optionally the elution volume ($EV_{1H,1}$) corresponding to a desired low breakthrough value of the single column, preferably 1% breakthrough with respect to the feed concentration is determined;
(d) determination, from the breakthrough curve determined in step (c), of the X % breakthrough elution volume ($EV_{1H,X}$) corresponding to a high load of the single column using the desired maximum flow rate of the single column load operation, wherein X is typically a number between 50 and 90%;

(e) determining ($EV_Y$), the smaller one of the two elution volume values ($EV_2$) (b) and ($EV_{1,H,X}$) (d);
(f) determination of the preload value PL, calculated by integrating the difference of the calibrated breakthrough curve ($DBC_{1H}$) of the single column, as determined in step (c), and the calibrated breakthrough curve ($DBC_2$) of the interconnected columns, as determined in above step (b), with the upper boundary of the value determined in step (e) ($EV_Y$), divided by the column volume of the single column according to equation 1:

$$PL = \frac{1}{V_{col}} \cdot \int_{EV_{1H,1}}^{EV_Y} DBC_{1H}(EV) - DBC_2(EV) dEV \qquad \text{(equation 1)}$$

wherein also zero can be used as lower starting point for the integration;
(g) determination of a second breakthrough value ($EV_{1L,1}$) of a single column using a lower flow rate ($Q_{feed,BT1L}$) by choosing a reduced feed flow rate, preferably a feed rate 50-90% of the feed flow rate used in step (c), and recording a full breakthrough curve ($DBC_{1L}$) and determination of the elution volume corresponding to a desired low breakthrough value, preferably 1% breakthrough with respect to the feed concentration, preferably choosing the same value as in the determination of the single column breakthrough value at the higher flow rate;
(h) determination of the interconnected state switch ($t_{IC}$) time by subtracting the second breakthrough value multiplied with a safety factor (Z %·$EV_{1L,1}$) from the value determined in (e) ($EV_Y$) and dividing the complete term by the feed flow rate ($Q_{feed,IC}$) in the interconnected state, according to equation 2:

$$t_{IC} = (EV_Y - Z\%·EV_{1L,1})/Q_{feed,IC} \qquad \text{(equation 2);}$$

(i) determination of the target load value (TL), from the two breakthrough curves ($DBC_1$) and ($DBC_{1L}$) of the single columns by preferably subtracting the dead volume from the elution volume corresponding to the desired breakthrough, preferably of a breakthrough of 1%, multiplied with a safety factor Z, and multiplying the difference with the feed concentration value, dividing said product by the column volume and subtracting PL from this value, according to equation 3:

$$TL = ((Z\%·EV_{1L,1} - V_{dead})·c_{feed})/V_{col} - PL \qquad \text{(equation 3);}$$

(j) determination of the feed flow rate of the disconnected state ($Q_{feed,B}$), according to equation 4 by multiplying the target load value (TL) with the column volume, dividing by the feed concentration, and dividing by the duration of the disconnected state ($t_B$) according to equation 4

$$Q_{feed,B} = (TL·V_{col})/(c_{feed}·t_B) \qquad \text{(equation 4).}$$

Embodiment 11. Method for setting up a chromatographic process according to embodiment 9, wherein
(k) for the determination of the startup time ($t_{startup}$) the difference of the second breakthrough value multiplied with a safety margin (Z %·$EV_{1L,1}$) and the dead volume of a single column ($V_{dead}$) by the feed flow rate ($Q_{feed,IC}$) and adding this value to the duration of the interconnected step ($t_{IC}$), according to equation 5

$$t_{startup} = t_{IC} + (Z\%·EV_{1L,1} - V_{dead})/Q_{feed,IC} = (EV_Y - V_{dead})/Q_{feed,IC} \qquad \text{(equation 5)}$$

and/or wherein
(l) for the determination of the duration of the interconnected state washing step ($t_{wash,IC}$) that follows the interconnected phase loading step at least the dead volume ($V_{dead}$) is divided by the flow rate ($Q_{wash,IC}$) naccording to equation 6:

$$t_{wash,IC} = k \, V_{dead}/Q_{wash,IC} \qquad \text{(equation 6)}$$

with k as rational number >1.

Embodiment 12. Method for control and/or monitoring and/or optimization of a chromatographic process, preferably of a process as defined in any of the preceding embodiments 1-8, in which the process comprises at least 2 columns which are operated, alternatingly, in interconnected and disconnected state, and in which the columns switch positions after such a sequence of interconnected and disconnected state, and wherein downstream of each column a detector is located capable of detecting the desired product and/or impurities when passing the detector, wherein the method comprises the following elements:

(a) measuring the disconnected areas ($A_{peaki}$) corresponding to the effluents of at least two, preferably of all columns in a product elution position in a disconnected state in at least one cycle or parts of one cycle using the detectors at the columns outlets;

and/or (b) measuring the interconnected areas ($A_{ICiU}$) corresponding to the effluents of at least one, preferably of all columns in an interconnected state upstream and/or downstream positions in at least one cycle or parts of one cycle using the detectors at the columns outlets;

and (c) comparing the disconnected areas ($A_{peaki}$) among the at least two detectors, preferably by calculating the ratios between disconnected areas ($A_{peaki}$) of the detectors;

and/or (d) comparing the interconnected areas ($A_{ICiU}$) among the at least two detectors, preferably by calculating the ratios between interconnected areas ($A_{ICiU}$) of the detectors;

and (e) comparing the values of the disconnected areas ($A_{peaki}$) comparison in step (c) and/or the interconnected areas ($A_{ICiU}$) comparison in step (d) among at least two detectors in order to quantify the degree of the signal magnitude difference and using this difference for control and/or monitoring and/or optimization of at least one process parameter.

Embodiment 13. Method for control and/or monitoring and/or optimization of a chromatographic process according to embodiment 12, wherein the method comprises the following elements:

(a) measuring the disconnected areas ($A_{peaki}$) corresponding to the effluents of at least two, preferably of all columns in a product elution position in a disconnected state in at least one cycle or parts of one cycle using the detectors at the columns outlets;
and
(c) comparing the disconnected areas ($A_{peaki}$) among the at least two detectors, preferably by calculating the ratios between disconnected areas ($A_{peaki}$) of the detectors;
and
(e) comparing the values of the disconnected areas ($A_{peaki}$) comparison in step (c) in order to quantify the degree of the signal magnitude difference and using this difference for control and/or monitoring and/or optimization of at least one process parameter.

Embodiment 14. Method for control and/or monitoring and/or optimization of a chromatographic process according to embodiment 12, wherein the method comprises the following elements:
(b) measuring the interconnected areas ($A_{ICiU}$) corresponding to the effluents of at least one, preferably of all columns in an interconnected state upstream and/or downstream positions in at least one cycle or parts of one cycle using the detectors at the columns outlets;
and
(d) comparing the interconnected areas ($A_{ICiU}$) among the at least one or at least two detector(s), preferably by calculating the ratios between interconnected areas ($A_{ICiU}$) of the detector(s);
and
(e) comparing the values of the interconnected areas ($A_{ICiU}$) comparison in step
(d) among at least one or at least two detector(s) in order to quantify the degree of the signal magnitude difference and using this difference for control and/or monitoring and/or optimization of at least one process parameter.

Embodiment 15. Method for optimization of a chromatographic process according to any of embodiments 12-14, wherein the method comprises the following elements:
(a) loading the columns such that the initially determined disconnected area ($A_{peaki}$) is smaller than 80% of the maximum disconnected area ($A_{peaki,max}$) that is expected or known from previous chromatographic runs or cycles or parts thereof of the same chromatographic run,
(b) changing operating parameters, from cycle to cycle or parts thereof, such that the column load (L) is maximized while the ratio of the corresponding disconnected area ($A_{peaki,n}$) and the load remains constant at the level defined by the column load and the disconnected area ($A_{peaki}$) in step (a).

Embodiment 16. Method for control and/or monitoring and/or optimization of a chromatographic process, preferably of a process as defined in any of the preceding embodiments 1-8, in which the process comprises at least 2 columns which are operated, alternatingly,
wherein preferably this operation is carried out in that the at least 2 columns are operated in interconnected and disconnected states, wherein the columns switch positions after such a sequence of interconnected and disconnected state,
and wherein downstream of at least one, preferably of each column, a detector is located capable of detecting the desired product and/or impurities when passing the detector, wherein the method comprises the following elements:
(a) measuring the disconnected areas ($A_{Bi}$, and/or $A_{peaki}$) corresponding to the effluents of at least one, preferably of at least two, more preferably of all columns in a product elution position in a disconnected state in at least one cycle or parts of one cycle using the detector(s) at the column(s) outlet(s);
and/or
(b) measuring the area confined by the breakthrough curve and a horizontal baseline ($A_{Bi}$) in a product load position in a disconnected state in at least one cycle or parts of one cycle using the detector(s) at the column(s) outlet(s), or measuring, in case of alternating operation in interconnected and disconnected state, the interconnected areas ($A_{ICiU}$) corresponding to the effluents of at least one, preferably of all columns in an interconnected state upstream and/or downstream positions in at least one cycle or parts of one cycle using the detector(s) at the column(s) outlet(s);
followed by at least one of the following steps:
(c) using the measured values of the disconnected areas ($A_{Bi,n}$, $A_{peaki}$) in step (a) and/or, in case of alternating operation in interconnected and disconnected state, the interconnected areas ($A_{ICiU}$) in step (b) of the at least one, preferably at least two detectors for control and/or monitoring and/or optimization of at least one process parameter;
and
(d) comparing the disconnected areas ($A_{Bi,n}$ and/or $A_{peaki,n}$) of the at least one, preferably at least two detectors of the current cycle n with the disconnected area of at least one previous cycle ($A_{Bi,n-1}$ and/or $A_{peaki,n-1}$), preferably by calculating the ratios between disconnected areas ($A_{Bi,n}/A_{Bi,n-1}$ and/or $A_{peaki,n}/A_{peaki,n-1}$) of the at least one detector;
and
(e) comparing, in case of alternating operation in interconnected and disconnected state, the interconnected areas ($A_{ICiU}$) of the current cycle n with the interconnected area of at least one previous cycle ($A_{ICiU,n-1}$) of the at least one detector, preferably at least two detectors, preferably by calculating the ratios between interconnected areas ($A_{ICiU}$ and $A_{ICiU,n-1}$);
and, in case of either or both of steps d) or e),
(f) using the comparison of the values of the disconnected areas ($A_{Bi,n}$, $A_{peaki}$) in step (c) or (d) and/or, in case of alternating operation in interconnected and disconnected state, the interconnected areas ($A_{ICiU}$) comparison in step (c) or (e) of the at least one, preferably at least two detectors in order to quantify the degree of the signal magnitude difference and using this difference for control and/or monitoring and/or optimization of at least one process parameter.

Embodiment 17. Method for control and/or monitoring and/or optimization of a chromatographic process according to embodiment 16, wherein the method, in case of a process without interconnected state, comprises the following elements:
(a) measuring the disconnected areas ($A_{Bi}$, and/or $A_{peaki}$) corresponding to the effluents of at least one, preferably at least two, more preferably of all columns in a product elution position in a disconnected state in at least one cycle or parts of one cycle using the detector(s) at the column(s) outlet(s);
and
(c) comparing the disconnected areas ($A_{Bi,n}$ and/or $A_{peaki,n}$) of the at least one preferably at least two detectors of the current cycle n with the disconnected area of at least one previous cycle ($A_{Bi,n-1}$ and/or $A_{peaki,n-1}$), preferably by calculating the ratios between disconnected areas ($A_{Bi,n}/A_{Bi,n-1}$ and/or $A_{peaki}/A_{peaki,n-1}$) of the at least one detector and (e) using the comparison of the values of the disconnected areas ($A_{Bi,n}$, $A_{peaki}$) in step (c) in order to quantify the degree of the signal magnitude difference and using this difference for control and/or monitoring and/or optimization of at least one process parameter.

Embodiment 18. Method for control and/or monitoring and/or optimization of a chromatographic process according to embodiment 16, wherein the method, in case of a process without interconnected state, comprises the following elements:

(a) measuring the disconnected areas ($A_{Bi}$, and/or $A_{peaki}$) corresponding to the effluents of at least one, preferably at least two, more preferably of all columns in a product elution position in a disconnected state in at least one cycle or parts of one cycle using the detectors at the columns outlets; and (c) Using the measured values of the disconnected areas ($A_{Bi,n}$, $A_{peaki}$) in step (a) of the at least one, preferably at least two detectors for control and/or monitoring and/or optimization of at least one process parameter.

Embodiment 19. Method for control and/or monitoring and/or optimization of a chromatographic process according to embodiment 12, wherein the method comprises the following elements:

(b) measuring the interconnected phase signals $A_{ICiU}$ corresponding to the effluents of at least two, preferably all columns (i) in an interconnected state upstream and/or downstream positions in at least one cycle or parts of one cycle using the detectors at the columns outlets;

(d) Comparing the interconnected phase signals $A_{ICiU}$ among the at least two, preferably all detectors, preferably by calculating the ratios between interconnected phase signals $A_{ICiU}$ of the different detectors and using this ratio for control and/or monitoring.

Embodiment 20. Method for control and/or monitoring and/or optimization of a chromatographic process, preferably of a process as defined in any of the preceding embodiments 1-8, in which the process comprises at least 2 columns which are operated, alternatingly, wherein preferably this operation is carried out in that the at least 2 columns are operated in interconnected and disconnected states, wherein the columns switch positions after such a sequence of interconnected and disconnected state, and wherein downstream of at least one, preferably of each column, a detector is located capable of detecting the desired product and/or impurities when passing the detector, wherein the method comprises the following elements:

(b) measuring, in case of alternating operation in interconnected and disconnected state, the interconnected areas ($A_{ICiU}$) corresponding to the effluents of at least one, preferably of two or all columns in an interconnected state upstream and/or downstream positions in at least one cycle or parts of one cycle using the detector(s) at the columns outlets;

and (c) using the measured values of the interconnected areas ($A_{ICiU}$) in step (b) of the at least one, preferably at least two detectors for control and/or monitoring of at least one process parameter, preferably including initiating a control action based on the measured values of the interconnected areas ($A_{ICiU}$) reaching a specific target set point value, wherein the control action can be related to at least one of timing, flow rates, load, yield, including recovery, throughput, buffer consumption of the process, and wherein in particular, the control action can comprise stopping the interconnected loading phase upon the measured values of the interconnected areas ($A_{ICiU}$) reaching a pre-defined or automatically calculated set point value and initiating the interconnected washing or the subsequent loading step.

Embodiment 21. Method for control and/or monitoring and/or optimization of a chromatographic process according to embodiment 16, wherein the method, in case of a process in which the at least 2 columns are operated in interconnected and disconnected state, wherein the columns switch positions after such a sequence of interconnected and disconnected state comprises the following elements:

(b) measuring, in case of alternating operation in interconnected and disconnected state, the interconnected areas ($A_{ICiU}$) corresponding to the effluents of at least one, preferably of two or all columns in an interconnected state upstream and/or downstream positions in at least one cycle or parts of one cycle using the detector(s) at the column(s) outlet(s);

and (d) comparing, in case of alternating operation in interconnected and disconnected state, the interconnected areas ($A_{ICiU}$) of the current cycle n with the interconnected area of at least one previous cycle ($A_{ICiU,n-1}$) of the at least one detector, preferably at least two detectors, preferably by calculating the ratios between interconnected areas ($A_{ICiU}$ and $A_{ICiU,n-1}$);

and (e) using the interconnected areas ($A_{ICiU}$) comparison in step (d) of the at least one, preferably at least two detectors in order to quantify the degree of the signal magnitude difference and using this difference for control and/or monitoring and/or optimization of at least one process parameter.

Embodiment 22. Method for optimization of a chromatographic process according to any embodiments 16-18, wherein the method comprises the following elements:

(a) in case of alternating operation in interconnected and disconnected state, loading the columns such that the initially determined disconnected area ($A_{peaki}$) is smaller than 80% of the maximum disconnected area ($A_{peaki,max}$) that is expected or known from previous chromatographic runs or cycles or parts thereof of the same chromatographic run, (b) changing operating parameters, from cycle to cycle or multiples or parts thereof, such that the column load (L) is maximized while the ratio of the corresponding disconnected area ($A_{peaki,n}$) and the load remains constant at the level defined by the column load and the disconnected area ($A_{peaki}$) in step (a).

Embodiment 23. A computer program product, preferably on a storage medium, adapted to automatically design and/or control and/or monitor and/or optimize a process according to any of the preceding embodiments based on a numerical evaluation, preferably a differential and/or ratio-based numerical evaluation, of signals from the detectors or from offline analyses, in particular based on a numerical evaluation, preferably an integral, differential and/or ratio-based numerical evaluation, of signals from the detector(s) or from offline analyses of at least two cycles.

Further embodiments of the invention are laid down in the dependent claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Preferred embodiments of the invention are described in the following with reference to the drawings, which are for the purpose of illustrating the present preferred embodiments of the invention and not for the purpose of limiting the same. In the drawings.

DESCRIPTION OF PREFERRED EMBODIMENTS

Example 1: Initial Determination of Operating Parameters for a Twin Column Countercurrent Sequential Loading Process The initial operating parameters for a twin-column countercurrent sequential loading process for the purification of an IgG from clarified cell culture harvest using protein A affinity chromatography were determined based on the procedure outlined above. The breakthrough curves were recorded, fractionated and analyzed by offline Protein A analysis using a Poros A/20 column (Life technologies, USA) to determine the IgG concentrations. The concentration of IgG in the feed was 1.0 g/L. The columns were of 0.5 cm inner diameter and 5.0 cm length. A protocol for the elution and regeneration of a loaded column was developed including a wash step of 6 min, an elution step of 7 min, a cleaning step of 6 min, a first equilibration step of 3 min, and a second equilibration step of 3 min; all at a flow rate of 1 mL/min. Thus, the total duration of the elution and regeneration steps was $t_B$=25 min.

A first breakthrough curve for a single column was recorded for a feed flow rate of 1 mL/min, a second breakthrough curve for a single column at a feed flow rate of 0.5 mL/min and a third breakthrough curve at a feed flow rate of 1 mL/min for two columns in series. With the load factor X=75%, and the safety factor Z=90%, the following elution volume values were obtained (see above descriptions and equations):

$$EV_{1H,1}=19.9 \text{ mL}, EV_{1L,1}=23.4 \text{ mL}, EV_{1H,75}=48.4 \text{ mL} \text{ and } EV_2=60.8 \text{ mL}.$$

Figure 1:
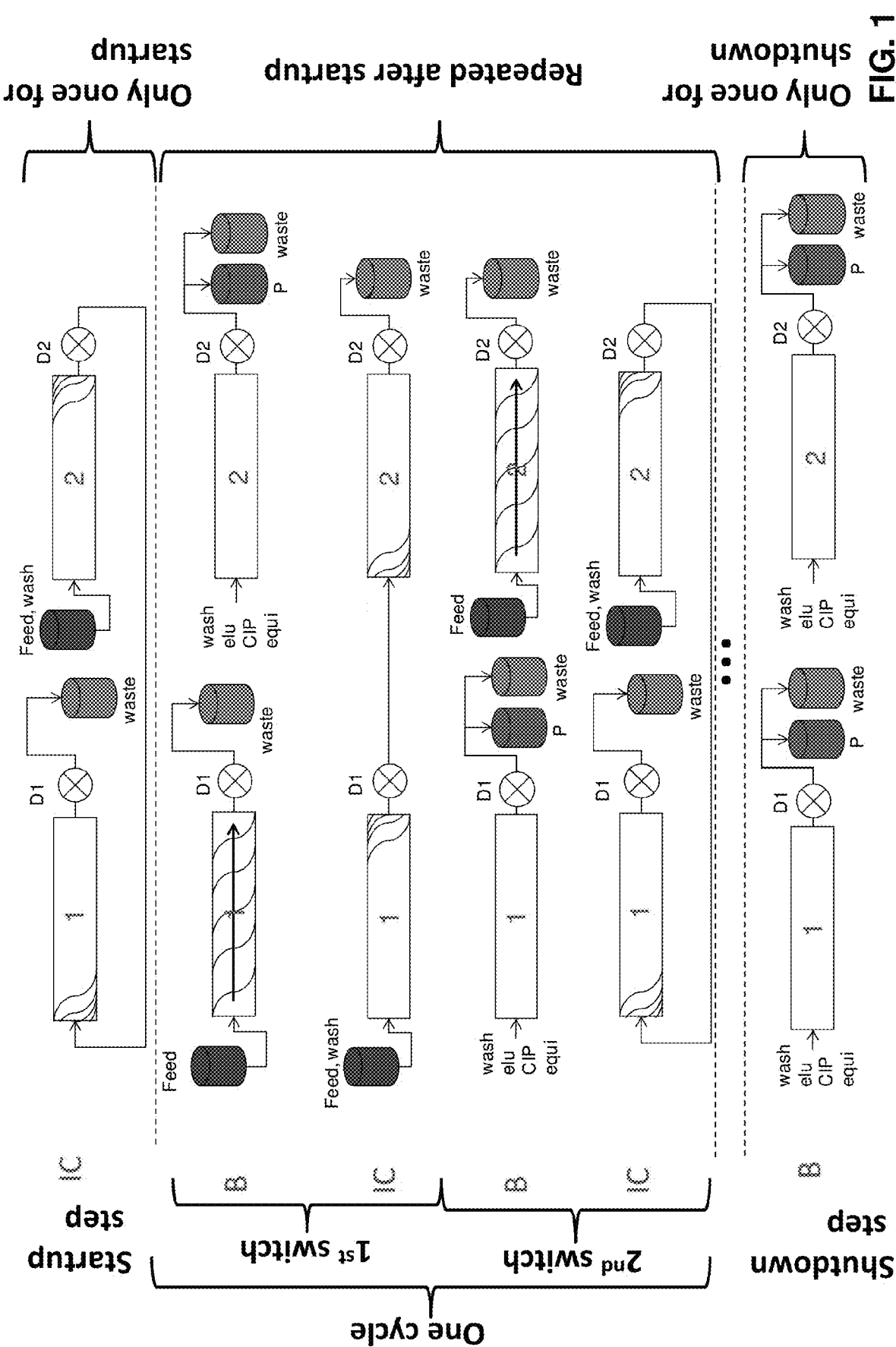
FIG. 1 shows a schematic representation of a twin column countercurrent sequential loading process, where the process comprises an optional startup phase, a cyclic phase and a shutdown phase.
Figure 2:
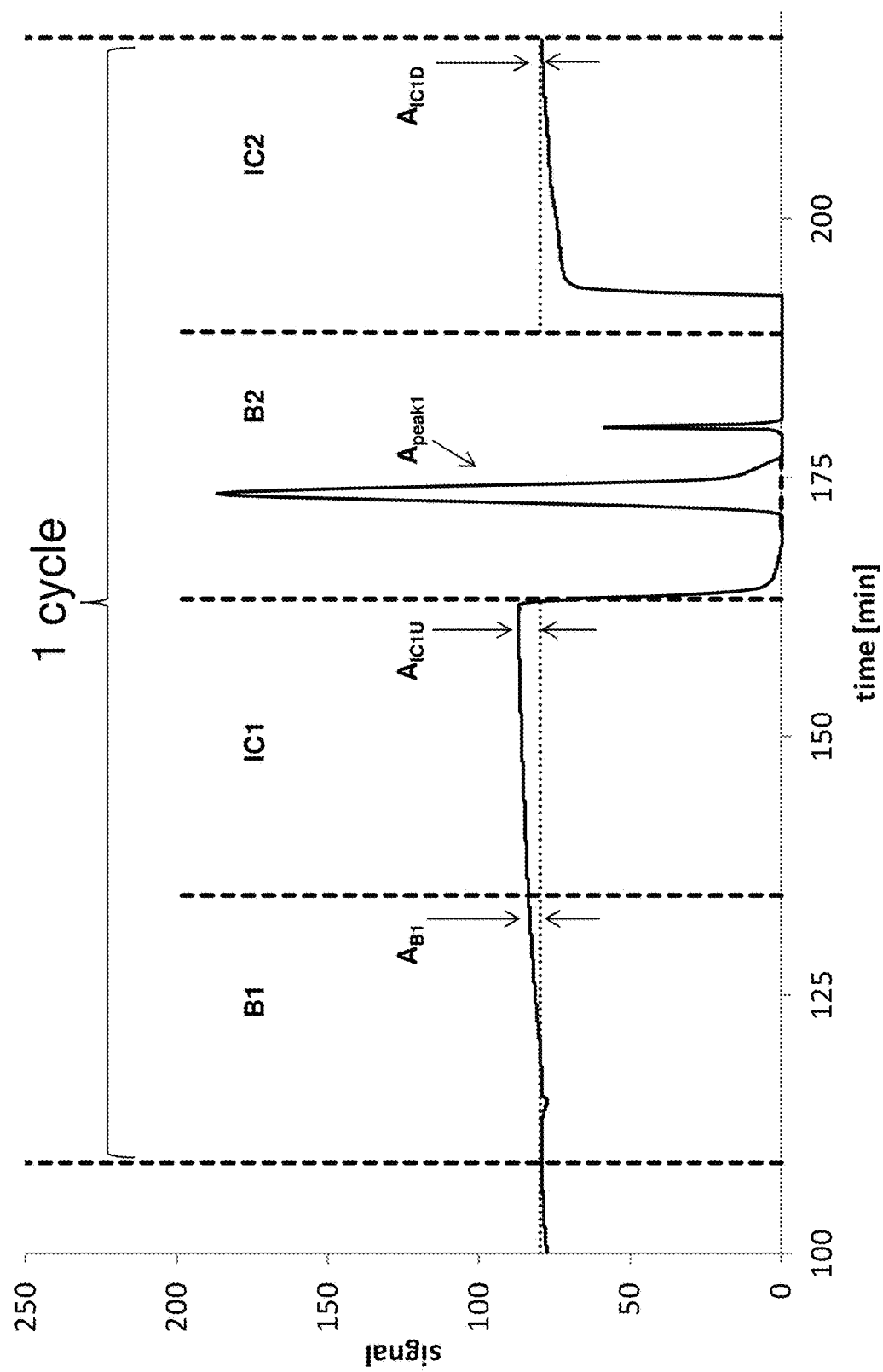
FIG. 2 shows an example of a UV signal recorded at the outlet of column 1 by detector UV1 (black solid line) for the steps in FIG. 1. The plateau value of the non-adsorbing impurities is indicated by horizontal dotted lines.
Figure 3:
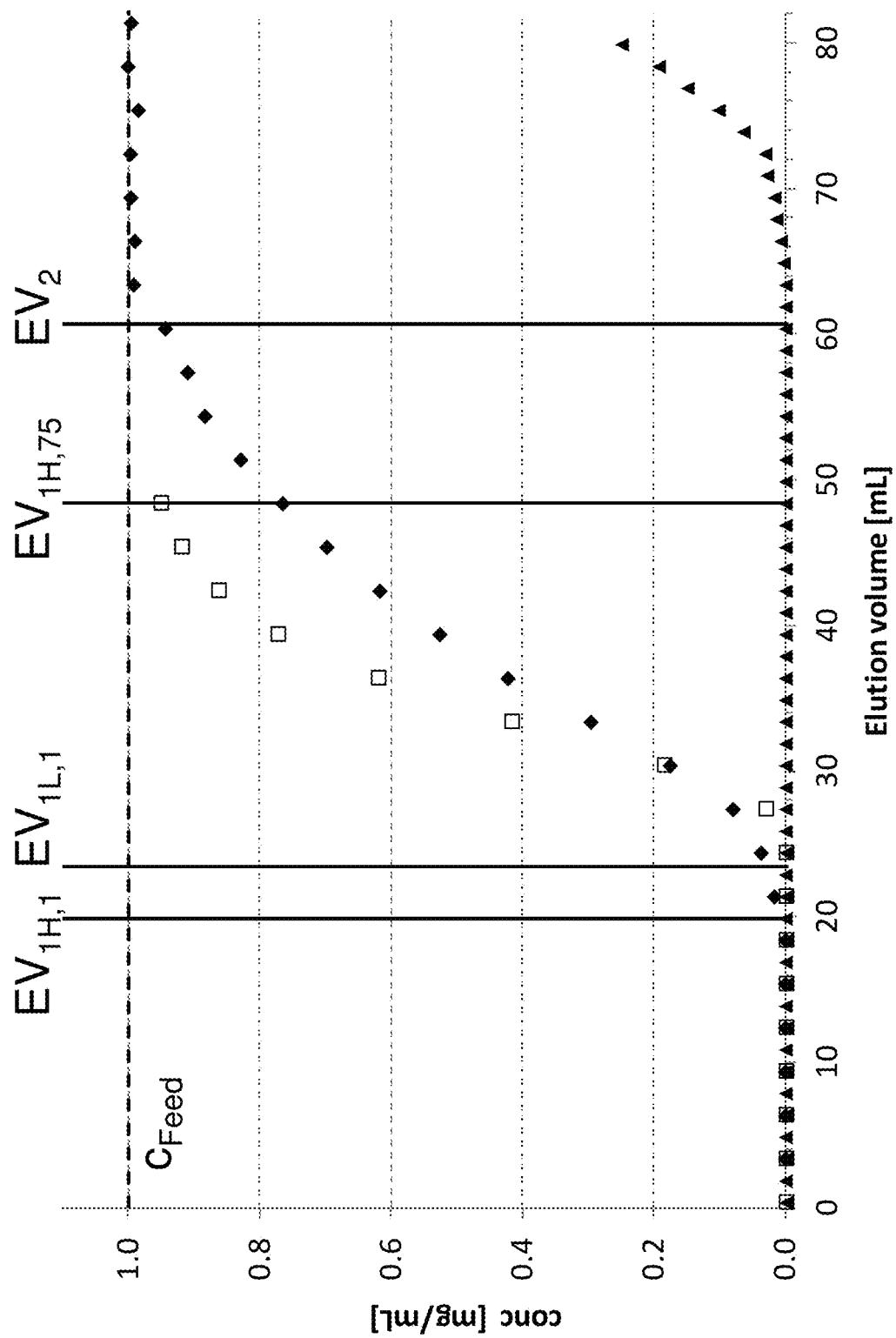
FIG. 3 shows breakthrough curves, wherein diamonds indicate the single column breakthrough curve at high flow rate, squares indicate the single column breakthrough curve at low flow rate, triangles indicate the breakthrough curve from two serially interconnected columns; the elution volumes $EV_{1H,1}$, $EV_{1L,1}$ $EV_{1H,75}$, and $EV_2$ are indicated by solid vertical lines; the feed concentration is indicated by a dashed horizontal line.

An overlay of the offline analysis results together with marks for the elution volume values is provided in FIG. 3. Since $EV_{1H,75}<EV_2$, $EV_Y$ was set equal to $EV_{1H,75}$. The preload value PL was computed by integration approximation using a trapezoid rule to be PL=11.2 g/L and the target load value was determined to be TL=16.3 g/L. The feed flow rate in the disconnected state was determined to be 0.53 mL/min. Since this flow rate was larger than the flow rate used to determine the second breakthrough curve, the latter value was selected as feed flow rate, $Q_{feed,B}$=0.50 mL/min. The duration of the interconnected phase of the sequential loading process was computed to be $t_{IC}$=25 min and the duration of the startup phase was $t_{startup}$=47.5 min. The feed flow rate in both cases was $Q_{feed,startup}=Q_{feed,IC}$=1 mL/min. The interconnected washing step duration was 1 min and the flow rate was $Q_{wash,IC}$.

Example 2: Operation of a Twin Column Countercurrent Sequential Loading Process A twin column countercurrent sequential loading process was used for the capture of an IgG monoclonal antibody from clarified cell culture harvest using a Protein A affinity stationary phase packed into two columns of 0.5 cm inner diameter and 5.0 cm length. The process was operated with the following parameters on Contichrom Lab-10 equipment from ChromaCon AG, Switzerland. The UV detection wavelength was 305 nm. The process was run using the operating parameters determined in example 1, which are summarized in table 1.

TABLE 1

Operating parameters for twin-column countercurrent sequential loading process of example 2 including the startup phase.

| Phase [—] | step [—] | $Q_{buffer}$ [mL/min] | buffer [—] | $Q_{feed}$ [mL/min] | t [min] |
|---|---|---|---|---|---|
| B | wash | 1.0 | 25 mM Phosphate, pH 7.0 | 0.5 | 6.0 |
| | elute | 1.0 | 25 mM Citrate, pH 3.0 | 0.5 | 6.0 |
| | clean | 1.0 | 0.1M NaOH | 0.5 | 7.0 |
| | equilibrate 1 | 1.0 | 25 mM Citrate, pH 3.0 | 0.5 | 3.0 |
| | equilibrate 2 | 1.0 | 25 mM Phosphate, pH 7.0 | 0.5 | 3.0 |
| IC | feed | 0 | — | 1.0 | 25.0 |
| | wash | 1.0 | 25 mM Phosphate, pH 7.0 | 0.0 | 1.0 |
| startup | feed | 0 | — | 1.0 | 47.5 |

$Q_{feed}$ indicates the feed flow rate, $Q_{buffer}$ indicates the flow rate of all other steps; t is the duration of the substeps of the disconnected phase B and the interconnected phase IC, respectively. The parameters for the final elution correspond to the B parameters except for the feed flow rate, which is zero during the final elution step.

The operating parameters of the chromatographic process (such as feed flow rate and switch times) were not changed throughout the run. The feed concentration was artificially increased by approximately 0.01-0.02 g/L every cycle (see table 2) to simulate a subtle change in the upstream process.

After the initial startup phase the purification process was run continuously over five cycles before being eluted in the final elution phase. The effluents corresponding to the feed, the product fraction, the feed flow through fraction and the cleaning fraction were analyzed by offline protein A HPLC analysis in order to determine the IgG concentrations. From the volume of the fractions and the product concentrations, the product masses and performance parameters were computed.

Figure 4:
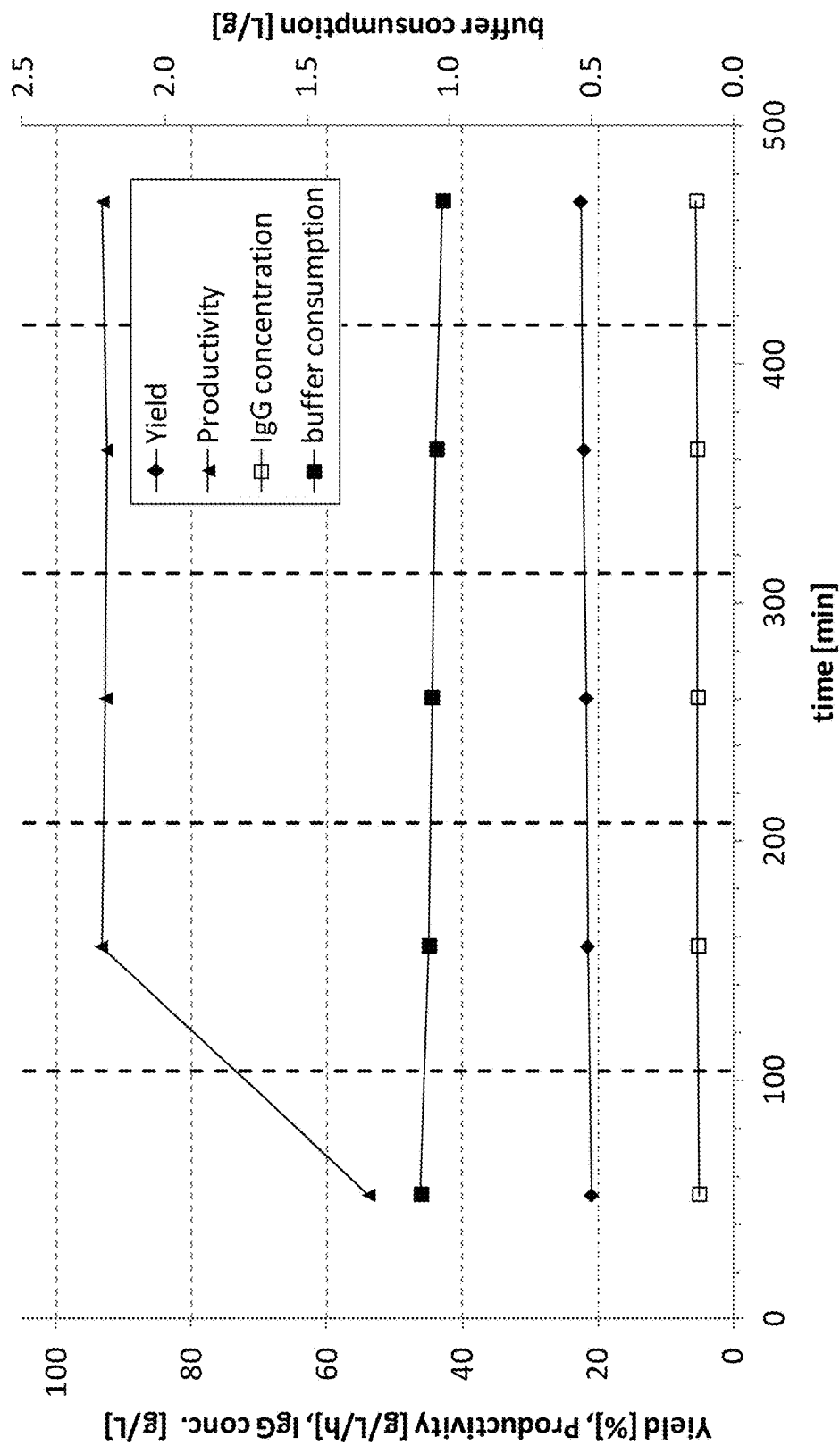
FIG. 4 shows the performance parameters yield, productivity, IgG concentration, and buffer consumption (average values) for the five cycles of the sequential countercurrent loading process of example 2.

The yield was calculated by comparing the product mass in the product fraction with the product mass in the feed fraction. The productivity was calculated by division of the product mass (obtained in one cycle) by the cycle duration and the total column volume (i.e. the volume of the two columns together). The buffer consumption was calculated by dividing the overall volume of buffers used within one cycle by the product mass in the product fraction of that cycle. The feed concentration and the performance parameters are summarized in table 2 and the evolution over time is shown in FIG. 4. The example shows that high yield and productivity values can be obtained using the described process despite subtle changes of the feed concentration.

TABLE 2

Feed concentration, IgG concentration, yield, productivity and buffer consumption of the sequential countercurrent loading process as average values for the five cycles of the process.

| Cycle | feed conc [g/L] | pool conc [g/L] | yield [%] | productivity [g/L/h] | buffer consumption [L/g] |
|---|---|---|---|---|---|
| 1 | 1.01 | 5.10 | 53.8 | 21.0 | 1.1 |
| 2 | 1.03 | 5.24 | 93.3 | 21.5 | 1.1 |
| 3 | 1.04 | 5.28 | 92.6 | 21.7 | 1.1 |
| 4 | 1.06 | 5.37 | 92.6 | 22.1 | 1.0 |
| 5 | 1.08 | 5.49 | 93.1 | 22.6 | 1.0 |

Example 3: Detector Comparison, Low Impurity Signals

A twin column countercurrent sequential loading process was operated with the following parameters on Contichrom Lab-10 equipment from ChromaCon AG, Switzerland. Two detector cells giving different signals for the same sample were used for demonstration.

The operating parameters are summarized in Table 3.

TABLE 3

Operating parameters for twin-column countercurrent sequential loading process of example 3.

| Phase [—] | step [—] | $Q_{buffer}$ [mL/min] | buffer [—] | $Q_{feed}$ [mL/min] | t [min] |
|---|---|---|---|---|---|
| B | wash | 1.0 | 25 mM Phosphate, pH 7.0 | 0.2 | 6.0 |
|   | elute | 1.0 | 25 mM Citrate, pH 3.0 | 0.2 | 6.0 |
|   | clean | 1.0 | 0.1M NaOH | 0.2 | 7.0 |
|   | equilibrate 1 | 1.0 | 25 mM Citrate, pH 3.0 | 0.2 | 3.0 |
|   | equilibrate 2 | 1.0 | 25 mM Phosphate, pH 7.0 | 0.2 | 3.0 |
| IC | feed | 0 | — | 1.0 | 24.0 |
|   | wash | 1.0 | 25 mM Phosphate, pH 7.0 | 0.0 | 1.0 |
| startup | feed | 0 | — | 1.0 | 45.0 |

$Q_{feed}$ indicates the feed flow rate, $Q_{buffer}$ indicates the flow rate of all other steps; t is the duration of the substeps of the disconnected phase B and the interconnected phase IC, respectively. The parameters for the final elution correspond to the B parameters except for the feed flow rate, which is zero during the final elution step. The UV detection wavelength was 300 nm.

Figure 5:
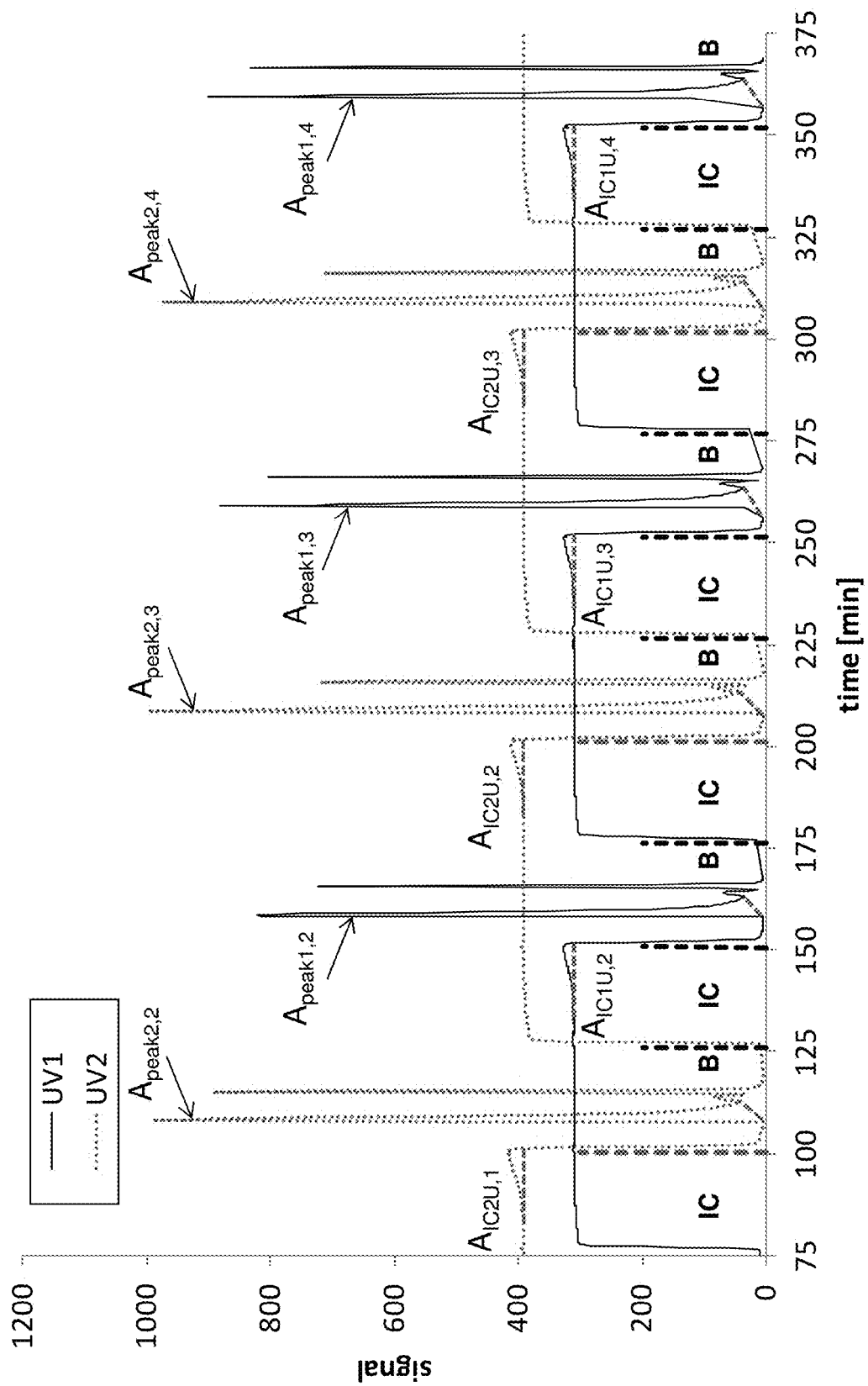
FIG. 5 shows signals recorded during cycles 2, 3, 4 by the two UV detectors (UV1, UV2) positioned at the column outlets of a twin-column sequential loading chromatography process, wherein the interconnected phases are denoted with "IC", the disconnected phases are denoted with "B"; the phase borders are represented by black dashed short vertical lines; the cycle borders are represented by bold dashed long vertical lines; the areas corresponding to the breakthrough from the upstream column are marked with $A_{IC2U,n}$ for UV2 (column 2 is upstream) and $A_{ICiU,n}$ for UV1 (column 1 is upstream), respectively, where n stands for the cycle number; for instance $A_{ICiU,3}$ refers to the area corresponding to the breakthrough from column 1 in the 3rd cycle with column 1 being in the upstream position; the peak areas corresponding to the eluates from the columns that have been in the upstream position in the previous interconnected phases are marked with $A_{peak2,n}$ for UV2 (column 2 was upstream in the previous interconnected phase) and $A_{peak1,n}$ for UV1 (column 1 was upstream in the previous interconnected phase), respectively, where n stands for the cycle number; for instance $A_{peak1,3}$ refers to the area corresponding to the product elution from column 1 in the 3rd cycle; the baselines used for the area determinations are indicated with thin dashed lines.

The chromatograms from the UV detectors UV1 and UV2 located at the outlet of each column, recorded during cycles 2, 3 and 4 are shown in FIG. 5. The process was in cyclic steady state in cycles 3 and 4.

During the interconnected phases, the UV detectors record a signal that corresponds to the load flow-through of the upstream and the downstream column, respectively. The chromatograms of the process in cyclic steady state are explained referring to cycle 2 starting at 100 min.

In the following, the index n is used to describe the n-th cycle of the process. Thus, for instance, the area $A_{peak2,3}$ corresponds to the elution peak area recorded for column 2 (by detector 2) in the $3^{rd}$ cycle.

In the disconnected phase B the product was recovered from column 2. The disconnected phase typically includes at least one washing step prior to elution, and typically a strip and/or clean step followed by at least one re-equilibration step. The product peak is indicated by $A_{peak2,2}$ (recorded by UV2). In parallel to the washing, elution, cleaning and re-equilibration of column 2, column 1 was loaded with feed at lower flow rate as the feed flow rate in the interconnected state. The signal UV1 corresponded to the non-adsorbing impurities that flowed through. The signal reached a constant plateau, indicating that no product was breaking through during the B phase.

In the subsequent interconnected phase IC, the columns were interconnected and column 1 was placed in the upstream position and continued to be loaded. The rising signal (UV1) recorded at the outlet of column 1 at the end of the interconnected phase indicated that product was breaking through ($A_{ICiU,2}$). However, this product was not lost but re-adsorbed in the downstream column 2. While breakthrough was detected at column 1 (UV1), no breakthrough was detected at column 2 (UV2) indicating that the entire product was re-adsorbed. At the end of the interconnected phase B column 1 was washed with fresh buffer such that the product present in the liquid volume of the upstream column 1 was adsorbed in the downstream column 2.

In the following disconnected phase B the product was recovered from column 1 using the same protocol of washing, elution, strip and/or clean, re-equilibration steps that was used in the previous disconnected phase for column 2. The product peak is indicated by $A_{peak1,2}$ (recorded by UV1). At the same time column 2 was loaded with feed at a lower flow rate as the feed flow rate in the interconnected state. The signal UV2 corresponded to the impurities that flowed through. Again, the signal reached a constant plateau, indicating that no product was breaking through.

In the subsequent interconnected phase IC, column 2 was continued to be loaded and the rising signal (UV2) at the end of the interconnected phase indicated that product was breaking through from column 2 ($A_{IC2U,2}$). However, this product was not lost but re-adsorbed in the downstream column. While breakthrough was detected from column 2 (UV2), no breakthrough was detected at column 1 (UV1) indicating that the entire product was re-adsorbed. At the end of the interconnected phase B column 2 was washed with fresh buffer such that the product present in the liquid volume of column 2 was adsorbed in the downstream column 1.

After the interconnected phase had been completed, a new cycle was started.

In the process, before being washed and eluted in the disconnected phase, the respective columns are in the upstream positions in the interconnected phase and loaded such that product is breaking through into the downstream column where it is re-adsorbed (see example 2). The breakthrough in the interconnected phase is proportional to the areas designated with $A_{IC2U,n}$ (UV2, column 2) and $A_{IC1U,n}$ (for UV1, column 1) in FIG. 5, with n as cycle number.

In FIG. 5 furthermore the peak areas corresponding to the elution of the columns in the disconnected phase that have previously been in the upstream position in the interconnected phase are shown and designated $A_{peak1,n}$ (for UV1, column 1) and $A_{peak2,n}$ (UV2, column 2), with n as cycle number. The baselines for the peak areas were drawn from the elution peak start to the UV signal points that corresponded to the end of the elution step in the disconnected state. Since the UV signal was not at zero at this point, the baselines are not horizontal. However, in order to obtain comparable results for $A_{peak}$ it is more important to draw the baseline in a consistent manner for each peak in each cycle rather than drawing a horizontal baseline.

The determined areas are listed in Table 1.

In the ideal case of absolutely identical columns and detectors $A_{IC1U,n}$ (table 4, column 1) would be equal to $A_{IC2U,n}$ (table 4, column 3) and $A_{peak1,n}$ (table 4, column 2) would be equal to $A_{peak2,n}$ (table 3, column 4). In practice both columns and detectors are significantly different, thus in most cases the areas $A_{IC1U}$ and $A_{IC2U}$ are significantly different and the areas $A_{peak1}$ and $A_{peak2}$ are significantly different from each other.

This is confirmed by the ratio $A_{IC2U}/A_{IC1U}$ (table 4, column 5) calculated for every single cycle. The ratio shows that $A_{IC2U}$ in cyclic steady state (cycles 3 and 4) is about 1.3 times larger (30%) than $A_{IC1U}$. In the case of different areas it is very important to determine if the difference is due to a detector with different properties, e.g. amplification, or if it is due to a column with different, potentially deteriorated capacity. Making a judgment based on the different areas alone may lead to the erroneous replacement of a column that actually had an acceptable capacity.

By comparison of the ratios $A_{peak2}/A_{peak1}$ (table 4, column 6) it becomes clear that also $A_{peak2}$ is about 1.3 times larger (30%) than $A_{peak1}$. Also the ratio of the sums of the breakthrough and the peak areas $(A_{IC2U,n}+A_{peak2,n})/(A_{IC1U,n}+A_{peak1,n})$ is about 1.3 (table 3, column 10).

Together, this information shows that the detector signal of UV2 is in general 1.3-fold larger than the detector signal of UV1.

In case the ratios $A_{IC2U}/A_{IC1U}$ and $A_{peak2}/A_{peak1}$ would have been different, it would have indicated that the columns differ in capacity. In that case the ratio of the sums of the breakthrough and the peak areas (table 3, column 10) would have been used to determine the difference of the detector signals.

TABLE 4

Areas and ratios derived from FIG. 5, given in [mAU min]. The columns 5-10 marked with "ratio" represent ratios of values listed in other columns. For instance the ratio 3/1 (column 5) stands for a division of the values of column 3 by the values of column 1 (thus $A_{peak2}/A_{peak1}$)

| cycle | 1 measured $A_{IC1U}$ | 2 measured $A_{peak1}$ | 3 measured $A_{IC2U}$ | 4 measured $A_{peak2}$ | 5 ratio 3/1 | 6 ratio 4/2 | 7 ratio 2/1 | 8 ratio 4/3 | 9 ratio 7/8 | 10 ratio (3 + 4)/(1 + 2) |
|---|---|---|---|---|---|---|---|---|---|---|
| 2 | 128 | 1157 | 189 | 1500 | 1.48 | 1.30 | 9.0 | 7.9 | 1.14 | 1.31 |
| 3 | 111 | 1112 | 149 | 1419 | 1.34 | 1.28 | 10.0 | 9.5 | 1.05 | 1.28 |
| 4 | 113 | 1112 | 146 | 1419 | 1.29 | 1.28 | 9.8 | 9.7 | 1.01 | 1.28 |

Example 4: Column Capacity Monitoring, Low Impurity Signals

The twin column countercurrent sequential loading process of example 3 was evaluated for column capacity changes. The feed was not changed during the run and the feed concentration was constant. Thus only the column capacity was potentially changing, for instance due to fouling or harsh cleaning. The explanations refer to the nomenclature used in FIG. 5.

The fact that $A_{ICiU,n-1}=A_{ICiU,n-1}$ and/or $A_{peaki,n}=A_{peaki,n-1}$ for both columns (see example 2) indicates the column capacity has stayed constant from one cycle to the other.

If $A_{ICiU,n}>A_{ICiU,n-1}$ and/or $A_{peaki,n}<A_{peaki,n-1}$ would have been measured with significant difference it would have been indicative of a decreasing column capacity. Typically the accuracy of the area determination is 1%, thus an increase of $A_{ICiU,n}$ by 1% over $A_{ICiU,n-1}$ or a decrease of $A_{peaki,n}$ by 1% over $A_{peaki,n-1}$ cannot be attributed to a loss of capacity.

The method may be also used to evaluate the column performance of cycles that are not successive.

Example 5: Column Capacity Monitoring, High Impurity Signals

A twin column countercurrent sequential loading process was operated for the capture of a product from feed material with a large impurity content. The feed material was the same throughout the entire run (constant product concentration in feed). The operating parameters are summarized in table 5.

TABLE 5

Operating parameters for twin-column countercurrent sequential loading process of example 5.

| Phase [—] | step [—] | $Q_{buffer}$ [mL/min] | buffer [—] | $Q_{feed}$ [mL/min] | t [min] |
|---|---|---|---|---|---|
| B | wash | 1.0 | 25 mM Phosphate, pH 7.0 | 0.2 | 6.0 |
| | elute | 1.0 | 25 mM Citrate, pH 3.0 | 0.2 | 9.0 |
| | clean | 1.0 | 0.1M NaOH | 0.2 | 7.0 |

TABLE 5-continued

Operating parameters for twin-column countercurrent sequential loading process of example 5.

| Phase [—] | step [—] | $Q_{buffer}$ [mL/min] | buffer [—] | $Q_{feed}$ [mL/min] | t [min] |
|---|---|---|---|---|---|
| | equilibrate 1 | 1.0 | 25 mM Citrate, pH 3.0 | 0.2 | 2.0 |
| | equilibrate 2 | 1.0 | 25 mM Phosphate, pH 7.0 | 0.2 | 4.0 |
| IC | feed | 0 | — | 1.0 | 24.5 |
| | wash | 1.0 | 25 mM Phosphate, pH 7.0 | 0.0 | 1.0 |
| startup | feed | 0 | — | 1.0 | 45.0 |

$Q_{feed}$ indicates the feed flow rate, $Q_{buffer}$ indicates the flow rate of all other steps; t is the duration of the substeps of the disconnected phase B and the interconnected phase IC, respectively. The parameters for the final elution correspond to the B parameters except for the feed flow rate, which is zero during the final elution step. The UV detection wavelength was 305 nm.

Figure 6:
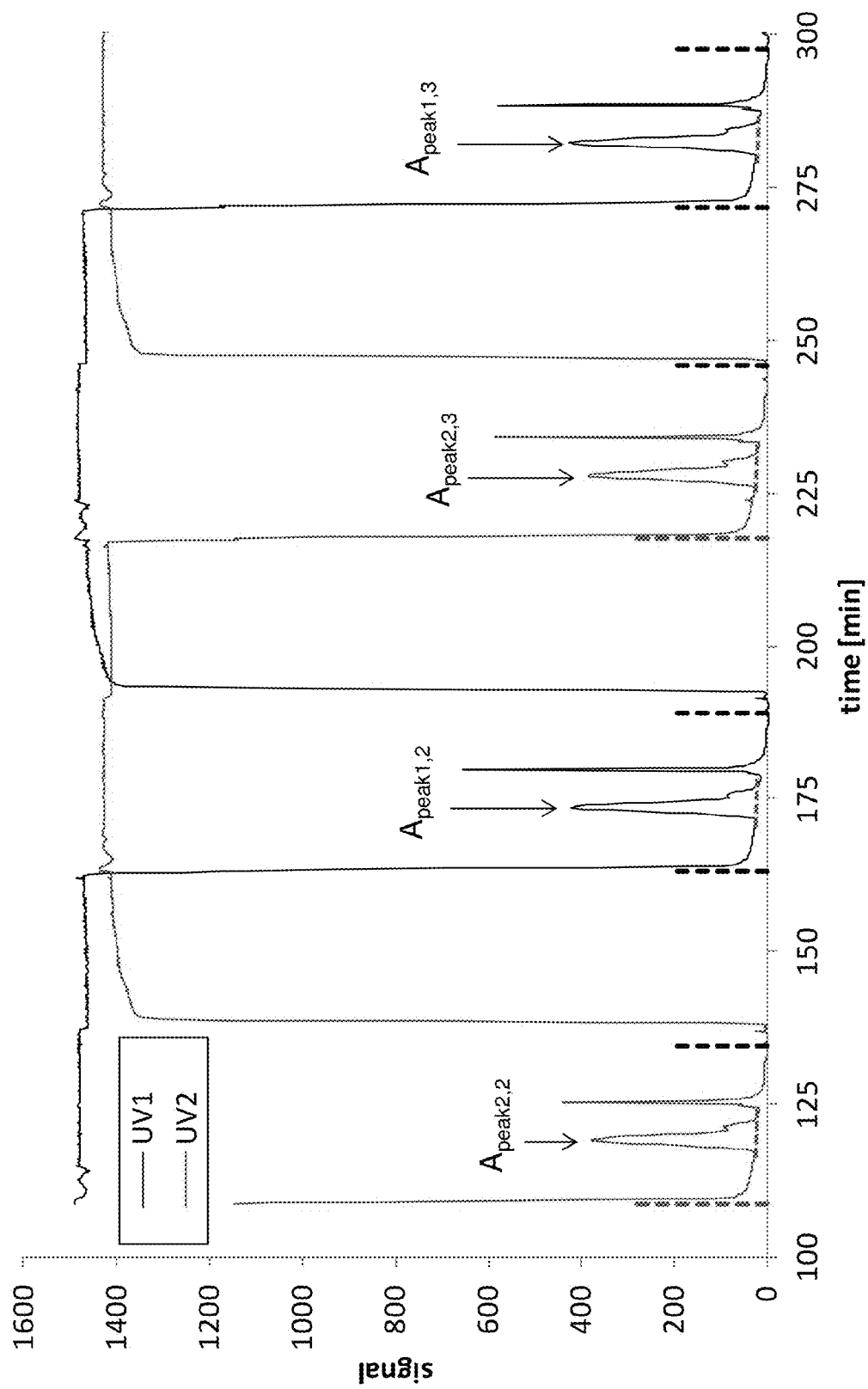
FIG. 6 shows the signals recorded during cycles 2 and 3 by the two UV detectors (UV1, UV2) positioned at the column outlets of a twin-column sequential loading chromatography process; the phase borders are represented by dashed short vertical lines; the cycle borders are represented by dashed long vertical lines; the areas corresponding to the breakthrough of the non-adsorbing impurities cannot be determined due to non-linearity of the detector signal; the peak areas corresponding to the product eluates from the columns that have been in the upstream position in the previous interconnected phases are marked with $A_{peaki2,n}$ for UV2 (column 2 was upstream in the previous interconnected phase) and $A_{peak1,n}$ for UV1 (column 1 was upstream in the previous interconnected phase), where n stands for the cycle number 2 or 3; for instance $A_{peak2,3}$ refers to the area corresponding to the product elution from column 2 in the 3rd cycle; the baselines used for the area determinations are indicated with thin dashed lines.

Due to the large impurity content of the feed material the detectors were in the non-linear range of detection (oversaturated), as shown in FIG. 6, and it was not possible to determine the areas corresponding to the product breakthrough in any of the phases of the process ($A_{ICiU}$, $A_{Bi}$).

However, based only on the peak areas $A_{peaki,n}$ it was possible to determine if the column capacity had deteriorated from one cycle to the other. The product elution peak areas for the 2nd and the 3rd cycle of the process were determined to be $A_{peak2,2}$=756 mAU min, $A_{peak2,3}$=764 mAU min, $A_{peak1,2}$=805 mAU min, $A_{peak1,3}$=809 mAU min. By calculating the ratios $A_{peak2,3}/A_{peak2,3}$ and $A_{peak1,3}/A_{peak1,2}$, respectively, it becomes obvious that the areas are identical with a difference of 1% which corresponds to the accuracy of the area determination. This means that the column capacities are identical with a difference of maximum 1%. This is expected since typically the capacity does not change dramatically within two subsequent cycles. The method may be also used to evaluate the columns performance of cycles that are not successive.

It has to be noted that in the case of large impurity signals it is not possible to decide based on only $A_{peaki}$ data if the capacities of the two columns are different or if the detectors are give different signals for the same product concentrations. However, if $A_{peaki}$ measurements are carried out with a constant feed concentration it can be tested by changing the load L if the load is in the linear range of product adsorption. It is assumed that no dramatic column capacity decrease takes place within $A_{peaki}$ measurements of two cycles. If the load is in the linear of product adsorption and the comparison is made between at least two peak areas $A_{peaki}$ from each detector the detectors signal difference can be determined by forming the average of the ratios of $A_{peak2,n}/A_{peak1,n}$. The detectors signal difference determination becomes more accurate if the comparison $A_{peak2,n}/A_{peak1,n}$ is made for more cycles.

More information on the linear range of product adsorption is provided in example 10.

Example 6: Feed Concentration and Column Capacity Monitoring, Low Impurity Signals The twin column countercurrent sequential loading process of example 3 was evaluated for the effect of product concentration changes in the feed material and simultaneous column capacity changes.

The operating parameters of the chromatographic process (such as feed flow rate and switch times) were not changed over the cycles but the feed concentration is assumed to be variable and the column capacity is assumed to be constant or to decrease. The different scenarios for possible column degradation and potential feed concentration changes are summarized in table 5.

In example 3 the breakthrough areas are the same $A_{ICiU,n}=A_{ICiU,n-1}$ and the peak areas are the same $A_{peaki,n}=A_{peaki,n-1}$ for both columns in two consecutive cycles (3 and 4), indicating that neither the feed quality nor the column performance have significantly decreased from one cycle to the other.

In the following, more examples of relative behavior of $A_{ICiU}$ and $A_{peaki}$ and the possible causes with respect to feed concentration and column capacity are provided.

If $A_{ICiU,n}<A_{ICiU,n-1}$ and $A_{peaki,n}<A_{peaki,n-1}$ is detected the feed concentration must have decreased. The column capacity may have stayed the same from one cycle to the other but may have also decreased. An increasing ratio $A_{peaki,n}/A_{ICiU,n}$ from one cycle to the other is indicative of the column quality staying constant or that the capacity is decreasing to a lesser extent than the column load. A decreasing ratio $A_{peaki,n}/A_{ICiU,n}$ from one cycle to the other is indicative of the column quality staying constant or the capacity decreasing to a stronger extent than the column load.

If $A_{ICiU,n}>A_{ICiU,n-1}$ and $A_{peaki,n}\geq A_{peaki,n-1}$ are measured the feed concentration must have increased from one cycle to the other. The column capacity may have stayed the same from one cycle to the other but may have also decreased. An increasing ratio $A_{peaki,n}/A_{ICiU,n}$ from one cycle to the other is indicative of the column quality staying constant or that the capacity is decreasing to a lesser extent than the column load increases. A decreasing ratio $A_{peaki,n}/A_{ICiU,n}$ from one cycle to the other is indicative of the column quality staying constant or the capacity decreasing to a stronger extent than the column load.

If $A_{ICiU,n}>A_{ICiU,n-1}$ and $A_{peaki,n}<A_{peaki,n-1}$ are measured the column capacity must have decreased. The feed concentration must have changed such that the load was increased to a stronger extent than the capacity of the columns decreased. Theoretically, the capacity of the columns may decrease to the same extent like the increase of the load such that the effects cancel out. In that case it is recommended to calculate the ratio of the areas corresponding to the total product that is eluting for two different cycles, $(A_{peaki,n}+A_{ICiU,n})/(A_{peaki,n-1}+A_{ICiU,n-1})$, for the same detector. If the ratio is >1, the feed concentration must have increased from one cycle to the other.

TABLE 5

Changes in column capacity and feed concentration from cycle n-1 to n and the effects on the areas $A_{ICiU}$ and $A_{peaki}$ that are determined from the chromatograms.

| columns | feed | $A_{ICiU}$ | $A_{peaki}$ |
|---|---|---|---|
| = | = | $A_{ICiU,n}=A_{ICiU,n-1}$ | $A_{peaki,n}=A_{peaki,n-1}$ |
| =/↓ | ↓ | $A_{ICiU,n}<A_{ICiU,n-1}$ | $A_{peaki,n}<A_{peaki,n-1}$ |
| = | ↑ | $A_{ICiU,n}>A_{ICiU,n-1}$ | $A_{peaki,n}\geq A_{peaki,n-1}$ |
| ↓ | = | $A_{ICiU,n}>A_{ICiU,n-1}$ | $A_{peaki,n}<A_{peaki,n-1}$ |
| ↓ | ↑ | $A_{ICiU,n}>A_{ICiU,n-1}$ | effects may cancel out, check $(A_{peaki,n}+A_{ICiU,n})/(A_{peaki,n-1}+A_{ICiU,n-1})$ |

Column capacity changes include: capacity decrease "↓", constant capacity "=";
Product concentration changes in the feed include the following: increase "↑", decrease in "↓", no change "=".

Example 7: Feed Concentration and Column Capacity Monitoring, High Impurity Signals The twin column countercurrent sequential loading process of example 5 was evaluated for the effect of product concentration changes in the feed material and simultaneous column capacity changes. In the following, the product concentration in the feed will abbreviated with "feed concentration"

The operating parameters of the chromatographic process (such as feed flow rate and switch times) were not changed over the cycles but the feed concentration was assumed to be variable and the column capacity is assumed to be constant or to decrease.

Due to the large impurity content of the feed material the detectors were in the non-linear range of detection (oversaturated), as shown in FIG. 6, and it was not possible to determine the areas corresponding to the product breakthrough in any of the phases of the process ($A_{ICiU}$, $A_{Bi}$).

The fact that $A_{peaki,n}=A_{peaki,n-1}$ for both columns indicates that a.) neither the feed concentration nor the column performance have decreased significantly or b.) that the column capacity for both or one of the columns has decreased to the same extent as the feed concentration has increased from cycle n−1 to cycle n.

If $A_{peaki,n}>A_{peaki,n-1}$ is detected for both or one of the columns indicates that the feed concentration has increased from cycle n−1 to n and the column capacity has stayed equal or decreased to a lesser extent as the feed concentration has increased, for both or one of the columns.

If $A_{peaki,n} < A_{peaki,n-1}$ is detected for both or one of the columns, either the feed concentration has decreased from cycle n−1 to n or the column capacity has decreased or both the feed concentration and the column capacity have decreased. Possibly also the feed concentration has increased from cycle n−1 to n but the column capacity has decreased to a stronger extent.

Example 8: Process Control, Low Impurity Signals

Two twin column countercurrent sequential loading processes for the capture of a product from feed material with a large impurity content were evaluated for the effect of product concentration changes in the feed material and simultaneous column capacity changes. In the following, the product concentration in the feed is abbreviated with "feed concentration". The twin-column countercurrent sequential loading process conditions are listed in table 7.

TABLE 7

Operating parameters for the twin-column countercurrent sequential loading processes of example 8.

| Phase [—] | step [—] | $Q_{buffer}$ [mL/min] | buffer [—] | $Q_{feed}$ [mL/ min] | t [min] |
|---|---|---|---|---|---|
| B | wash | 1.0 | 25 mM Phosphate, pH 7.0 | 0.82/0.19 | 6.0 |
|  | elute | 1.0 | 25 mM Citrate, pH 3.0 | 0.82/0.19 | 9.0 |
|  | clean | 1.0 | 0.1M NaOH | 0.82/0.19 | 7.0 |
|  | equilibrate 1 | 1.0 | 25 mM Citrate, pH 3.0 | 0.82/0.19 | 2.0 |
|  | equilibrate 2 | 1.0 | 25 mM Phosphate, pH 7.0 | 0.82/0.19 | 4.0 |
| IC | feed | 0 | — | 1.0 | 24.5 |
|  | wash | 1.0 | 25 mM Phosphate, pH 7.0 | 0.0 | 1.0 |
| startup | feed | 0 | — | 1.0 | 45.0 |

$Q_{feed}$ indicates the feed flow rate, $Q_{buffer}$ indicates the flow rate of all other steps; t is the duration of the substeps of the disconnected phase B and the interconnected phase IC, respectively. $Q_{feed}$ was 0.82 mL/min and 0.19 mL/min, respectively. The parameters for the final elution correspond to the B parameters except for the feed flow rate, which is zero during the final elution step. The UV detection wavelength was 300 nm.

Based on the areas $A_{ICiU}$, $A_{Bi}$ and $A_{peaki}$, control actions can be derived to maintain certain levels of $A_{peaki}$, which correspond to the concentration of the product of interest in the product pool.

As outlined in example 6, $A_{ICiU}$ and $A_{peaki}$ experience certain trends in response to feed concentration and column capacity changes. The aim of process control is to maintain $A_{peaki}$ within certain defined limits. The possible control actions include a change of the load and are listed in detail above.

The control actions based on the trends of the areas $A_{ICiU}$ and $A_{peaki}$ are summarized in the following:

If the feed concentration remains constant and the column quality remains constant no control action is required.

If the feed concentration decreases and the column capacity remains the same or decreases the load L may be increased to increase $A_{peaki}$ (see constraint reported below).

In case the feed concentration is increasing and the column quality remains the same or decreases to a lesser extent, the load L must be reduced to maintain the desired level of $A_{peaki}$.

In case the feed concentration stays equal and the column capacity decreases the load L may be increased to increase $A_{peaki}$ (see constraint reported below).

In case the feed concentration is increasing and the column capacity is decreasing to a larger extent, the load L may be increased to maintain the desired level of $A_{peaki}$, taking into account the constraint explained below.

The above cases show that the effects of column capacity deterioration and feed concentration change in the periodic countercurrent loading process can be controlled by changing only the load. Summarizing the above control actions, if $A_{peaki}$ decreases beyond the specified limits the load should be increased (see constraint below) and if $A_{peaki}$ increases beyond the specified limit the load should be reduced.

The constraint for load increases is given by the dynamic binding capacity. The more the capacities of the downstream column in the interconnected state and of the column that is loaded in the disconnected state are exceeded, the more product is lost and the lower the final recovery of the process.

In order to avoid product losses, the breakthrough of product from the column that is loaded during the disconnected state and the breakthrough of product from the downstream column in the interconnected state must be minimized.

In process chromatograms these constraints imply that the signals from the columns that are loaded during the disconnected state and the signals from the downstream columns in the interconnected state must not exceed the plateau value that corresponds to the level of the impurities which are not adsorbed. This constraint is graphically illustrated in FIG. 7 for chromatograms of the runs with two different loads (run I: 48 g/L, run II: 30 g/L, only the signal of detector UV2 is shown).

Figure 7:
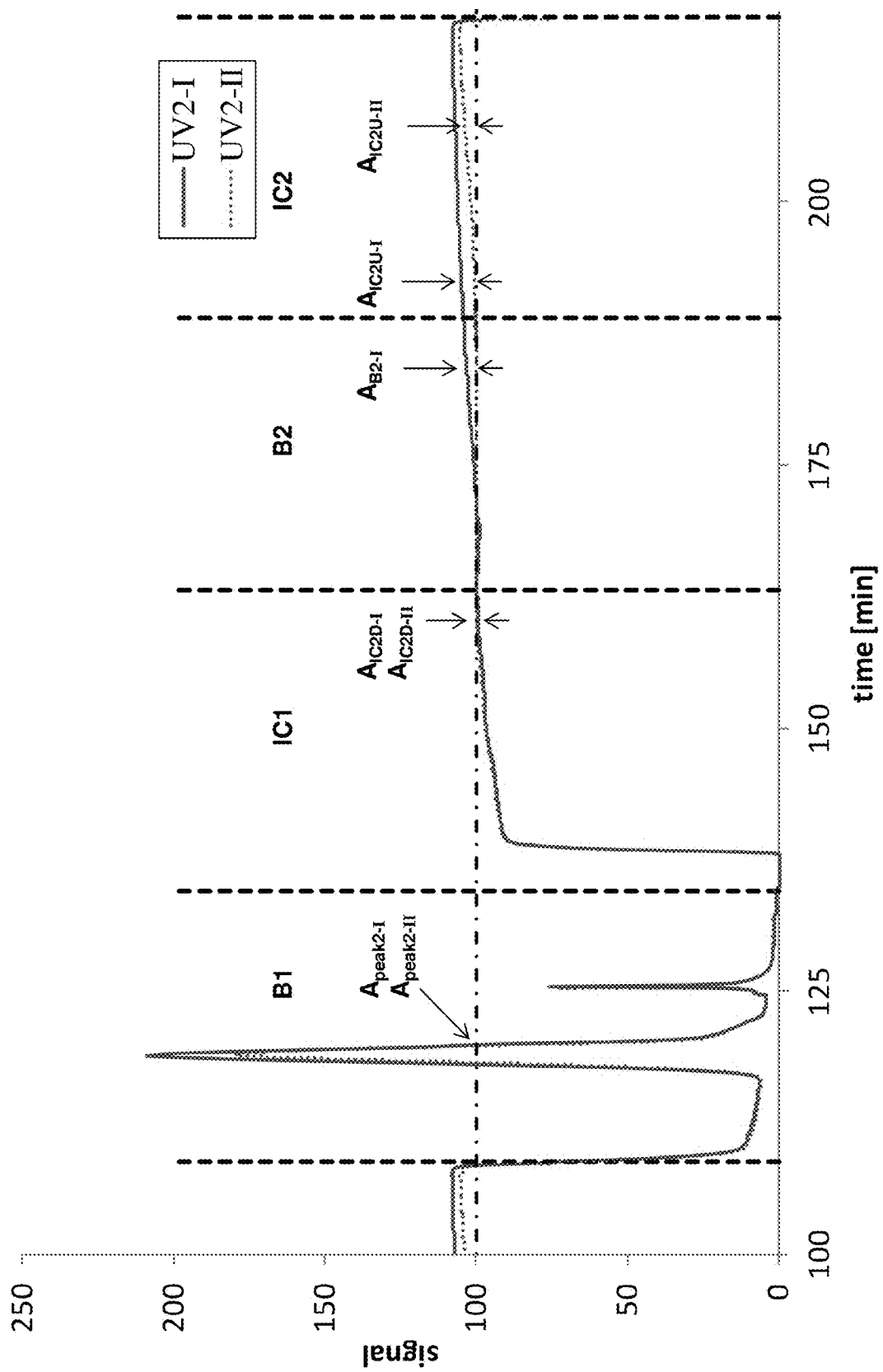
FIG. 7 shows an overlay of signals from two runs of a twin-column sequential loading chromatography process recorded by the UV detector UV2 during one cycle (B1, IC1, B2, IC2); for the sake of simplicity the cycle index n is omitted; the signal of the first run (UV2-I, full line) corresponds to operating parameters with a load of 48 g/L, the signal of the second run (UV2-II, dotted line) corresponds to operating parameters with a load of 30 g/L (decreased feed flow rate in the disconnected state); the interconnected phases are denoted with "IC", the disconnected phases are denoted with "B"; the phase borders are represented by black dashed vertical lines. The plateau value of the non-adsorbing impurities is indicated by a horizontal dashed-dotted line. The areas referred to in the example 8 description are indicated by arrows.

FIG. 7 shows that the signals from the downstream column in the interconnected phase IC1 (UV2-I and UV2-II) reach the plateau value that corresponds to the non-adsorbing impurities (see arrows in FIG. 7 in phase IC1 for both 30 g/L and 48 g/L load). Thus the areas $A_{IC2D-I}$ and $A_{IC2D-II}$ confined by the signal curve and the impurity plateau baseline are not larger than zero and no product is lost in either of the runs during the interconnected state from the downstream column.

In the disconnected phase B2 the area in between the breakthrough curve and the impurity plateau baseline is zero for run II (area not indicated in FIG. 7 since the signal curve and the impurity plateau baseline match exactly). Thus, in run I, no product is eluted into the waste (and lost) during the B phase. In contrast, for run I, the area indicated with $A_{B2-I}$ is larger than zero and corresponds to product breakthrough in the loading step of the disconnected phase (i.e. product loss).

In the interconnected phase IC2 the areas in between the signal curve of the upstream column in the interconnected state and the impurity plateau baseline are designated $A_{IC2U-I}$ and $A_{IC2U-II}$, respectively. In phase IC2 the breakthrough from the previously loaded column either starts (30 g/L load, UV2-II) or respectively continues (48 g/L load, UV2-I), however the column is in the upstream position and the product leaving the column is completely adsorbed in the downstream column. Therefore the product that corresponds to the areas $A_{IC2U-I}$ and $A_{IC2U-II}$, recorded at the upstream column outlet in the interconnected phase, remains in the system and is not lost.

The area values, obtained by integration, that correspond to product losses are listed in Table 8.

In order to estimate if the product losses were significant in cyclic steady state the areas $A_{ICiD}$ and $A_{Bi}$ were compared with the respective elution peak areas $A_{peaki}$ by calculating the product loss ratios PLR1=$(A_{B1}+A_{IC1D})/(A_{peak1}+A_{B1}+A_{IC1D})$ for column 1 (signals not shown in FIG. 7) and PLR2=$(A_{B2}+A_{IC2D})/(A_{peak2}+A_{B2}+A_{IC2D})$ for column 2 using the area values listed in Table 8 for each of the runs I and II. In this case, since $A_{IC1D}=A_{IC2D}=0$ for both runs I and II, the equations can be facilitated to PLR1=$A_{B1}/(A_{peak1}+A_{B1})$ and PLR2=$A_{B2}/(A_{peak2}+A_{B2})$. The average product loss ratio was then calculated as PLRavg=(PLR1+PLR2)/2. For the run with the 48 g/L load, it was found that PLR1 was 14.5% and PLR2 was 11.4% and the average ratio PLRavg was about 13%, indicating a significant product loss. The corresponding product yield was Y=100%−PLRavg=87%. In contrast, all product loss ratios for the 30 g/L run (run II) were zero due to $A_{B1}=A_{B2}=0$ and consequently the yield was 100%.

The yield values were confirmed by offline HPLC protein A analytics to be 90% (run I) and 100% (run II), which is in good agreement with the values determined by the online area evaluation. In the presented case the evaluation was carried out online by manual integration using the Contichrom evaluation software (ChromaCon AG, Zurich, Switzerland) but it can be fully automated using suitable integration algorithms and automatically trigger control actions for the subsequent cycles.

Consequently, based on the online analysis results, in run I the load would be lowered by means of a suitable control action in order to avoid product losses in future cycles. Possible control actions include but are not limited to a reduction of the feed flow rate in the disconnected state, a reduction of the feed flow rate in the interconnected state and a reduction of the interconnected state duration, as described further above.

It is worth noting that depending on the individual column capacity and detector calibration, the areas $A_{B1}$ and $A_{B2B}$ may be significantly different. In order to reliably estimate if potential product losses are significant and require control actions, the areas $A_{B1}$ and $A_{B2}$ are put into perspective with the corresponding peak areas $A_{peak1}$ and $A_{peak2}$, respectively, and an average product loss ratio should be estimated based on both columns/detectors. The same applies for the areas $A_{IC1D}$ and $A_{IC2D}$. Furthermore it is worth noting that if $A_{B1}$ and $A_{B2}$ are zero, also $A_{IC1D}$ and $A_{IC2D}$ must be zero (see run II case).

TABLE 6

Data from the cyclic steady state from two operating points of twin-column sequential loading chromatography process. Run I: 48 g/L load, run II: 30 g/L load. The determined areas correspond to the areas indicated in FIG. 7 for UV2. The areas for UV1 were evaluated too but are not shown in FIG. 7 for clarity. Column 2 shows the feed flow rate in the disconnected state of the process.

| 1 Run | 2 $Q_{feedJC}$ [mL/min] | 3 Load [g/L] | 4 UV1 $A_{peak1}$ [mAU*min] | 5 $A_{B1}$ [mAU*min] | 6 $A_{IC1D}$ [mAU*min] | 7 UV2 $A_{peak2}$ [mAU*min] |
|---|---|---|---|---|---|---|
| I | 0.82 | 48 | 344 | 58.3 | 0 | 379 |
| II | 0.19 | 30 | 253 | 0.1 | 0 | 282 |

| 1 Run | 8 $A_{B2}$ [mAU*min] | 9 $A_{IC2D}$ [mAU*min] | 10 avg product loss ratio [%] | 11 Yield (online) [%] | 12 Yield (offline) [%] |
|---|---|---|---|---|---|
| I | 49 | 0 | 13.0 | 87.0 | 90.5 |
| II | 0 | 0 | 0.0 | 100.0 | 100.0 |

Example 9: Optimization of a Twin Column Countercurrent Sequential Loading Process, Low Impurity Signals In order to optimize process performance it is desirable to maximize the load of the run in order to process more material in the same amount of time using the same columns.

In the previous examples suitable criteria for the identification of product losses have been explained in detail. The criteria can serve as optimization tool since they define the maximum load of the process. Based on the criteria, the load of the process may be increased just until the point where product losses start to occur.

A twin column countercurrent sequential loading process was run for the capture of an IgG monoclonal antibody from clarified cell culture harvest using a Protein A affinity stationary phase packed into two columns of 0.5 cm inner diameter and 5.0 cm length in order to demonstrate the optimization procedure.

The process was operated with the parameters listed in table 9 on Contichrom Lab-10 equipment from ChromaCon A. G., Switzerland.

TABLE 9

Operating parameters for the twin-column countercurrent sequential loading process of example 9.

| Phase [—] | step [—] | $Q_{buffer}$ [mL/min] | buffer [—] | $Q_{feed}$ [mL/min] | t [min] |
|---|---|---|---|---|---|
| B | wash | 1.0 | 25 mM Phosphate, pH 7.0 | 0.0/0.19/0.43/0.62/0.82 | 6.0 |
|   | elute | 1.0 | 25 mM Citrate, pH 3.0 | 0.0/0.19/0.43/0.62/0.82 | 9.0 |
|   | clean | 1.0 | 0.1M NaOH | 0.0/0.19/0.43/0.62/0.82 | 7.0 |
|   | equilibrate 1 | 1.0 | 25 mM Citrate, pH 3.0 | 0.0/0.19/0.43/0.62/0.82 | 2.0 |
|   | equilibrate 2 | 1.0 | 25 mM Phosphate, pH 7.0 | 0.0/0.19/0.43/0.62/0.82 | 4.0 |
| IC | feed | 0 | — | 1.0 | 24.5 |
|   | wash | 1.0 | 25 mM Phosphate, pH 7.0 | 0.0 | 1.0 |
| startup | feed | 0 | — | 1.0 | 45.0 |

$Q_{feed}$ indicates the feed flow rate, $Q_{buffer}$ indicates the flow rate of all other steps; t is the duration of the substeps of the disconnected phase B and the interconnected phase IC, respectively. $Q_{feed}$ was increased every two cycles. The parameters for the final elution correspond to the B parameters except for the feed flow rate, which is zero during the final elution step. The UV detection wavelength was 300 nm.

The same feed material was used throughout the run. The feed flow rate in the interconnected state was kept constant throughout the run at 1.0 mL/min.

The load flow rate in the disconnected phase was increased after every two cycles in steps from 0.0 mL/min to 0.82 mL/min (see Table 10, column 1). The flow rates corresponded to loads of 26 g/L to 48 g/L (see Table 10, column 2). For column 1, the areas $A_{peak1}$, $A_{B1}$, $A_{IC1D}$ were determined (see Table 10, columns 3-5) and for column 2, the areas $A_{peak2}$, $A_{B2}$ and $A_{IC2D}$ were determined (see Table 10, columns 6-8) as described in example 3 (Note: for 26 g/L load the areas of UV2 were not determined).

From the determined areas from UV1 and UV2, the average product loss ratios PLRavg and the yields were calculated (see Table 10, columns 9, 10). For comparison, the yield was determined by offline HPLC analysis (see Table 10, column 11). The productivity (see Table 10, column 12) was calculated as the amount of product produced within one cycle divided by the duration of the cycle and the total column volume based on the offline analysis values.

The buffer consumption (see Table 10, column 13) was calculated as the amount of buffer consumed (in liters) per gram of product purified based on the offline analysis values.

Figure 8:
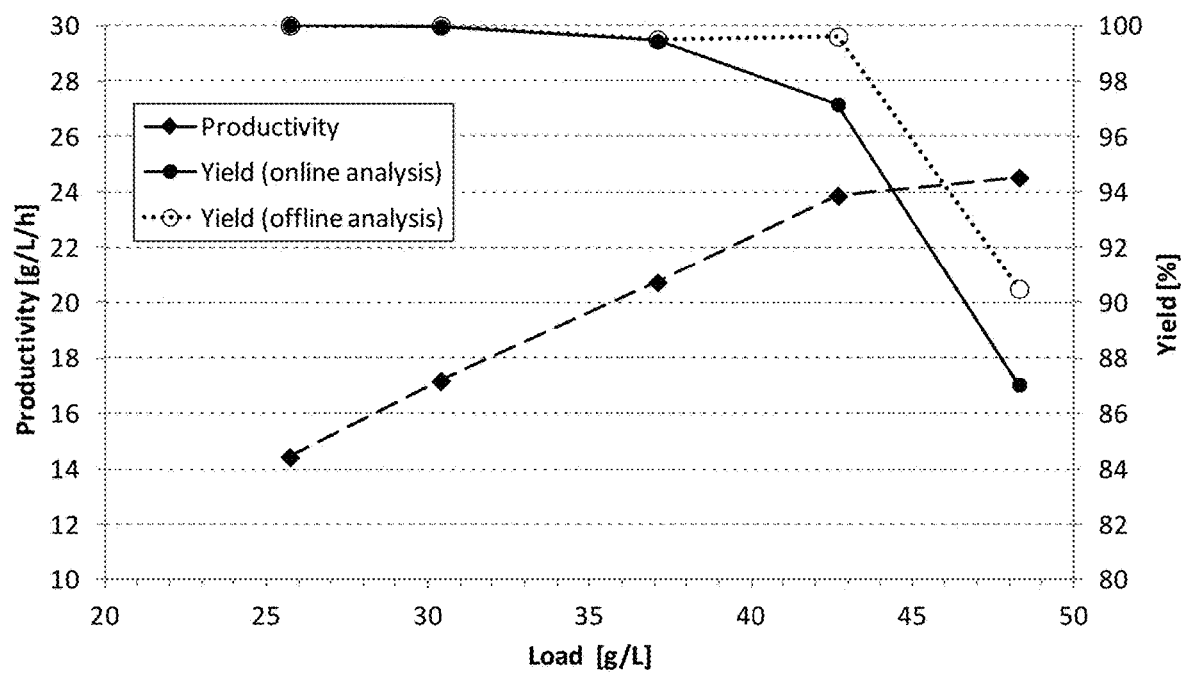
FIG. 8 shows the productivity (diamonds) and yield determined by the optimization method described in example 9 (full circles) and by offline HPLC analyses (empty circles) as a function of the load.

Table 10 shows that with increasing load the productivity increases significantly and the buffer consumption decreases. Increasing the load from 26 g/L to 43 g/L, which corresponds to an increase of more than 65%, still allows for product recovery with more than 97% yield. A further increase of the load to 48 g/L leads to significant product losses of at least 10%, resulting in a product yield of less than 90%. In the presented case, losses of more than 5% were considered inacceptable, so of the tested conditions 43 g/L was the optimal load that had a 65% larger productivity than the base case at 26 g/L and an over 65% reduced buffer consumption. Process yield, determined by online and offline analysis and the productivity are shown as a function of the load in FIG. 8.

Summarizing, the presented example shows how the sequential loading process can be optimized by increasing the load successively and by monitoring and evaluating the areas under the signal curves corresponding to the positions of potential product loss.

The effect of a load increase control action becomes evident in the following cycle, potentially allowing for a new control action. In the presented example, the feed concentration was constant but the optimization method can also be applied if the feed concentration changes or the column capacity is different among the columns and/or the capacity of the columns is decreasing. The method can be fully automated using suitable integration algorithms and automatically trigger control actions for the subsequent cycles. Preferably the step size for load increase for process optimization is in the range of 5-10 g/L for an IgG capture using Protein A affinity chromatography. Through successive increase of the load the process the operating space corresponding to high yield is explored. As soon as an operating point with inacceptable yield is found, the process conditions should be reverted to a previous operating point that corresponded to 100% yield. The peak area of detector i corresponding to the highest possible load at 100% yield is called $A_{peaki,max}$. If desired, the process optimization can be continued by increasing the load again by smaller increments or a load safety margin can be left by not continuing the optimization.

Preferably the process optimization is started from a point that corresponds to an intermediate load. However, if only very little process knowledge is present an optimization starting point is defined by operating parameters corresponding to 0 g/L load in the disconnected phase.

TABLE 10

Optimization procedure data of the twin-column sequential loading chromatography process (example 9). Column 1 shows the feed flow rate in the disconnected state of the process; column 2 the load; columns 3-5 the areas $A_{peak1}$, $A_{B1}$, $A_{IC1D}$, respectively, of UV1 determined in the 2nd cycle after the feed flow rate change; columns 6-8 the areas $A_{peak2}$, $A_{B2}$, $A_{IC2D}$, respectively, of UV2 determined in the 2nd cycle after the feed flow rate change; column 9 the average product loss ration PLRavg, column 10 the yield determined online by the area evaluation method described in the example, column 11 the yield determined through HPLC offline analysis, column 12 the productivity and column 13 the buffer consumption based on the offline analyses.

| 1 | 2 | 3 UV1 | 4 UV1 | 5 UV1 | 6 UV2 | 7 UV2 |
|---|---|---|---|---|---|---|
| 0.00 | 26 | 219 | 0 | 0 | n.a. | n.a. |

TABLE 10-continued

Optimization procedure data of the twin-column sequential loading chromatography process (example 9). Column 1 shows the feed flow rate in the disconnected state of the process; column 2 the load; columns 3-5 the areas $A_{peak1}$, $A_{B1}$, $A_{IC1D}$, respectively, of UV1 determined in the 2nd cycle after the feed flow rate change; columns 6-8 the areas $A_{peak2}$, $A_{B2}$, $A_{IC2D}$, respectively, of UV2 determined in the 2nd cycle after the feed flow rate change; column 9 the average product loss ration PLRavg, column 10 the yield determined online by the area evaluation method described in the example, column 11 the yield determined through HPLC offline analysis, column 12 the productivity and column 13 the buffer consumption based on the offline analyses.

| 1 Q [mL/min] | 2 Load [g/L] | 3 $A_{peak1}$ [mAU*min] | 4 $A_{B1}$ [mAU*min] | 5 $A_{IC1D}$ [mAU*min] | 6 $A_{peak2}$ [mAU*min] | 7 $A_{B2}$ [mAU*min] | 8 UV2 $A_{IC2D}$ [mAU*min] | 9 avg product loss ratio [%] | 10 Yield (online) [%] | 11 Yield (offline) [%] | 12 Prod. [g/L/h] | 13 B.C. [L/g] |
|---|---|---|---|---|---|---|---|---|---|---|---|---|
| 0.00 | | | | | | | | 0.0 | 100.0 | 100.0 | 14.4 | 1.2 |
| 0.19 | 30 | 253 | 0.1 | 0 | 282 | 0 | 0 | 0.0 | 100.0 | 100.0 | 17.2 | 1.0 |
| 0.43 | 37 | 298 | 1.7 | 0 | 326 | 2 | 0 | 0.6 | 99.4 | 99.5 | 20.7 | 0.6 |
| 0.62 | 43 | 330 | 10.5 | 0 | 359 | 10 | 0 | 2.8 | 97.2 | 99.6 | 23.9 | 0.4 |
| 0.82 | 48 | 344 | 58.3 | 0 | 379 | 49 | 0 | 13.0 | 87.0 | 90.5 | 24.5 | 0.2 |

Example 10: Process Control, High Impurity Signals

The example describes the control of the twin column countercurrent sequential loading process for the capture of a product from feed material with a large impurity signal (see FIG. 6) and variable concentration of product of interest throughout the entire run.

As shown in example 5, $A_{B1}$ and $A_{IC1D}$) as well and $A_{B2}$ and $A_{IC2D}$ cannot be measured due to the large impurity signal.

However in the frequently observed case of an only slowly decreasing column capacity, and with implemented safety margins for the load it can be assumed that no product is lost during in the twin-column periodic countercurrent process. Safety margins can be determined by means of offline analysis for product concentration determination. Thus, with reference to example 9, $A_{B1}$ and $A_{IC1D}$) as well and $A_{B2}$ and $A_{IC2D}$ can be assumed to be zero.

In the described case the area $A_{peaki}$ changes only in dependence of the load, for instance due to a change of the feed concentration.

Consequently, based on only the peak areas $A_{peaki}$ and the comparison of their development over at least two cycles, the process performance can be monitored and control actions can be derived to maintain certain levels of $A_{peaki}$, which correspond to the desired concentration of the product of interest in the product pool.

In case the feed concentration remains constant the peak areas $A_{peaki}$ remain constant over the cycles ($A_{peak1,n}=A_{peak1,n-1}$ and $A_{peak2,n}=A_{peak2,n-1}$) and no control action is required. In case the feed concentration increases, the peak areas $A_{peaki}$ increase over the cycles ($A_{peak1,n}>A_{peak1,n-1}$ and $A_{peak2,n}>A_{peak2,n-1}$), and a decrease of the load is required if the peak areas have run out of specification.

In case the feed concentration decreases, the peak areas $A_{peaki}$ decrease over the cycles ($A_{peak1,n}<A_{peak1,n-1}$ and $A_{peak2,n}<A_{peak2,n-1}$), and an increase of the load is required if the peak areas have run out of specification.

The control actions may be also based on comparing areas of non-successive cycles or fractions of cycles.

Example 11: Optimization of a Twin Column Countercurrent Sequential Loading Process, High Impurity Signals The example describes the optimization of a twin column countercurrent sequential loading process for the capture of a product from feed material with a large impurity signal (see FIG. 6) and a constant concentration of product of interest throughout the entire run. The optimization method is described based on the experimental data shown in example 9 without using the values of the areas $A_{B1}$, $A_{IC1D}$ and $A_{B2}$, $A_{IC2D}$ in order to simulate the presence of a large impurity signal as described in example 5.

However in order to optimize process performance it is desirable to maximize the load in order to process more material in the same amount of time using the same columns.

A successive increase of the load inevitably leads to product losses when the column capacity is exceeded. Due to the large impurity signal product losses cannot be directly identified by the areas $A_{B1}$, $A_{IC1D}$ and $A_{B2}$, $A_{IC2D}$, respectively.

Nevertheless, process optimization based only on the peak areas $A_{peaki}$ is possible, when evaluating the peak areas of operating points with different loads.

Figure 9:
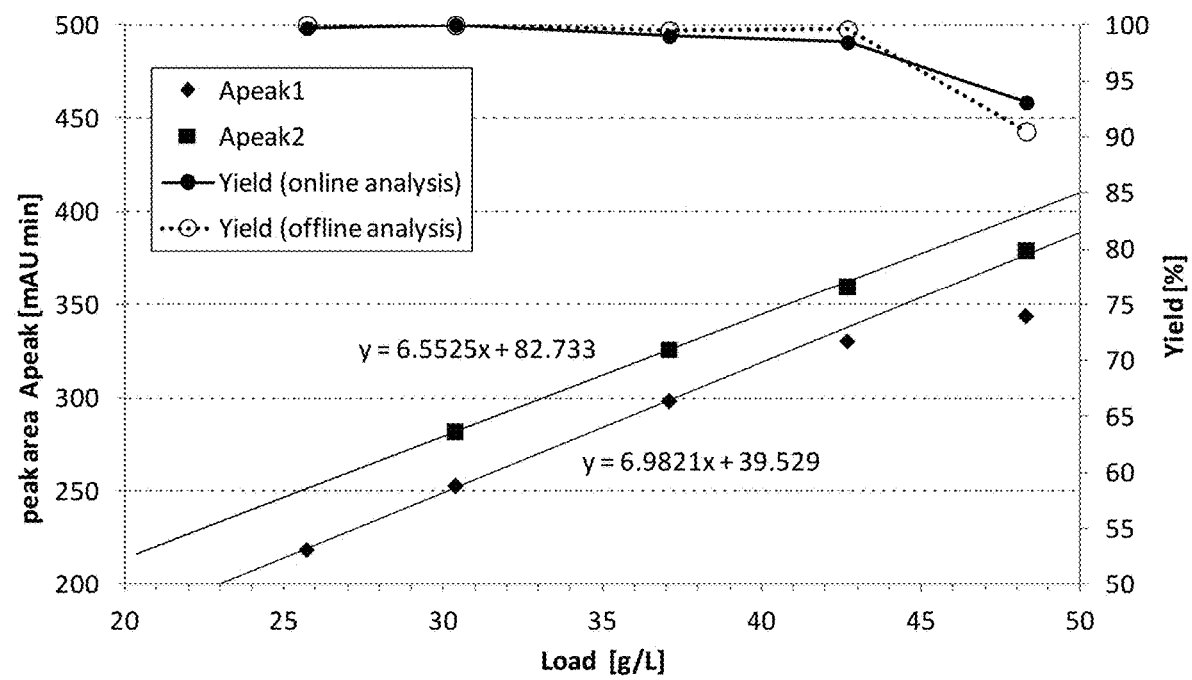
FIG. 9 shows the peak area values $A_{peak}$ from UV1 (diamonds) and UV2 (squares) according to example 11 as a function of the load; the values corresponding to the three lowest loads (UV1) and the two lowest loads (UV2), respectively, were fitted using linear functions (equations displayed in FIG. 9); in addition, the yield determined by the optimization method described in example 11 (full circles) and by offline HPLC analyses (empty circles) is shown as a function of the load.

The starting point of the process optimization corresponded to a load where no breakthrough was present, namely to a load during the interconnected state that corresponds to a value that is well below the breakthrough value of two sequential columns and with a feed flow rate of zero during the disconnected state. The starting load value corresponded to 26 g/L (see table 11, column 2). As described in example 9 the load was now increased every two cycles and the areas $A_{peaki}$ were determined by integrating the chromatograms (table 11, column 3 (UV1) and column 6 (UV2)). After having recorded the peak areas $A_{peaki}$ corresponding to three loads (26 g/L, 30 g/L and 37 g/L) and two loads ($A_{peak2}$, 30 g/L, 37 g/L, the peak area from the first load was not measured), respectively, the area values were plotted as a function of the load and the data was fitted with two straight lines (see FIG. 9). The fact that the peak areas $A_{peak1}$ could be fitted with a straight line indicates that starting at 26 g/L additional product loaded led to a proportional increase of the peak areas $A_{peak1}$, or in other words that all additional product that is loaded is also adsorbed and that the product losses are negligible. In the presented case, the linear correlation of $A_{peak1}$ from 26 g/L to 37 g/L justified also the use of a linear correlation of $A_{peak2}$, which was determined using only two points (30 g/L, 37 g/L). The obtained linear correlations between peak areas and load were used to extrapolate the expected peak areas for higher loads (table 11 column 4 (UV1) and column 7 (UV2)). Further points at increased load were recorded and the determined peak areas were compared to the expected peak areas calculated by means of the correlation. At 43 g/L and 48 g/L load the measured area was smaller than the area predicted by means of the correlation. The occurrence of a difference is expected at higher loads since the stationary capacity is limited, which is not taken into account by the linear correlation. The area difference (UV delta) between the expected and measured peak areas is shown in table 11, column 5 (UV1) and column 8 (UV2). The average product loss ratio (PLR) can now be calculated by dividing UV delta by the corresponding expected peak area for each UV and by forming the average of the values of UV1 and UV2. The yield (online, determined by the presented optimization method, see table 11 column 10) can be calculated by 100%—PLR or by taking the average of the ratio of measured and expected peak area of the two detectors. For comparison, the yields determined using offline HPLC analyses are also shown (see FIG. 9). A comparison of the two yields (online, offline) shows that the chosen optimization method based on evaluation of only the peak areas was capable of identifying loads that corresponded to negligible product losses and such loads that corresponded to larger product losses. Based on both the presented optimization method and offline analyses the operating point with 48 g/L load would have been ruled out due to inacceptable product losses (>5%) and the operating point corresponding to 43 g/L would have been chosen. As described in example 9, the 43 g/L load corresponded to a 65% larger productivity than the base case at 26 g/L load and to an over 65% reduced buffer consumption.

It has to be noted that it is not possible to decide based on only $A_{peaki}$ data if the capacity of the two columns is different or if the detectors have a different signal magnitude. However, if $A_{peaki}$ measurements are carried out with a constant feed concentration in the linear region of the measurement range and the comparison is made between more than two peak areas $A_{peaki}$ from each detector, as outlined in this method, information on both detector calibration and column capacity decrease can be obtained.

Summarizing, the presented example shows how the sequential loading process can be optimized by changing the load and monitoring and evaluating only the peak areas without the need to evaluate areas under breakthrough curves. For this method information of successive cycles is required to determine if the column capacity has been exceeded. The advantage of the method is that it can also be applied in cases where the impurity signal is exceeding the measurement range of the detector. It is recommended to dynamically verify the performance data corresponding to historical operating points if the process is operated over time spans where significant column degradation is expected. For this purpose the load may be changed temporary.

Both presented optimization methods (example 9 and example 11) do not require detector calibration.

TABLE 11

Optimization procedure data of the twin-column sequential loading chromatography process (example 11). Column 1 shows the feed flow rate in the disconnected state of the process; column 2 the load; column 3 the area $A_{peaki}$ determined by integration of the chromatogram of UV1; column 4 the area $A_{peaki}$ as estimated from the linear correlation described in the example and in FIG. 9 for UV1; column 5 the difference between the two areas of column 4 and column 3 of UV1; column 6 the area $A_{peaki}$ determined by integration of the chromatogram of UV2; column 7 the area $A_{peaki}$ as estimated from the linear correlation described in the example and in FIG. 9 for UV2; column 8 the difference between the two areas of column 7 and column 6 of UV2; column 9 the average product loss ration PLRavg, column 10 the yield determined online by the area evaluation method described in the example, column lithe yield determined through HPLC offline analysis, column 12 the productivity and column 13 the buffer consumption based on the offline analyses.

| 1<br>Q<br>[mL/min] | 2<br>Load<br>[g/L] | 3<br>UV1<br>$A_{peak1}$<br>[mAU*min] | 4<br>UV1 expctd<br>$A_{peak1}$<br>[mAU*min] | 5<br>UV1 delta<br>[mAU*min] | 6<br>UV2<br>$A_{peak2}$<br>[mAU*min] | 7<br>UV2 expctd<br>$A_{peak2}$<br>[mAU*min] |
|---|---|---|---|---|---|---|
| 0.00 | 26 | 219 | 219 | 1 | n.a. | 251 |
| 0.19 | 30 | 253 | 252 | −1 | 282 | 282 |
| 0.43 | 37 | 298 | 299 | 0 | 326 | 326 |
| 0.62 | 43 | 330 | 338 | 8 | 359 | 362 |
| 0.82 | 48 | 344 | 377 | 33 | 379 | 399 |

| 1<br>Q<br>[mL/min] | 8<br>UV2 delta<br>[mAU*min] | 9<br>avg product<br>loss ratio<br>[%] | 10<br>Yield<br>(online)<br>[%] | 11<br>Yield
(offline)
[%] | 12
Prod.
[g/L/h] | 13
B.C.
[L/g] |
|---|---|---|---|---|---|---|
| 0.00 | n.a. | 0.3 | 99.7 | 100.0 | 14.4 | 1.2 |
| 0.19 | 0 | −0.2 | 100.0 | 100.0 | 17.2 | 1.0 |

TABLE 11-continued

Optimization procedure data of the twin-column sequential loading chromatography process (example 11). Column 1 shows the feed flow rate in the disconnected state of the process; column 2 the load; column 3 the area $A_{peaki}$ determined by integration of the chromatogram of UV1; column 4 the area $A_{peaki}$ as estimated from the linear correlation described in the example and in FIG. 9 for UV1; column 5 the difference between the two areas of column 4 and column 3 of UV1; column 6 the area $A_{peaki}$ determined by integration of the chromatogram of UV2; column 7 the area $A_{peaki}$ as estimated from the linear correlation described in the example and in FIG. 9 for UV2; column 8 the difference between the two areas of column 7 and column 6 of UV2; column 9 the average product loss ration PLRavg, column 10 the yield determined online by the area evaluation method described in the example, column lithe yield determined through HPLC offline analysis, column 12 the productivity and column 13 the buffer consumption based on the offline analyses.

| 0.43 | 0  | 0.1 | 99.0 | 99.5 | 20.7 | 0.6 |
| 0.62 | 3  | 1.5 | 98.5 | 99.6 | 23.9 | 0.4 |
| 0.82 | 20 | 6.9 | 93.1 | 90.5 | 24.5 | 0.2 |

The twin column sequential process can be transformed into a somewhat simplified process by removing the interconnected phases, leaving only the batch phases (see FIG. 10), leading to the above-mentioned tandem process. The capacity utilization and of this tandem process is lower than the values of the sequential loading process with interconnected phases, however, this tandem process can be realized with simpler equipment and the common property of two identical columns that are loaded alternatingly remains conserved. Moreover the concept of peak area evaluation and comparison of peak areas for control and optimization purposes is equally applicable to a tandem process.

The tandem process generally speaking thus operates in a cyclic manner wherein one cycle comprises the following alternating phases:

A first batch phase B1 wherein the columns are disconnected and the column that has been previously cleaned and re-equilibrated is loaded using a constant feed flow rate or a feed flow rate profile, and wherein the column that has been previously loaded performs the tasks of a typical chromatographic cycle that follow the feeding step (such as washing, elution, cleaning, re-equilibration);

A second batch phase B2 where the functions are switched, i.e. wherein the columns are disconnected and the column that has been previously cleaned and re-equilibrated is loaded using a constant feed flow rate or a feed flow rate profile, and wherein the column that has been previously loaded performs the tasks of a typical chromatographic cycle that follow the feeding step (such as washing, elution, cleaning, re-equilibration).

What is also possible in view of the above is that the recovery of second column includes a preloading with feed. In the context of this application therefore the regeneration phase of the second column may also include, after at least one of the steps of cleaning, equilibration, a final step of loading with feed so as to preload the second column.

Figure 10:
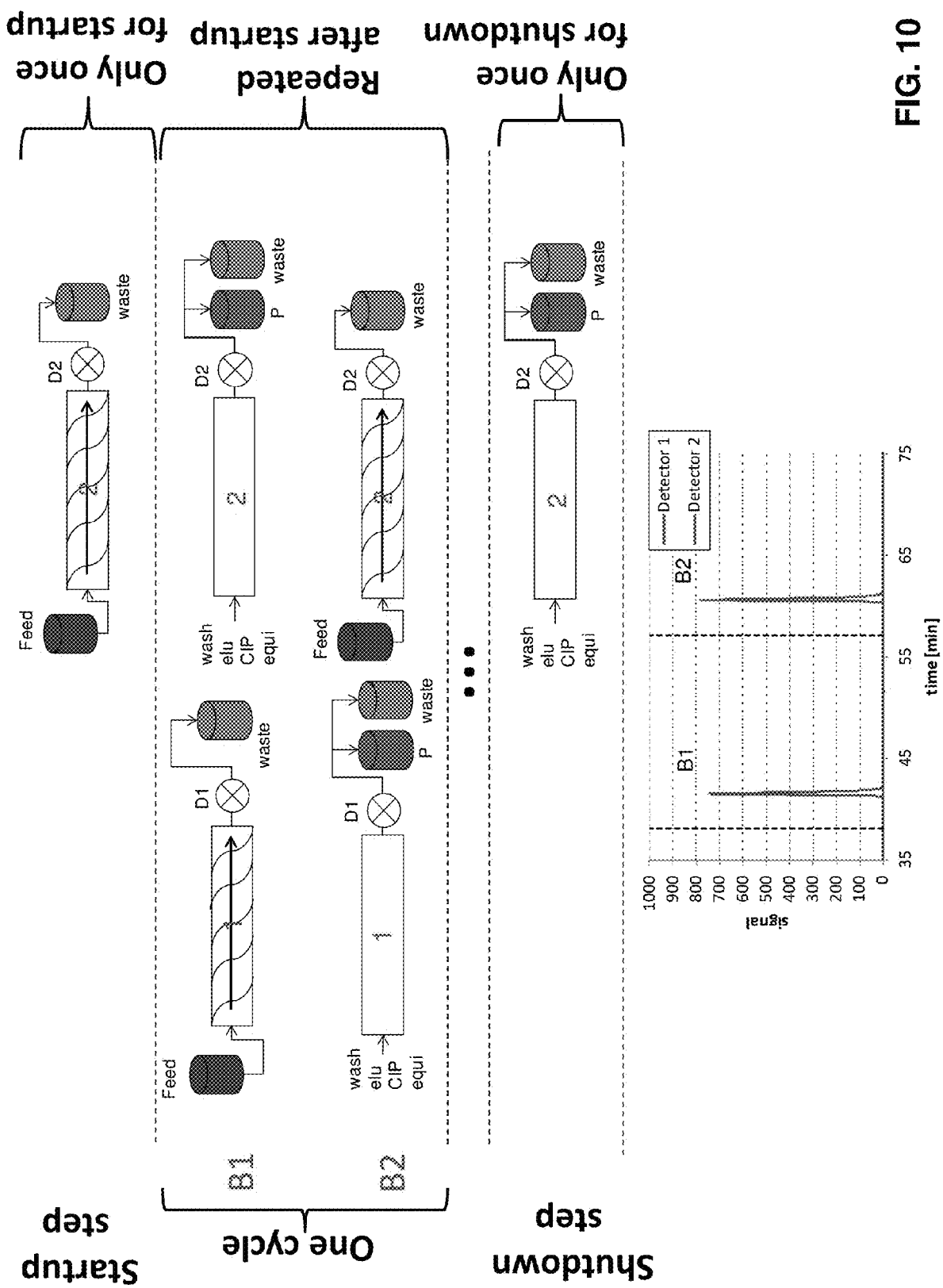
FIG. 10 shows a schematic representation of a twin column tandem process.

On the bottom of FIG. 10 the detector signal recorded by detectors D2 and D1 at the outlets of columns 2 and 1, respectively, at two sequential steps B1 and B2 in one cycle are illustrated. The corresponding areas below the signals correspond to $A_{peaki,n}$. If the corresponding column is in the feed position, the detector detects the area $A_{Bi,n}$, confined by the breakthrough curve and a horizontal baseline, in case the impurity baseline signal is low. In case the impurity baseline signal is high, $A_{Bi,n}$ may not be accessible to measurement. If the corresponding column is in the position for product recovery the detector detects $A_{peaki,n}$ of the product elution peak. $A_{Bi}$ and/or $A_{peaki}$ are then compared for cycles n and n−1, being important for the monitoring/optimization/control process, whereby n−1 represents an earlier cycle of process or a combination of earlier cycles.

The first cycle is usually preceded by a startup step, in which the two columns are disconnected and the column that performs the tasks of a typical chromatographic cycle that follow the feeding step (such as washing, elution, cleaning, re-equilibration) in the next phase B1 is loaded and the other column is idle or being prepared. The last cycle is followed by a shutdown step, in which the two columns are disconnected, and the column that has been loaded in the previous phase B2 performs the tasks of a typical chromatographic cycle that follow the feeding step (such as washing, elution, cleaning, re-equilibration) while the other column is idle, cleaned or is stored.

In order to maintain a high product yield in a tandem process it is usually the aim to minimize $A_{Bi,n}$, which corresponds to product losses.

An analogous form of control and optimization as detailed above for the sequential loading process with alternating disconnected and interconnected phases can be applied to the tandem process as illustrated in FIG. 10. In both cases the processes are started with a certain load that corresponds to the desired load in the case of process control and to a lower load (normally less than 80% of the maximum expected load) in the case of process optimization, respectively. Once in cyclic steady state, which is characterized by essentially identical areas from cycle to cycle, the process control or optimization, respectively, is started. A check is performed if the feed amount to be processed has been consumed. In case of availability of feed, internal chromatogram integrations are performed to determine the signals relevant for the control/optimization. While the control/optimization of the process with alternating interconnected and disconnected phases is based on the determination of $A_{peaki}$, $A_{Bi}$ and $A_{ICi}$ in the case of low impurity signals and $A_{peaki}$ only in the case of high impurity signals (see schematic flow diagram illustration in FIG. 11a), the process control/optimization of the tandem process is based on determination of $A_{peaki}$ and $A_{Bi}$ in the case of low impurity signals and $A_{peaki}$ only in the case of high impurity signals (see FIG. 11b).

Figure 11A:
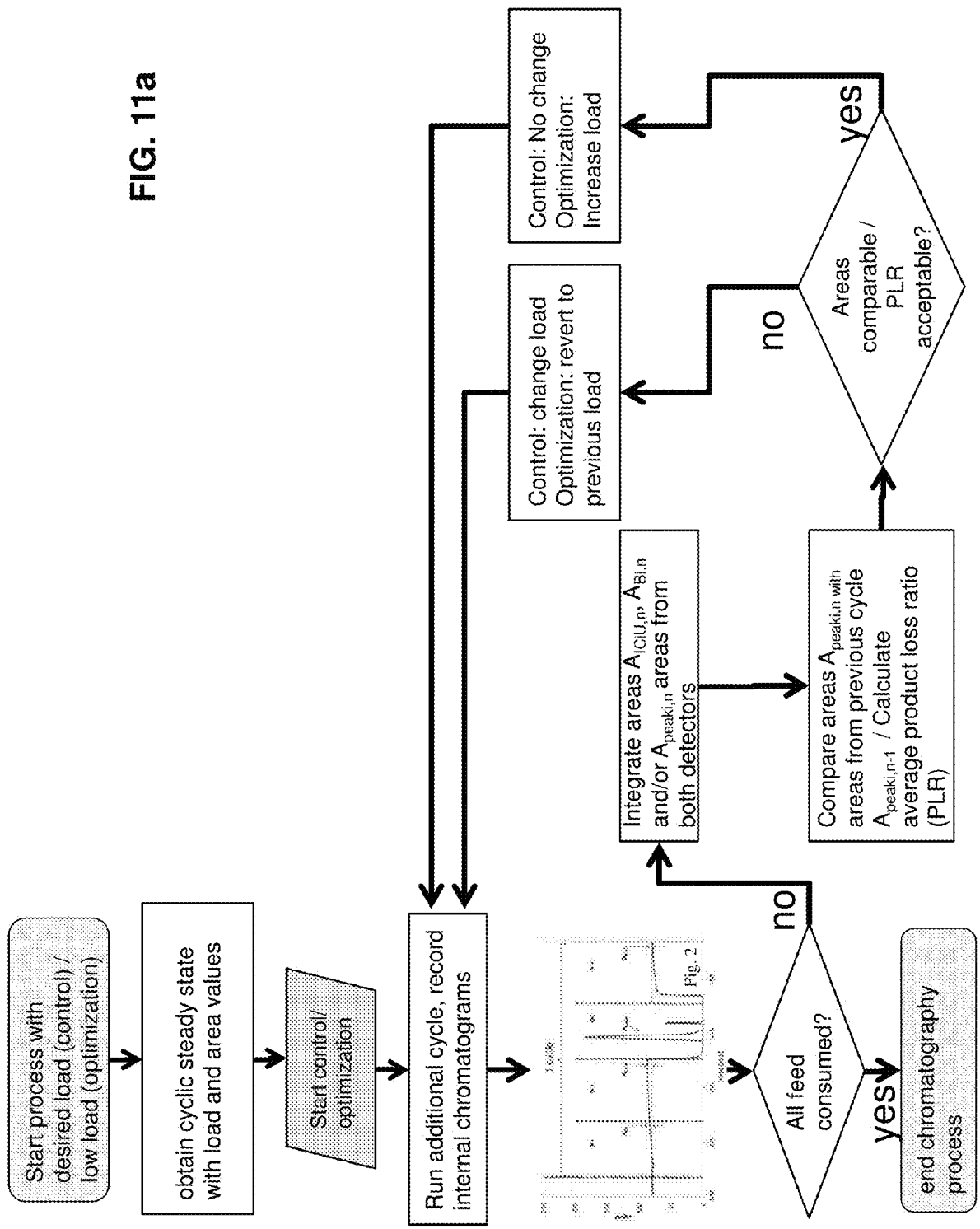
FIGS. 11a, 11b and 11c show (a) a schematic flow diagram for the control and/or monitoring and/or optimization of the process including interconnected states (b) a schematic flow diagram for the control and/or monitoring and/or optimization of a process without interconnected state in tandem operation and (c) a schematic flow diagram for the control and/or monitoring of the process including interconnected states.
Figure 11B:
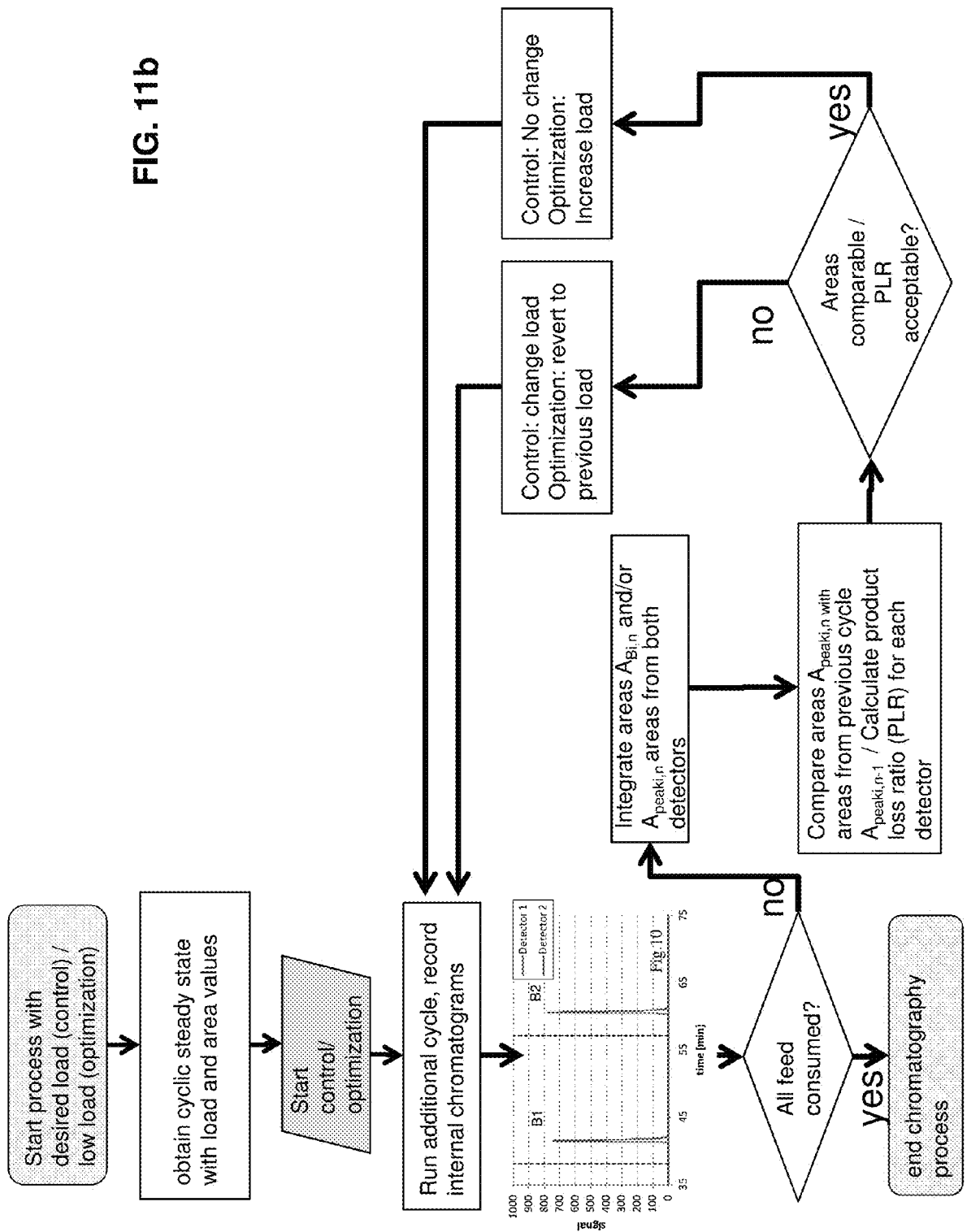
Figure 11C:
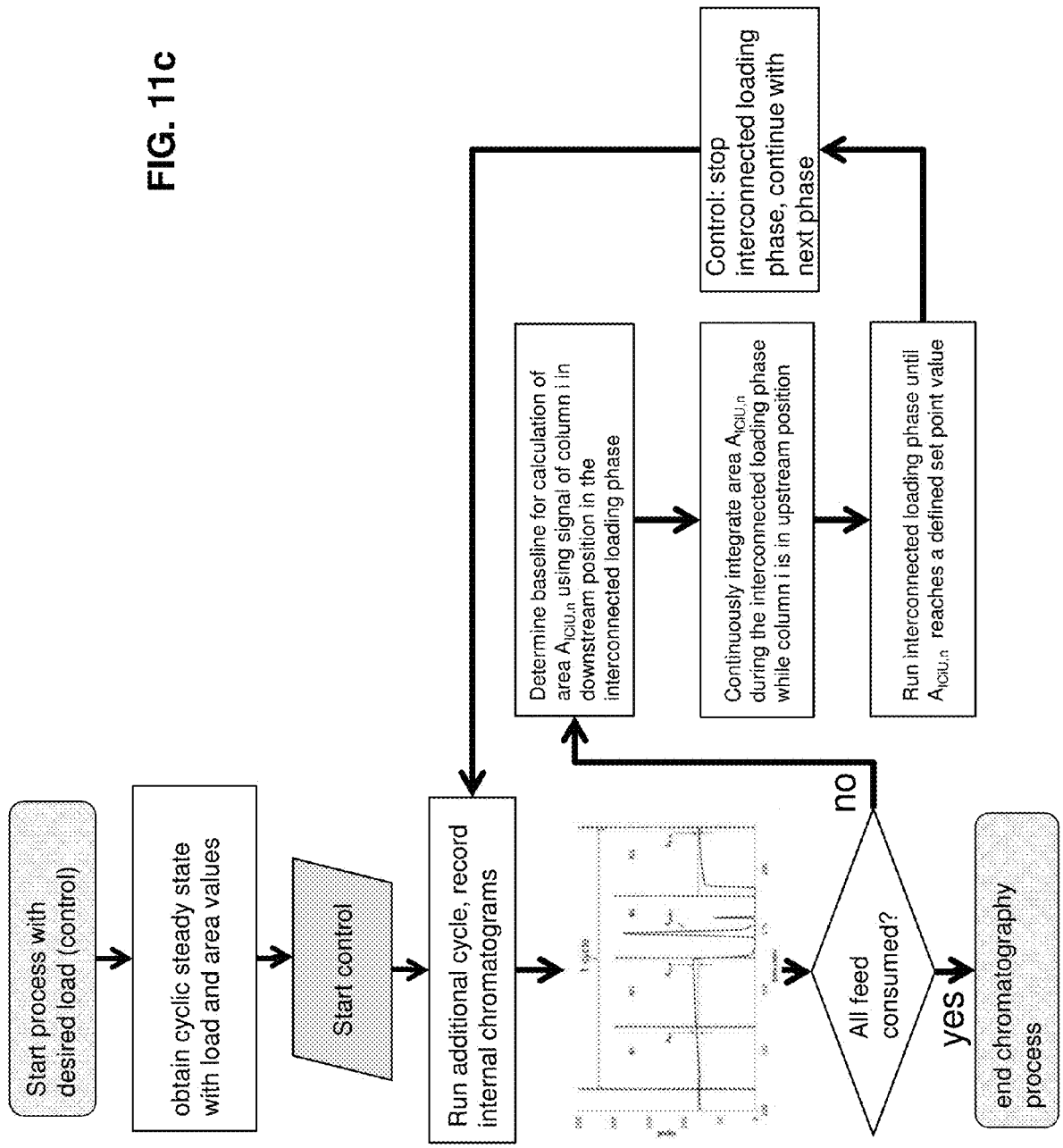

The determined areas are then compared among the detectors for the current and/or previous cycles and/or for the same detector for the current and previous cycles in the case of the process with alternating interconnected and disconnected phases (see FIG. 11a). In the case of the process with disconnected phases only the determined areas are then compared for the same detector for the current and previous cycles (see FIG. 11b). Preferably, the areas are compared by calculating a product loss ratio (PLR) or by forming the ratios between the areas determined in previous cycles. Based on the comparison, control or optimization actions, respectively are carried out directed at adjusting the load of the process. The corresponding schematic procedure as illustrated in FIG. 11a and FIG. 11b is also the basis for a corresponding computer program product adapted to control the corresponding monitoring and/or control and/or optimization process for chromatography.

Example 12: Control of a Twin Column Countercurrent Sequential Loading Process, Low Impurity Signals The sequential loading process to be controlled, was used to purify an $IgG_1$ monoclonal antibody from clarified cell culture harvest. The process was operated on a Contichrom CUBE Combined 30 system (ChromaCon A. G., Switzerland) with two columns of 5 mm inner diameter and 50 mm bed height (column volume CV=1 mL), packed with the protein A affinity material MAbSelect Sure. A UV detector was mounted behind each column and monitoring absorbance at 280 nm (A280).

The following buffers were used: 20 mM Phosphate pH 7.2 (buffer A), 10 mM Citrate pH 2.7 (buffer B), 0.1 M NaOH (cleaning buffer).

The process protocol included a washing step of 4 column volumes (CVs) of buffer A, an elution step of 8 CVs with buffer B, a cleaning step of 3 CVs with 0.1 M NaOH, a first re-equilibration step with 5 CVs with buffer B and a second re-equilibration step with 10 CVs of buffer A. An interconnected washing step of 3 CVs was used.

All steps were run at a flow rate of 2 mL/min.

Figure 12:
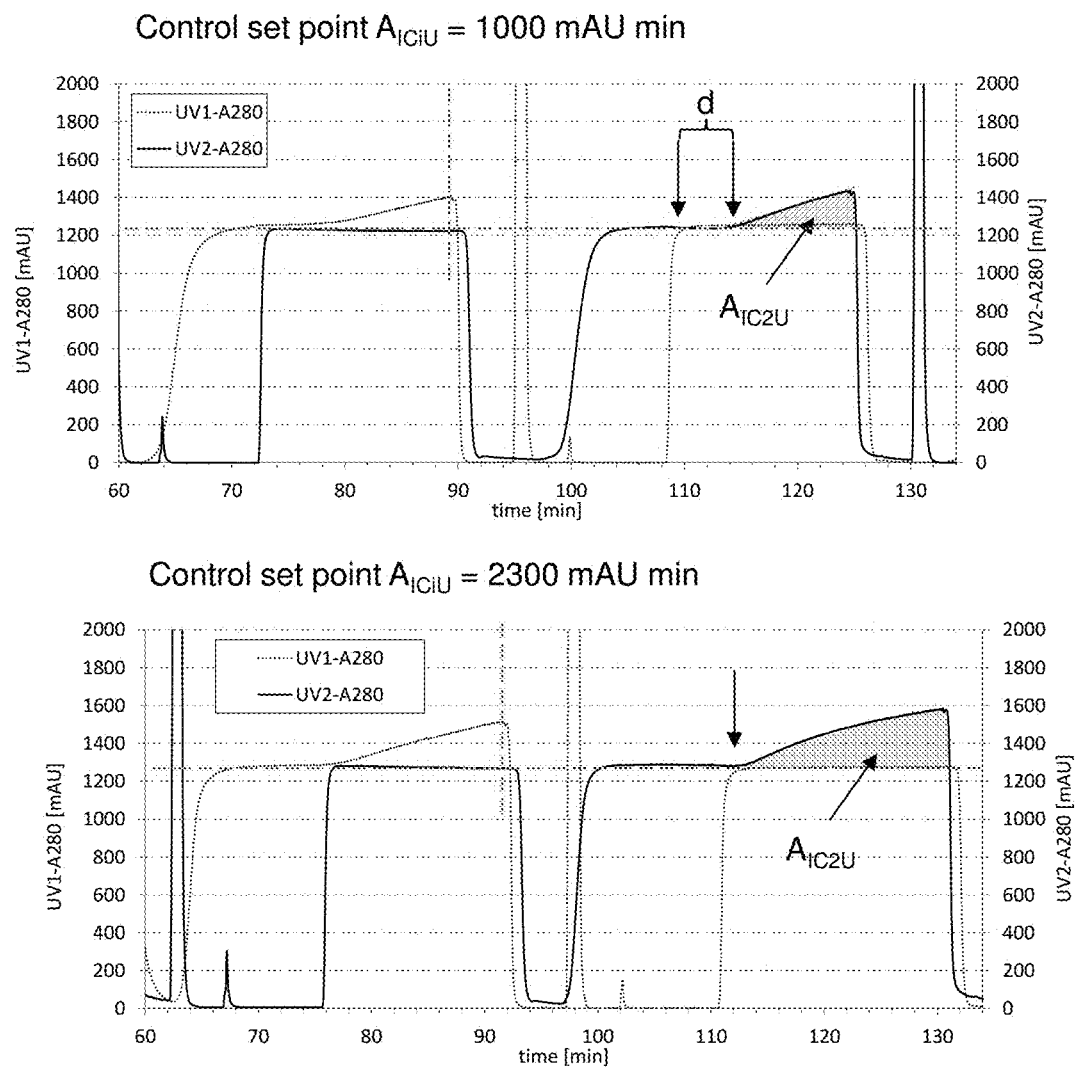
FIG. 12 in the top part shows chromatograms of two detectors UV1 and UV2 of a single cycle of a sequential loading process run with a set point of $A_{ICiU}$=1000 mAUmin and in the lower part shows the corresponding chromatograms of a single cycle of a sequential loading process run with a set point of $A_{ICiU}$=2300 mAUmin.

The twin column sequential loading process was operated with two different set points $A_{ICiU}$=1000 mAU min and $A_{ICiU}$=2300 mAU min. In each case the interconnected loading phase was stopped after reaching the set point values and the interconnected wash step was started according to the method described in the preferred embodiments, which includes the following steps:

(a) measuring the interconnected phase signals $A_{ICiU}$ corresponding to the effluents of at least two, preferably all columns (i) in an interconnected state upstream and/or downstream positions in at least one cycle or parts of one cycle using the detectors at the columns outlets;

(b) initiating a control action based on $A_{ICiU}$ reaching a specific set point value, in this case $A_{ICiU}$=1000 mAU min and $A_{ICiU}$=2300 mAU min, respectively. As control action, the interconnected loading phase was stopped upon $A_{ICiU}$ reaching the pre-defined set point values and the interconnected washing step was initiated. The resulting chromatograms are shown in FIG. 12 (one cycle of each run is shown). FIG. 12 also illustrates how the areas for the area set point control method were determined based on the example of the UV2 signal. The baseline for the area calculation of UV2 (horizontal dashed line above 1200 mAU, top part of FIG. 12) was determined at the beginning of the interconnected washing step with column 1 in the upstream and column 2 (with UV2) in the downstream position (vertical dashed line). At this position the UV2 signal corresponds to a stable baseline caused by the impurities that are breaking through from column 2. The baseline is used in the subsequent interconnected loading phase with column 2 being upstream and column 1 being downstream to automatically integrate the UV2 signal on an ongoing basis, e.g. every second, using a computer software. As product of interest starts to break through from the upstream column 2, the calculated area starts to increase and when reaching a pre-defined set point value the interconnected loading phase is stopped and the interconnected washing phase is initiated.

The set point may also be determined automatically by a suitable computer software. FIG. 12 shows chromatograms from two runs of the presented process operated with different set points (top part $A_{ICiU}$=1000 mAU min, bottom part $A_{ICiU}$=2300 mAU min). It is one characteristic of runs with a smaller area $A_{ICiU}$ set point that the start of the rise of the detector signal due to breakthrough of the compound of interest from the upstream column takes place later than in runs with a larger area set point. Thus with a smaller area $A_{ICiU}$ set point the columns are loaded in series for a longer period of time until the compound of interest starts to break through from the upstream column. In FIG. 12 the interval between the start of the interconnected loading of the columns and the breakthrough of compound of interest from the upstream column is indicated by "d".

From a process performance optimization point of view it is desirable to achieve an early breakthrough of compound of interest from the upstream column when the columns are loaded in series. In the bottom part of FIG. 12 the start of breakthrough of the compound of interest almost coincides with the start of the interconnected loading phase (see vertical arrow). This leads to an improved process performance in terms of productivity compared to the previous run, however this comes at the cost of decreased process robustness, i.e. the process characterized by the chromatograms in the lower part may experience losses of the compound of interest (decrease in yield) even for small increases of the concentration of the compound of interest in the load material or for small decreases in column capacity (e.g. loss of capacity due to fouling or harsh cleaning.)

| | LIST OF REFERENCE SIGNS | | |
|---|---|---|---|
| B | Disconnected state or phase (batch state) of the sequential loading process | $Q_{feed,BT1L}$ | startup phase of the sequential loading process feed flow rate for single column operation that is significantly lower than maximum desired feed flow rate |
| IC | Interconnected state or phase of the sequential loading process | | |
| $t_B$ | duration of the disconnected phase of the sequential loading process | $EV_{1H,1}$ | elution volume corresponding to low breakthrough based on a single column breakthrough curve recorded for $Q_{feedJC}$ |
| $t_{IC}$ | duration of the interconnected phase of the sequential loading process | $EV_{1L,1}$ | elution volume corresponding |

-continued

LIST OF REFERENCE SIGNS

| Symbol | Description |
|---|---|
| $t_{startup}$ | duration of the startup phase of the sequential loading process |
| $t_{wash,IC}$ | duration of the wash phase of the sequential loading process |
| $Q_{feed}$ | feed flow rate, general |
| $Q_{feed,IC}$ | second flow rate, feed flow rate during the interconnected phase of the sequential loading process |
| $Q_{wash,IC}$ | wash flow rate during the interconnected phase of the sequential loading process |
| $Q_{feed,B}$ | first flow rate, feed flow rate during the disconnected phase of the sequential loading process |
| $Q_{feed,startup}$ | feed flow rate during the startup, typically 30-90%. |
| $W$ | ratio between $Q_{feed,BT1L}$ and $Q_{feed,IC}$; Typically 50-90% |
| $Z$ | safety factor for loading, typically 60-90% |
| $V_{dead}$ | dead volume, volume of interstitial liquid in one column |
| $V_{col}$ | empty column volume |
| $C_{feed}$ | feed concentration |
| $DBC_{1H}(EV)$ | single column breakthrough curve, recorded at $Q_{feed,IC}$, as a function of the elution volume |
| $DBC_2(EV)$ | breakthrough curve of two interconnected columns, recorded at $Q_{feed,IC}$ as a function of the elution volume |
| $dEV$ | elution volume increment for integration |
| $TL$ | Target load value in the disconnected phase of the sequential loading process |
| $PL$ | Preload value in the interconnected phase of the sequential loading process |
| $A_{peaki}$ | area confined by the elution peak curve of column i and a horizontal baseline corresponding to the value of the equilibrated empty column or a baseline defined the interconnected phase IC when column i is in the downstream position. |
| $A_{peaki,max}$ | Area $A_{peaki}$ that corresponds to the maximum possible load of the process at 100% yield |
| $L$ | Load, corresponds to the amount of new product compound injected into the |
| $EV_{1H,X}$ | elution volume corresponding to low breakthrough based on a single column breakthrough curve recorded for $Q_{feed,BT1L}$ elution volume corresponding to a high breakthrough based on a single column breakthrough curve recorded for $Q_{feed,IC}$ |
| $EV_2$ | elution volume corresponding to low breakthrough based on a sequentially interconnected column breakthrough curve recorded for $Q_{feed,IC}$, multiplied with the safety factor Z. |
| $EV_Y$ | smaller of the two values $EV_{1H,X}$, $EV_2$ |
| $X$ | magnitude of breakthrough, by other criteria such as points of operating parameter changes |
| $i$ | column index, detector index |
| $n$ | cycle number |
| $A_{Bi}$ | area confined by breakthrough curve and a horizontal baseline corresponding to plateau signal value of the non-adsorbing impurities measured at the outlet of column i during the disconnected phase B |
| $A_{ICiU}$ | area confined by breakthrough curve and a horizontal baseline corresponding to plateau signal value of the non-adsorbing impurities measured at the outlet of column i by detector i during the interconnected phase IC when column i is in the upstream position. |
| $A_{ICiD}$ | area confined by breakthrough curve and a horizontal baseline corresponding to plateau signal value of the non-adsorbing impurities measured at the outlet of column i by detector i during system during one cycle through the feed stream(s), divided by the total bed volume of the chromatographic columns |
| $PLR$ | product loss ratio |

What is claimed is:

1. A method for control and/or monitoring and/or optimization of a chromatographic process, in which the chromatographic process uses only two columns, consisting of a first column and a second column, the first column having a first column inlet and a first column outlet, the second column having a second column inlet and a second column outlet, the two columns being operated in said chromatographic process for an isolation of target molecules from a feed consisting of the target molecules and impurities to be separated from the target molecules using the following steps in order:

a first batch step, performed during a batch timespan, wherein the two columns are disconnected, the first column is loaded with the feed via the first column inlet at a first flow rate and the first column outlet is directed to a waste, and from the second column, the target molecules are recovered via the second column outlet based on the second column being subjected to a regeneration process;

a first interconnected step, performed during an interconnected timespan, wherein the first column outlet is connected to the second column inlet, the first column thus being a first upstream column and the second column thus being a first downstream column, the first column has a dynamic breakthrough capacity of the target molecules beyond which the target molecules exit the first column via the first column outlet, the first column is loaded beyond the dynamic breakthrough capacity with the feed via the first column inlet, the second column outlet is directed to the waste, and wherein during a subsequent washing timespan, the first column outlet remains connected to the second column inlet, the first column and the second column are subjected to a subsequent washing process by washing with a subsequent-washing-solvent, and/or a subsequent-washing-buffer, and an eluate exiting the second column outlet is directed to the waste;

said first batch step and first interconnected step forming a first cycle, a second batch step, during which the two columns are disconnected and wherein the first column performs all tasks of the second column in the first batch step, and the second column performs all tasks of the first column in the first batch step; and a second interconnected step, wherein the second column outlet is connected to the first column inlet, the first column performs all tasks of the second column in the first interconnected step and the second column performs all tasks of the first column in the first interconnected step;

said second batch step and second interconnected step forming a subsequent cycle, wherein downstream of each column, a detector is located at said first and second column outlets, capable of detecting said target molecules and/or impurities, wherein the method comprises the following steps:

(a) measuring interconnected areas ($A_{ICiU}$) corresponding to effluents of all columns in an interconnected state in at least one cycle or parts of one cycle using the detectors at the column outlets;

followed by the steps:

(b) comparing the interconnected areas ($A_{ICiU}$) of a current cycle n with an interconnected area of at least one previous cycle ($A_{ICiU,n-1}$) of the two detectors by calculating ratios between interconnected areas ($A_{ICiU}$ and $A_{ICiU,n-1}$);

and (c) using the ratios comparison from said step (b) of the two detectors in order to quantify a degree of a signal magnitude difference and using this signal magnitude difference for control and/or monitoring and/or optimization of at least one process parameter.

2. The method for control and/or monitoring and/or optimization of a chromatographic process according to claim 1, wherein in at least one of the first interconnected step (IC) and the second interconnected step (IC), a second flow rate ($Q_{feed,IC}$) is adapted to be 1.0-10.0 times larger than the first flow rate ($Q_{feed,B}$).

3. The method for control and/or monitoring and/or optimization of a chromatographic process according to claim 1, wherein in at least one of the first interconnected step (IC) and the second interconnected step (IC), a second flow rate ($Q_{feed,IC}$) and/or the interconnected timespan ($t_{IC}$) are adapted such that at the end of the interconnected timespan ($t_{IC}$), a feed concentration at an outlet of an upstream column is in the range of 30-90% of a feed concentration at an inlet of an upstream column, with the proviso that the values of the second flow rate ($Q_{feed,IC}$) and/or the interconnected timespan ($t_{IC}$) are adapted such that at the end of the interconnected timespan ($t_{IC}$) at the outlet of the downstream column, the feed concentration is below a breakthrough value of 0.25-5%, and that an elution volume corresponding to this breakthrough value can be multiplied with a safety factor in the range of 60-90%.

4. The method for control and/or monitoring and/or optimization of a chromatographic process according to claim 1, wherein the batch timespan ($t_B$) is chosen to be an accumulated time required for a recovery and regeneration of the respective column, wherein this accumulated time is given by an accumulated time required for the steps of:

(i) washing with at least one of a first solvent and a first buffer under conditions that the target molecules are not released from a stationary phase;

(ii) elution with at least one of a second solvent and a second buffer under conditions that the target molecules are released from the stationary phase;

(iii) cleaning in place using a solvent and/or buffer to release everything from the stationary phase; and W (iv) equilibration, by using at least one of a third solvent and a third buffer under conditions similar or the same as in the subsequent process steps;

wherein said first, second and third solvents and buffers, respectively, can be the same or different.

5. The method for control and/or monitoring and/or optimization of a chromatographic process according to claim 1, wherein the columns are affinity chromatography material loaded columns.

6. The method for control and/or monitoring and/or optimization of a chromatographic process according to claim 1, wherein at the outlet of each column a detector for an analysis of components at the outlet is located, both detectors being of the same type, wherein these detectors are selected from the following group: UV detector, visible light detector, IR detector, fluorescence detector, light scattering detector, refractive index detector, pH detector, conductivity detector, on-line HPLC analysis, Raman spectrometer and mass spectrometer.

7. The method for control and/or monitoring and/or optimization of a chromatographic process according to claim 1,
wherein the first cycle is preceded by a startup step, in which the columns are interconnected and wherein a larger amount of the feed is loaded into the first upstream column in comparison with an interconnected step (IC) of a cycle of the method, and/or
wherein the last cycle is followed by a shutdown step, in which the two columns are disconnected, and both columns are subjected to product recovery and column regeneration.

8. The method for control and/or monitoring and/or optimization of a chromatographic process according to claim 1, wherein the target molecules are one or a group of chemical reaction products, chemical separation products, biochemical reaction products, biological products, and derivatives, combinations and mixtures thereof.

9. The method for control and/or monitoring and/or optimization of a chromatographic process according to claim 1, wherein the target molecules are one or a group of natural products, metals, antibodies, antibody fragments, fusion proteins, recombinant glycoproteins, plasma proteins, and derivatives, combinations and mixtures thereof.

10. The method for control and/or monitoring and/or optimization of a chromatographic process according to claim 1, wherein the columns are affinity chromatography material loaded columns, wherein the chromatography material is in the form of particles, beads, membranes or monoliths.

11. A method for control and/or monitoring and/or optimization of a chromatographic process, in which the chromatographic process uses only two columns, consisting of a first column and a second column, the first column having a first column inlet and a first column outlet, the second column having a second column inlet and a second column outlet,
the two columns being operated in said chromatographic process for an isolation of target molecules from a feed consisting of the target molecules and impurities to be separated from the target molecules using the following steps in order:
a first batch step, performed during a batch timespan, wherein
the two columns are disconnected,
the first column is loaded with the feed via the first column inlet at a first flow rate and the first column outlet is directed to a waste, and
from the second column, the target molecules are recovered via the second column outlet based on the second column being subjected to a regeneration process;
a first interconnected step, performed during an interconnected timespan, wherein
the first column outlet is connected to the second column inlet, the first column thus being a first upstream column and the second column thus being a first downstream column,
the first column has a dynamic breakthrough capacity of the target molecules beyond which the target molecules exit the first column via the first column outlet,
the first column is loaded beyond the dynamic breakthrough capacity with the feed via the first column inlet,
the second column outlet is directed to the waste, and
wherein during a subsequent washing timespan,
the first column outlet remains connected to the second column inlet,
the first column and the second column are subjected to a subsequent washing process by washing with a subsequent-washing-solvent, and/or a subsequent-washing-buffer, and
an eluate exiting the second column outlet is directed to the waste;
said first batch step and first interconnected step forming a first cycle,
a second batch step, during which the two columns are disconnected and wherein the first column performs all tasks of the second column in the first batch step, and the second column performs all tasks of the first column in the first batch step; and
a second interconnected step, wherein the second column outlet is connected to the first column inlet, the first column performs all tasks of the second column in the first interconnected step and the second column performs all tasks of the first column in the first interconnected step,
said second batch step and second interconnected step forming a subsequent cycle,
wherein downstream of each column, a detector is located at said first and second column outlets capable of detecting said target molecules and/or said impurities,
wherein the method comprises the following steps:
(a) measuring disconnected areas ($A_{peaki}$) corresponding to effluents of one or of two columns in a product elution position in a disconnected state in at least one cycle or parts of one cycle using the detectors at the column outlets, followed by at least the following step,
(b) using the measured values of the disconnected areas ($A_{peaki}$) in said step (a) of the two detectors for control and/or monitoring and/or optimization of at least one process parameter,
wherein the columns are loaded such that the initially determined disconnected area ($A_{peaki}$) is smaller than 80% of a maximum disconnected area ($A_{peaki,max}$) that is expected or known from previous chromatographic runs or cycles or parts thereof of the same chromatographic run, and
wherein operating parameters are changed from cycle to cycle or multiples or parts thereof, such that a column load (L) is maximized while a ratio of the corresponding disconnected area ($A_{peaki,n}$) and the column load remains constant at a level defined by the column load and the disconnected area ($A_{peaki}$) in said step (a).

12. The method for control and/or monitoring and/or optimization of a chromatographic process according to claim 11, wherein in said step (b) an interconnected area ($A_{ICiU}$) of the two detectors for control and/or monitoring and/or optimization of the at least one process parameter is used.

13. The method for control and/or monitoring and/or optimization of a chromatographic process according to claim 11, wherein the method further comprises the following steps:

measuring interconnected areas ($A_{ICiU}$) corresponding to the effluents of all columns in an interconnected state in at least one cycle or parts of one cycle using the detectors at the column outlets;

comparing the disconnected areas ($A_{Bi,n}$ and/or $A_{peaki,n}$) of the two detectors of a current cycle n with a disconnected area of at least one previous cycle ($A_{Bi,n-1}$ and/or $A_{peaki,n-1}$), optionally including a comparison by calculating ratios between disconnected areas ($A_{Bi,n}/A_{Bi,n-1}$ and/or $A_{peaki,n}/A_{peaki,n-1}$) of the detectors; and comparing the interconnected areas ($A_{ICiU}$) of a current cycle n with an interconnected area of at least one previous cycle ($A_{ICiU,n-1}$) of the two detectors, optionally including a comparison by calculating ratios between interconnected areas ($A_{ICiU}$ and $A_{ICiU,n-1}$);

wherein the values of the interconnected areas ($A_{ICiU}$) comparison in the preceding step among the two detectors are compared in order to quantify a degree of a signal magnitude difference and using this signal magnitude difference for control and/or monitoring and/or optimization of at least one process parameter.

14. The method for control and/or monitoring and/or optimization of a chromatographic process according to claim 13, wherein the interconnected areas ($A_{ICiU}$) among the two detectors are compared by calculating ratios between interconnected areas ($A_{ICiU}$) of detectors and using these ratios for control and/or monitoring.

15. A method for control and/or monitoring and/or optimization of a chromatographic process, in which the chromatographic process uses only two columns, consisting of a first column and a second column, the first column having a first column inlet and a first column outlet, the second column having a second column inlet and a second column outlet, the two columns being operated in said chromatographic process for an isolation of target molecules from a feed consisting of the target molecules and impurities to be separated from the target molecules using the following steps in order:

a first batch step, performed during a batch timespan, wherein the two columns are disconnected, the first column is loaded with the feed via the first column inlet at a first flow rate and the first column outlet is directed to a waste, and from the second column, the target molecules are recovered via the second column outlet based on the second column being subjected to a regeneration process;

a first interconnected step, performed during an interconnected timespan, wherein the first column outlet is connected to the second column inlet, the first column thus being a first upstream column and the second column thus being a first downstream column, the first column has a dynamic breakthrough capacity of the target molecules beyond which the target molecules exit the first column via the first column outlet, the first column is loaded beyond the dynamic breakthrough capacity with the feed via the first column inlet, the second column outlet is directed to the waste, and wherein during a subsequent washing timespan, the first column outlet remains connected to the second column inlet, the first column and the second column are subjected to a subsequent washing process by washing with a subsequent-washing-solvent, and/or a subsequent-washing-buffer, and an eluate exiting the second column outlet is directed to the waste;

said first batch step and first interconnected step forming a first cycle, a second batch step, during which the two columns are disconnected and wherein the first column performs all tasks of the second column in the first batch step, and the second column performs all tasks of the first column in the first batch step; and a second interconnected step, wherein the second column outlet is connected to the first column inlet, the first column performs all tasks of the second column in the first interconnected step and the second column performs all tasks of the first column in the first interconnected step, said second batch step and second interconnected step forming a subsequent cycle, wherein downstream of each column at said first and second column outlets, a detector is located capable of detecting said target molecules and/or said impurities, wherein the method comprises the following steps:

(1) measuring interconnected areas ($A_{ICiU}$) corresponding to effluents of one or of two columns in an interconnected state in at least one cycle or parts of one cycle using the detectors at the column outlets;

and (2) using the measured values of the interconnected areas ($A_{ICiU}$) in said step (1) of one or both detectors for control and/or monitoring of at least one process parameter, based on the measured values of the interconnected areas ($A_{ICiU}$) reaching a specific target set point value, wherein the process parameter is related to at least one of timing, flow rates, load, yield, recovery, throughput, and buffer consumption of the process, and wherein, when the process parameter reaches a predefined or automatically calculated set point value based on the measured values of the interconnected areas ($A_{ICiU}$), an interconnected loading phase is stopped and an interconnected washing step or a subsequent loading step is initiated.

* * * * *